(12) United States Patent
Schmitz et al.

(10) Patent No.: US 7,629,340 B2
(45) Date of Patent: Dec. 8, 2009

(54) N-(6-MEMBERED AROMATIC RING)-AMIDO ANTI-VIRAL COMPOUNDS

(75) Inventors: Franz Ulrich Schmitz, Mill Valley, CA (US); Christopher Don Roberts, Belmont, CA (US); Ali Dehghani Mohammad Abadi, Campbell, CA (US); Ronald Conrad Griffith, Escondido, CA (US); Martin Robert Leivers, San Francisco, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/609,854

(22) Filed: Dec. 12, 2006

(65) Prior Publication Data

US 2007/0265262 A1 Nov. 15, 2007

Related U.S. Application Data

(60) Provisional application No. 60/749,771, filed on Dec. 12, 2005.

(51) Int. Cl.
*A61K 31/497* (2006.01)
*A61K 31/517* (2006.01)
*A61K 31/535* (2006.01)
*A61P 31/12* (2006.01)
*C07D 207/02* (2006.01)
*C07D 277/62* (2006.01)
*C07D 401/12* (2006.01)
*C07D 403/12* (2006.01)

(52) U.S. Cl. ............... 514/235.5; 514/254.01; 514/266.2; 514/314; 514/326; 514/367; 514/385; 514/422; 514/423; 544/141; 544/285; 544/372; 546/176; 546/208; 548/178; 548/306.1; 548/518; 548/525; 548/531

(58) Field of Classification Search ............... 514/235.5, 514/422, 423; 548/531
See application file for complete search history.

(56) References Cited

U.S. PATENT DOCUMENTS

| 4,107,288 | A | 8/1978 | Oppenheim et al. |
| 5,145,684 | A | 9/1992 | Liversidge et al. |
| 5,607,915 | A | 3/1997 | Patton |
| 5,738,985 | A | 4/1998 | Miles et al. |
| 2006/0276511 | A1 | 12/2006 | Serrano-Wu et al. |
| 2007/0265265 | A1 | 11/2007 | Schmitz et al. |

FOREIGN PATENT DOCUMENTS

WO WO 03/045912 * 6/2003
WO WO 2004/014313 A2 2/2004
WO WO 2004/014852 A2 2/2004

OTHER PUBLICATIONS

Njoroge et al. "Challenges in Modern Drug Discover: A Case Study of Boceprevir, an HCV Protease Inhibitor for the Treatment of Hepatitis C Virus Infection" Acc. Chem. Res. 2008, 41(1) 50-59.*
Mitsch et al. ("Non-thiol Farnesyltransferase Inhibitors: FTase-Inhibition and Cellular Activity of Benzophenone-based Bisubstrate Analogue Farnesyltransferase Inhibitors" Archiv der Pharmazie, 2003, 336, 242-250.).*
Beaulieu, P.L. et al. "Inhibitors of the HCV NS5B polymerase: new hope for the treatment of hepatitis C infections." *Curr Opin Investig Drugs* 5(8):838-50 (2004).
Ferrari, E. et al. "Characterization of soluble hepatitis C virus RNA-dependent RNA polymerase expressed in *Escherichia coli.*" *J Virol* 73(2):1649-54 (1999).
Fried, M.W. et al. "Peginterferon alfa-2a plus ribavirin for chronic hepatitis C virus infection." *N. Engl J Med* 347(13):975-82 (2002).
Griffith et al. "HCV Anti-viral Agents." *Ann Rep Med Chem* 39:223-37 (2004).
Hoofnagle, J.H. "Hepatitis C: the clinical spectrum of disease." *Hepatology* 26(3 Suppl 1):15S-20S (1997).
Horsmans, Y. et al. "Isatoribine, an agonist of TLR7, reduces plasma virus concentration in chronic hepatitis C infection." *Hepatology* 42(3):724-31 (2005).
Ishii, K. et al. "Expression of hepatitis C virus NS5B protein: characterization of its RNA polymerase activity and RNA binding." *Hepatology* 29(4):1227-35 (1999).
Lohmann, V. et al. "Selective stimulation of hepatitis C virus and pestivirus NS5B RNA polymerase activity by GTP." *J Biol Chem* 274(16):10807-15 (1999).
Moriishi, K. et al. "Mechanisms of hepatitis C virus infection." *Antivir Chem Chemother* 14(6):285-97 (2003).
Ni, Z.J. et al. "Progress and development of small molecule HCV antivirals." *Curr Opin Drug Discov Develop* 7(4):446-59 (2004).
Saunders, J.O. et al. "Inosine Monophosphate Dehydrogenase: Consideration of Structure, Kinetics and Therapeutic Potential." *Ann Rep Med Chem* 25:201-10 (2000).
Szabo, E. et al. "Viral hepatitis: new data on hepatitis C infection." *Pathol Oncol Res* 9(4):215-21 (2003).
Thomson, B.J. et al. "Hepatitis C virus infection." *Clin Microbiol Infect* 11(2):86-94 (2005).

(Continued)

*Primary Examiner*—Sharmila Gollamudi Landau
*Assistant Examiner*—Kortney L Klinkel
(74) *Attorney, Agent, or Firm*—Robert H. Brink

(57) ABSTRACT

Disclosed are compounds having Formula (I) and the compositions and methods relating to these compounds, for treating or preventing a viral infection mediated at least in part by a virus in the Flaviviridae family of viruses, wherein A, $R^2$, m, R, V, W, T, Z, $R^1$, Y, and p are disclosed herein.

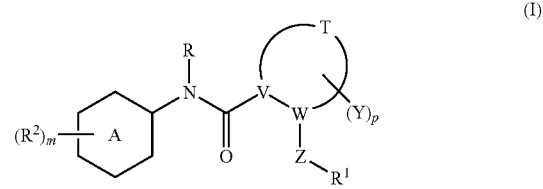

(I)

1 Claim, No Drawings

OTHER PUBLICATIONS

Watashi, K. et al. "Cyclophilin B is a functional regulator of hepatitis C virus RNA polymerase." *Mol Cell* 19(1):111-22 (2005).

Yamashita, T. et al. "RNA-dependent RNA polymerase activity of the soluble recombinant hepatitis C virus NS5B protein truncated at the C-terminal region." *J Biol Chem* 273(25):15479-86 (1998).

Krieger et al. "Enhancement of hepatitis C virus RNA replication by cell culture-adaptive mutations." *J Virol.* May 2001; 75(10):4614-24.

Denmark et al. "Synthesis of Phosphoramides for the Lewis Base-Catalyzed Allylation and Aldo Addition Reactions." *Journal of Organic Chemistry*, vol. 64, 1999, pp. 1958-1967.

Hadfield et al. "An Unexpected Mitsunobu Reaction. A Direct Route to the 2,5-Diaza-Bicyclo2.2.1Heptan-3-One Skeleton As a Gamma-Lactam Mimic of Beta-Lactam Antibiotics." *Journal of the Chemical Society*, Perkin Transactions 1, Chemical Society. Letchworth, GB, No. 4, 1997, pp. 503-509.

Mori et al. "New Synthesis of Pyrrolo-1, 4-Benzodiazepines by Utilizing Palladium-Catalyzed Carbonylation." *Chemical and Pharmaceutical Bulletin*, Pharmaceutical Society of Japan, Tokyo, JP, vol. 32, No. 10, Oct. 1984, pp. 3840-3847.

Rhyoo et al. "Use of Amino Amides Derived From Proline As Chiral Ligands in the Ruthenium(II)-Catalyzed Transfer Hydrogenation Reaction of Ketones." *Tetrahedron Letters*, Elsevier, Amsterdam, NL, vol. 42, No. 30, Jul. 23, 2001, pp. 5045-5048.

\* cited by examiner

# N-(6-MEMBERED AROMATIC RING)-AMIDO ANTI-VIRAL COMPOUNDS

CROSS-REFERENCE TO RELATED APPLICATION

This application claims the benefit under 35 U.S.C. 119(e) to provisional application U.S. Ser. No. 60/749,771 filed on Dec. 12, 2005, which is incorporated herein by reference in its entirety.

BACKGROUND OF THE INVENTION

Field of the Invention

The invention relates to the field of pharmaceutical chemistry, in particular to compounds, their preparation, compositions, and methods for treating viral infections in patients mediated, at least in part, by a virus in the Flaviviridae family of viruses.

REFERENCES

The following publications are cited in this application as superscript numbers:
1. Szabo, et al., Pathol. Oncol. Res. 2003, 9:215-221.
2. Hoofnagle J H, Hepatology 1997, 26:15 S-20S.
3. Thomson B J and Finch R G, Clin Microbial Infect. 2005, 11:86-94.
4. Moriishi K and Matsuura Y, Antivir. Chem. Chemother. 2003, 14:285-297.
5. Fried, et al., N. Engl. J. Med 2002, 347:975-982.
6. Ni, Z. J. and Wagman, A. S. Curr. Opin. Drug Discov. Devel. 2004, 7, 446-459.
7. Beaulieu, P. L. and Tsantrizos, Y. S., Curr. Opin. Investig. Drugs 2004, 5, 838-850.
8. Griffith, et al., Ann. Rep. Med. Chem. 39, 223-237, 2004.
9. Watashi, et al, Molecular Cell, 19, 111-122, 2005.
10. Horsmans, et al., Hepatology, 42, 724-731, 2005.

All of the above publications are herein incorporated by reference in their entirety to the same extent as if each individual publication was specifically and individually indicated to be incorporated by reference in its entirety.

STATE OF THE ART

Chronic infection with HCV is a major health problem associated with liver cirrhosis, hepatocellular carcinoma and liver failure. An estimated 170 million chronic carriers worldwide are at risk of developing liver disease.[1,2] In the United States alone 2.7 million are chronically infected with HCV, and the number of HCV-related deaths in 2000 was estimated between 8,000 and 10,000, a number that is expected to increase significantly over the next years. Infection by HCV is insidious in a high proportion of chronically infected (and infectious) carriers who may not experience clinical symptoms for many years. Liver cirrhosis can ultimately lead to liver failure. Liver failure resulting from chronic HCV infection is now recognized as a leading cause of liver transplantation.

HCV is a member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Because the replicative cycle of HCV does not involve any DNA intermediate and the virus is not integrated into the host genome, HCV infection can theoretically be cured. While the pathology of HCV infection affects mainly the liver, the virus is found in other cell types in the body including peripheral blood lymphocytes.[3,4]

At present, the standard treatment for chronic HCV is interferon alpha (IFN-alpha) in combination with ribavirin and this requires at least six (6) months of treatment. IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of pegylated IFN-alpha plus ribavirin. However, a number of patients still have significant side effects, primarily related to ribavirin. Ribavirin causes significant hemolysis in 10-20% of patients treated at currently recommended doses, and the drug is both teratogenic and embryotoxic. Even with recent improvements, a substantial fraction of patients do not respond with a sustained reduction in viral load 5 and there is a clear need for more effective antiviral therapy of HCV infection.

A number of approaches are being pursued to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4A protease/helicase and the NS5b RNA-dependent RNA polymerase are considered the most promising viral targets for new drugs.[6-8]

Besides targeting viral genes and their transcription and translation products, antiviral activity can also be achieved by targeting host cell proteins that are necessary for viral replication. For example, Watashi et al.[9] show how antiviral activity can be achieved by inhibiting host cell cyclophilins. Alternatively, a potent TLR7 agonist has been shown to reduce HCV plasma levels in humans.[10]

However, none of the compounds described above have progressed beyond clinical trials.[6,8]

Notwithstanding the above, the discovery of new compounds active against one or more members of the Flaviviridae family of viruses would be beneficial particularly in view of the difficulty currently faced in treating diseases mediated, at least in part, by one or more of such viruses.

SUMMARY OF THE INVENTION

This invention is directed to compounds, compositions, and methods for treating viral infections mediated, at least in part, by a virus in the Flaviviridae family of viruses. Specifically, this invention is directed to compounds, stereoisomers, tautomers, or pharmaceutically acceptable salts of Formula (I) and the related compositions and methods:

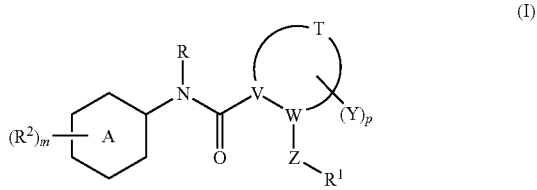

wherein:

A is a 6-membered aromatic ring wherein 1 to 3 ring carbon atoms are optionally replaced by nitrogen, wherein each nitrogen is optionally oxidized, and wherein A may be optionally fused to a 5 or 6 membered aryl, substituted aryl, heteroaryl, substituted heteroaryl, heterocycle, or substituted heterocycle to form a 9 or 10 membered bicyclic ring;

each $R^2$ is independently selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, substituted alkylthio, and $R^3$-L- wherein $R^3$ is selected from the group consisting of aryl, substituted aryl, heteroaryl, substituted heteroaryl, heterocyclic, and substituted heterocyclic; and L, defined herein in the $R^3$-L- orientation, is selected from the group consisting of a bond, —O—, —S—, —CH$_2$—, —CH$_2$CH$_2$—, —SCH$_2$—, —C(O)—, —C(S)—, —NHC(O)—, —C(O)NH—, —SO$_2$—, —SO$_2$NH—, —SO$_2$CH$_2$—, —OCH$_2$—, —CH$_2$CH$_2$NHC(O)—, —CH$_2$CH$_2$NHC(O)CH$_2$—, —NHN═C(CH$_3$CH$_2$OCO)—, —NHSO$_2$—, ═CH—, —NHC(O)CH$_2$S—, —NHC(O)CH$_2$C(O)—, spirocycloalkyl, —C(O)CH$_2$S—, and —C(O)CH$_2$O— provided that when L is ═CH—, $R^3$ is heterocyclic or substituted heterocyclic;

m is 1, 2, or 3;

R is selected from the group consisting of hydrogen, alkyl, substituted alkyl, cycloalkyl, and substituted cycloalkyl;

T is straight chain $C_1$-$C_6$ alkylene or $C_1$-$C_5$ heteroalkylene and forms a 3-8 membered ring with V and W;

V and W are both CH, or one of V or W is CH and the other of V or W is N;

Y is independently selected from the group consisting of halo, oxo, hydroxy, and alkoxy;

p is 0, 1, or 2;

Z is selected from the group consisting of C(O), C(S), and —SO$_2$—;

$R^1$ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, arylalkoxy, —OR$^{1a}$, —CH$_2$OR$^{1a}$, and —OCH$_2$R$^{1a}$; and $R^{1a}$ is selected from the group consisting of cycloalkyl, substituted cycloalkyl, heterocyclic, substituted heterocyclic, aryl, substituted aryl, heteroaryl, and substituted heteroaryl;

provided that when A is phenyl, V is CH, and W is N, then $R^2$ is not a substituted heterocycle having the structure

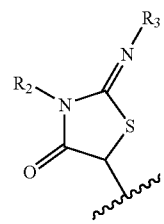

wherein $R_2$ and $R_3$ are as defined in WO 2004/014313 and WO 2004/014852; and provided that the compound is not 2-(3-Methylphenylcarbamoyl-pyrrolidine-1-carboxylic acid benzyl ester;

2-(4-Iodo-phenylcarbamoyl)-pyrrolidine-1-carboxylic acid benzyl ester;

2-(2,4-Dimethyl-phenylcarbamoyl)-pyrrolidine-1-carboxylic acid benzyl ester;

2-(2,5-Dimethyl-phenylcarbamoyl)-pyrrolidine-1-carboxylic acid benzyl ester;

2-(4-Methylphenylcarbamoyl)-5-oxo-pyrrolidine-1-carboxylic acid benzyl ester;

2-(2,4-Dimethyl-phenylcarbamoyl)-5-oxo-pyrrolidine-1-carboxylic acid benzyl ester;

2-(2,5-Dimethyl-phenylcarbamoyl)-5-oxo-pyrrolidine-1-carboxylic acid benzyl ester;

2-(3-Methylphenylcarbamoyl)-5-oxo-pyrrolidine-1-carboxylic acid benzyl ester;

2-(4-Methoxy-phenylcarbamoyl)-5-oxo-pyrrolidine-1-carboxylic acid benzyl ester;

2-Oxo-5-phenylcarbamoyl-pyrrolidine-1-carboxylic acid benzyl ester;

4-Hydroxy-2-(4-methoxy-phenylcarbamoyl)-pyrrolidine-1-carboxylic acid benzyl ester;

4-Hydroxy-2-(2-methoxy-phenylcarbamoyl)-pyrrolidine-1-carboxylic acid benzyl ester;

2-(2,5-Dimethyl-phenylcarbamoyl)-4-hydroxy-pyrrolidine-1-carboxylic acid benzyl ester;

4-Hydroxy-2-(4-iodo-2-methyl-phenylcarbamoyl)-pyrrolidine-1-carboxylic acid benzyl ester;

2-(4-Bromo-phenylcarbamoyl)-4-hydroxy-pyrrolidine-1-carboxylic acid benzyl ester;

4-Hydroxy-2-(4-iodo-phenylcarbamoyl)-pyrrolidine-1-carboxylic acid benzyl ester;

2-{4-[(Furan-2-carbonyl)-amino]-phenylcarbamoyl}-pyrrolidine-1-carboxylic acid benzyl ester;

2-{4-[(Pyridin-2-ylmethyl)-sulfamoyl]-phenylcarbamoyl}-pyrrolidine-1-carboxylic acid benzyl ester;

2-(4-Phenoxy-phenylcarbamoyl)-pyrrolidine-1-carboxylic acid benzyl ester;
2-(4-Methoxycarbonyl-phenylcarbamoyl)-pyrrolidine-1-carboxylic acid benzyl ester;
2-[3-(2-Isopropyl-5-methyl-phenoxy)-5-nitro-phenylcarbamoyl]-pyrrolidine-1-carboxylic acid benzyl ester;
2-[4-Hydroxy-3-(5-methyl-benzooxazol-2-yl)-phenylcarbamoyl]-pyrrolidine-1-carboxylic acid benzyl ester;
2-[3-Hydroxy-4-(5-methyl-benzooxazol-2-yl)-phenylcarbamoyl]-pyrrolidine-1-carboxylic acid benzyl ester;
2-[3-(4-Fluoro-phenylsulfanyl)-5-nitro-phenylcarbamoyl]-pyrrolidine-1-carboxylic acid benzyl ester;
Benzyl 2-(3-(N-(3-chlorophenyl)-N-(2-isopropoxy-2-oxoethyl)sulfamoyl)phenylcarbamoyl)pyrrolidine-1-carboxylate;
Benzyl 2-(4-(decahydroquinoline-1-carbonyl)phenylcarbamoyl)pyrrolidine-1-carboxylate;
Benzyl 2-(2-(methoxycarbonyl)phenylcarbamoyl)pyrrolidine-1-carboxylate;
Benzyl 2-(4-aminoquinazolin-6-ylcarbamoyl)pyrrolidine-1-carboxylate;
Benzyl 2-(2,4-diaminoquinazolin-6-ylcarbamoyl)pyrrolidine-1-carboxylate; or
tert-Butyl 2-(2,4-diaminoquinazolin-6-ylcarbamoyl)pyrrolidine-1-carboxylate.

DETAILED DESCRIPTION

Throughout this application, the text refers to various embodiments of the present compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Definitions

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to straight or branched hydrocarbyl groups having from 2 to 6 carbon atoms and preferably 2 to 4 carbon atoms and having at least 1 and preferably from 1 to 2 sites of vinyl (>C═C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxy substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxy substitution is not attached to an acetylenic carbon atom.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$— or —$CH(CH_3)CH_2$—), butylene (—$CH_2CH_2CH_2CH_2$—), isobutylene (—$CH_2CH(CH_3)CH_2$—), sec-butylene (—$CH_2CH_2(CH_3)CH$—) and the like. "Straight chain $C_1$-$C_6$ alkylene" refers to unbranched alkylene groups having from 1 to 6 carbons. "Straight chain $C_2$-$C_6$ alkylene" refers to unbranched alkylene groups having from 2 to 6 carbons.

"$C_1$-$C_5$ heteroalkylene" refers to straight chain $C_2$-$C_6$ alkylene groups where one or two —$CH_2$— groups are replaced with —S—, —S(O)—, —S(O)$_2$—, or —O— to give a heteroalkylene having one to five carbons provided that the heteroalkylene does not contain an —O—O—, —S—O—, —O—S—, or —S—S— group wherein the sulfur atom(s) are optionally oxidized to form S(O) or S(O)$_2$.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{47}C(O)$alkyl, —$NR^{47}C(O)$substituted alkyl, —$NR^{47}C(O)$cycloalkyl, —$NR^{47}C(O)$substituted cycloalkyl, —$NR^{47}C(O)$cycloalkenyl, —$NR^{47}C(O)$substituted cycloalkenyl, —$NR^{47}C(O)$alkenyl, —$NR^{47}C(O)$substituted alkenyl, —$NR^{47}C(O)$alkynyl, —$NR^{47}C(O)$substituted alkynyl, —$NR^{47}C(O)$aryl, —$NR^{47}C(O)$substituted aryl, —$NR^{47}C(O)$heteroaryl, —$NR^{47}C(O)$substituted heteroaryl, —$NR^{47}C(O)$heterocyclic, and —$NR^{47}C(O)$substituted heterocyclic wherein $R^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{48}R^{49}$ where $R^{48}$ and $R^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{48}$ is hydrogen and $R^{49}$ is alkyl, the substituted amino group is sometimes referred to herein as alkylamino. When $R^{48}$ and $R^{49}$ are alkyl, the substituted amino group is sometimes referred to herein as dialkylamino. When referring to a monosubstituted amino, it is meant that either $R^{48}$ or $R^{49}$ is hydrogen but not both. When referring to a disubstituted amino, it is meant that neither $R^{48}$ nor $R^{49}$ are hydrogen.

"Aminocarbonyl" refers to the group —$C(O)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —$C(S)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{47}C(O)NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^{47}$C(S)NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—SO$_2$NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{47}$SO$_2$NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{52}$)NR$^{50}$R$^{51}$ where R$^{50}$, R$^{51}$, and R$^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —$NR^{47}$C(O)O-alkyl, —$NR^{47}$C(O)O-substituted alkyl, —$NR^{47}$C(O)O-alkenyl, —$NR^{47}$C(O)O-substituted alkenyl, —$NR^{47}$C(O)O-alkynyl, —$NR^{47}$C(O)O-substituted alkynyl, —$NR^{47}$C(O)O-aryl, —$NR^{47}$C(O)O-substituted aryl, —$NR^{47}$C(O)O-cycloalkyl, —$NR^{47}$C(O)O-substituted cycloalkyl, —$NR^{47}$C(O)O-cycloalkenyl, —$NR^{47}$C(O)O-substituted cycloalkenyl, —$NR^{47}$C(O)O-heteroaryl, —$NR^{47}$C(O)O-substituted heteroaryl, —$NR^{47}$C(O)O-heterocyclic, and —$NR^{47}$C(O)O-substituted heterocyclic wherein $R^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)$NH_2$.

"Substituted guanidino" refers to —$NR^{53}$C(=$NR^{53}$)N($R^{53}$)$_2$ where each $R^{53}$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two $R^{53}$ groups attached to a common guanidino nitrogen atom are optionally joined together with the nitrogen bound thereto to form a heterocyclic or substituted heterocyclic group, provided that at least one $R^{53}$ is not hydrogen, and wherein said substituents are as defined herein.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Haloalkoxy" refers to alkoxy groups substituted with 1 to 5, 1 to 3, or 1 to 2 halo groups, wherein alkoxy and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O$^-$).

"Spirocycloalkyl" and "spiro ring systems" refers to divalent cyclic groups from 3 to 10 carbon atoms having a cycloalkyl ring with a spiro union (the union formed by a single atom which is the only common member of the rings) as exemplified by the following structure:

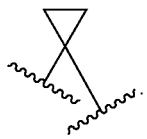

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO$_2$—, phenyl-SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thioxo" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Prodrug" refers to art recognized modifications to one or more functional groups which functional groups are metabolized in vivo to provide a compound of this invention or an active metabolite thereof. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

"Patient" refers to mammals and includes humans and non-human mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate [see Stahl and Wermuth, eds., "Handbook of Pharmaceutically Acceptable Salts", (2002), Verlag Helvetica Chimica Acta, Zürich, Switzerland, for an extensive discussion of pharmaceutical salts, their selection, preparation, and use.

"Therapeutically effective amount" is an amount sufficient to treat a specified disorder or disease.

"Treat" or "Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

The compounds disclosed in WO 2004/014313 and WO 2004/014852 are not intended to be included in the present invention. WO 2004/014313 and WO 2004/014852 relate to compounds having the group

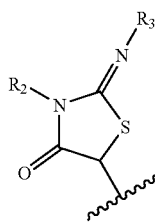

wherein:
  $R_2$ and $R_3$ are each independently selected from the group consisting of $C_{1-6}$ alkyl, $C_{3-7}$ cycloalkyl, $C_{6-10}$ aryl, $C_{1-6}$ alkoxy, $C_{6-10}$ aryloxy, Het, $C_{6-10}$ aryl ($C_{1-6}$) alkyl, $C_{6-10}$ aryl ($C_{1-6}$) alkoxy, acyl ($C_{1-6}$) alkoxy, with the proviso that one of $R_2$ or $R_3$ can be a bond wherein $R_2$ and $R_3$ are joined to form a cyclic structure;
  wherein "alkyl" as used with respect to $R_2$ and $R_3$ means acyclic, straight or branched chain alkyl substituents having the specified number of carbon atoms and includes, for example, methyl, ethyl, propyl, butyl, tert-butyl, hexyl, 1-methylethyl, 1-methylpropyl, 2-methylpropyl, 1,1-dimethylethyl;
  wherein "alkoxy" as used with respect to $R_2$ and $R_3$ means an alkyl group with the indicated number of carbon atoms attached to an oxygen atom and includes, for example, methoxy, ethoxy, propoxy, 1-methylethoxy, butoxy and 1,1-dimethylethoxy;
  wherein "cycloalkyl" as used with respect to $R_2$ and $R_3$ means a cycloalkyl substituent containing the indicated number of carbon atoms and includes, for example, cyclopropyl, cyclobutyl, cyclopentyl, cyclohexyl, cycloheptyl and spiro cyclic groups such as spirocyclopropyl and spirocyclobutyl;
  wherein "aryl" as used with respect to $R_2$ and $R_3$ means an aromatic moiety containing the indicated number of carbon atoms, such as, but not limited to phenyl, indanyl or naphthyl;
  wherein "$C_{6-10}$ aryl" as used with respect to $R_2$ and $R_3$ means an aromatic moiety having from six to ten carbon atoms which may be in the form of a monocyclic or bicyclic structure and include those substituted with typical substituents known to those skilled in the art, e.g., halogen, hydroxy, carboxy, carbonyl, nitro, sulfo, amino, cyano, dialkylamino haloalkyl, $CF_3$, haloalkoxy, thioalkyl, alkanoyl, SH, alkylamino, alkylamide, dialkylamide, carboxyester, alkylsulfone, alkylsulfonamide and alkyl (alkoxy)amine;
  wherein "heterocycle", also referred to as "Het", as used with respect to $R_2$ and $R_3$ means 7-12 membered bicyclic heterocycles and 5-7 membered monocyclic heterocycles;
  wherein "bicyclic heterocycles" as used with respect to $R_2$ and $R_3$ includes 7-12 membered fused bicyclic ring systems (both rings share an adjacent pair of atoms) containing from one to four heteroatoms selected from nitrogen, oxygen and sulfur; wherein both rings of the heterocycle are fully unsaturated; wherein the nitrogen and sulfur heteroatoms atoms may be optionally oxidized; wherein the bicyclic heterocycle may contain the heteroatoms in one or both rings; and wherein the heterocycles include those substituted with typical substituents known to those skilled in the art, on any of the ring carbon atoms; and
  wherein "monocyclic heterocycles" as used with respect to $R_2$ and $R_3$ includes 5-7 membered saturated, partially saturated or fully unsaturated ring system containing in the ring from one to four heteroatoms selected from nitrogen, oxygen and sulfur, wherein the sulfur and nitrogen heteroatoms may be optionally oxidized; and include those monocyclic heterocycles substituted with typical substituents known to those skilled in the art.

Accordingly, the present invention provides a compound of Formula (I), a stereoisomer, tautomer, or pharmaceutically acceptable salt thereof

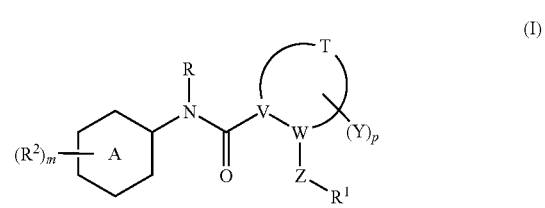

wherein:
A is a 6-membered aromatic ring wherein 1 to 3 ring carbon atoms are optionally replaced by nitrogen, wherein each nitrogen is optionally oxidized, and wherein A may be optionally fused to a 5 or 6 membered aryl, substituted aryl, heteroaryl, substituted heteroaryl, heterocycle, or substituted heterocycle to form a 9 or 10 membered bicyclic ring;

each R² is independently selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, substituted sulfonyloxy, thioacyl, thiol, alkylthio, substituted alkylthio, and R³-L- wherein R³ is selected from the group consisting of aryl, substituted aryl, heteroaryl, substituted heteroaryl, heterocyclic, and substituted heterocyclic; and L, defined herein in the R³-L- orientation, is selected from the group consisting of a bond, —O—, —S—, —CH₂—, —CH₂CH₂—, —SCH₂—, —C(O)—, —C(S)—, —NHC(O)—, —C(O)NH—, —SO₂—, —SO₂NH—, —SO₂CH₂—, —OCH₂—, —CH₂CH₂NHC(O)—, —CH₂CH₂NHC(O)CH₂—, —NHN=C(CH₃CH₂OCO)—, —NHSO₂—, =CH—, —NHC(O)CH₂S—, —NHC(O)CH₂C(O)—, spirocycloalkyl, —C(O)CH₂S—, and —C(O)CH₂O— provided that when L is =CH—, R³ is heterocyclic or substituted heterocyclic;

m is 1, 2, or 3;

R is selected from the group consisting of hydrogen, alkyl, substituted alkyl, cycloalkyl, and substituted cycloalkyl;

T is straight chain $C_1$-$C_6$ alkylene or $C_1$-$C_5$ heteroalkylene and forms a 3-8 membered ring with V and W;

V and W are both CH, or one of V or W is CH and the other of V or W is N;

Y is independently selected from the group consisting of halo, oxo, hydroxy, and alkoxy;

p is 0, 1, or 2;

Z is selected from the group consisting of C(O), C(S), and —SO₂—;

R¹ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, arylalkoxy, —OR$^{1a}$, —CH₂OR$^{1a}$, and —OCH₂R$^{1a}$; and R$^{1a}$ is selected from the group consisting of cycloalkyl, substituted cycloalkyl, heterocyclic, substituted heterocyclic, aryl, substituted aryl, heteroaryl, and substituted heteroaryl;

provided that when A is phenyl, V is CH, and W is N, then R² is not a substituted heterocycle having the structure

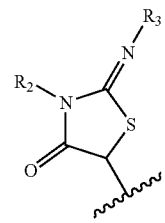

wherein R₂ and R₃ are as defined in WO 2004/014313 and WO 2004/014852; and provided that the compound is not 2-(3-Methylphenylcarbamoyl-pyrrolidine-1-carboxylic acid benzyl ester;

2-(4-Iodo-phenylcarbamoyl)-pyrrolidine-1-carboxylic acid benzyl ester;

2-(2,4-Dimethyl-phenylcarbamoyl)-pyrrolidine-1-carboxylic acid benzyl ester;

2-(2,5-Dimethyl-phenylcarbamoyl)-pyrrolidine-1-carboxylic acid benzyl ester;

2-(4-Methylphenylcarbamoyl)-5-oxo-pyrrolidine-1-carboxylic acid benzyl ester;

2-(2,4-Dimethyl-phenylcarbamoyl)-5-oxo-pyrrolidine-1-carboxylic acid benzyl ester;

2-(2,5-Dimethyl-phenylcarbamoyl)-5-oxo-pyrrolidine-1-carboxylic acid benzyl ester;

2-(3-Methylphenylcarbamoyl)-5-oxo-pyrrolidine-1-carboxylic acid benzyl ester;

2-(4-Methoxy-phenylcarbamoyl)-5-oxo-pyrrolidine-1-carboxylic acid benzyl ester;

2-Oxo-5-phenylcarbamoyl-pyrrolidine-1-carboxylic acid benzyl ester;

4-Hydroxy-2-(4-methoxy-phenylcarbamoyl)-pyrrolidine-1-carboxylic acid benzyl ester;

4-Hydroxy-2-(2-methoxy-phenylcarbamoyl)-pyrrolidine-1-carboxylic acid benzyl ester;

2-(2,5-Dimethyl-phenylcarbamoyl)-4-hydroxy-pyrrolidine-1-carboxylic acid benzyl ester;

4-Hydroxy-2-(4-iodo-2-methyl-phenylcarbamoyl)-pyrrolidine-1-carboxylic acid benzyl ester;

2-(4-Bromo-phenylcarbamoyl)-4-hydroxy-pyrrolidine-1-carboxylic acid benzyl ester;

4-Hydroxy-2-(4-iodo-phenylcarbamoyl)-pyrrolidine-1-carboxylic acid benzyl ester;

2-{4-[(Furan-2-carbonyl)-amino]-phenylcarbamoyl}-pyrrolidine-1-carboxylic acid benzyl ester;

2-{4-[(Pyridin-2-ylmethyl)-sulfamoyl]-phenylcarbamoyl}-pyrrolidine-1-carboxylic acid benzyl ester;

2-(4-Phenoxy-phenylcarbamoyl)-pyrrolidine-1-carboxylic acid benzyl ester;

2-(4-Methoxycarbonyl-phenylcarbamoyl)-pyrrolidine-1-carboxylic acid benzyl ester;

2-[3-(2-Isopropyl-5-methyl-phenoxy)-5-nitro-phenylcarbamoyl]-pyrrolidine-1-carboxylic acid benzyl ester;

2-[4-Hydroxy-3-(5-methyl-benzooxazol-2-yl)-phenylcarbamoyl]-pyrrolidine-1-carboxylic acid benzyl ester;

2-[3-Hydroxy-4-(5-methyl-benzooxazol-2-yl)-phenylcarbamoyl]-pyrrolidine-1-carboxylic acid benzyl ester;

2-[3-(4-Fluoro-phenylsulfanyl)-5-nitro-phenylcarbamoyl]-pyrrolidine-1-carboxylic acid benzyl ester;

Benzyl 2-(3-(N-(3-chlorophenyl)-N-(2-isopropoxy-2-oxoethyl)sulfamoyl)phenylcarbamoyl)pyrrolidine-1-carboxylate;

Benzyl 2-(4-(decahydroquinoline-1-carbonyl)phenylcarbamoyl)pyrrolidine-1-carboxylate;
Benzyl 2-(2-(methoxycarbonyl)phenylcarbamoyl)pyrrolidine-1-carboxylate;
Benzyl 2-(4-aminoquinazolin-6-ylcarbamoyl)pyrrolidine-1-carboxylate;
Benzyl 2-(2,4-diaminoquinazolin-6-ylcarbamoyl)pyrrolidine-1-carboxylate; or
tert-Butyl 2-(2,4-diaminoquinazolin-6-ylcarbamoyl)pyrrolidine-1-carboxylate.

In some embodiments, the invention provides compounds of Formula (I) where A is phenyl.

In some embodiments, at least one of $R^2$ is $R^3$-L- wherein $R^3$ is selected from the group consisting of aryl, substituted aryl, heteroaryl, substituted heteroaryl, heterocyclic, and substituted heterocyclic; and L, defined herein in the $R^3$-L- orientation, is selected from the group consisting of a bond, —O—, —S—, —$CH_2$—, —C(O)—, —C(S)—, —NH—, —NHC(O)—, —C(O)NH—, —$SO_2$—, —$SO_2$NH—, —$NHSO_2$—, =CH—, —NHC(O)$CH_2$C(O)—, and —C(O)$CH_2$O—, provided that when L is =CH—, $R^3$ is heterocyclic or substituted heterocyclic.

In some embodiments, the invention provides compounds of Formula (I) where R is hydrogen.

In some embodiments, the invention provides compounds of Formula (I) where T is selected from the group consisting of —$CH_2$—, —$CH_2CH_2$—, —$CH_2CH_2CH_2$—, —$CH_2SCH_2$—, and —$CH_2CH_2CH_2CH_2$—. In some aspects, R is hydrogen.

In some embodiments, the invention provides compounds of Formula (I) where, T is —$CH_2CH_2CH_2$—.

In some embodiments, V is CH and W is N.

In some embodiments, p is 0.

In some embodiments, Z is —C(O)—.

In some embodiments, $R^1$ is arylalkoxy.

The present invention further provides a compound having Formula (II) or a stereoisomer, tautomer, or a pharmaceutically acceptable salt thereof

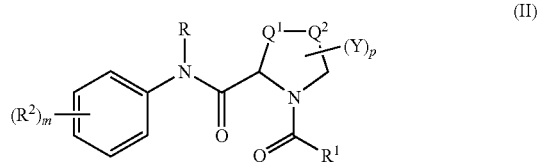

wherein:
R, $R^1$, $R^2$, Y, p, and m are previously defined;
at least one of $R^2$ is $R^3$-L- wherein $R^3$ is selected from the group consisting of aryl, substituted aryl, heteroaryl, substituted heteroaryl, heterocyclic, and substituted heterocyclic, and L, defined herein in the $R^3$-L- orientation, is selected from the group consisting of a bond, —O—, —S—, —$CH_2$—, —C(O)—, —C(S)—, —NH—, —NHC(O)—, —$SO_2$—, —$SO_2$NH—, —$NHSO_2$—, =CH—, —NHC(O)$CH_2$C(O)—, and —C(O)$CH_2$O—, provided that when L is =CH—, $R^3$ is heterocyclic or substituted heterocyclic; and
one of $Q^1$ or $Q^2$ is —O—, —S—, —S(O)—, —S(O)$_2$—, —C(O)—, CHY, or $CH_2$ and the other of $Q^1$ or $Q^2$ is $CH_2$;
provided that $R^2$ is not a substituted heterocycle having the structure

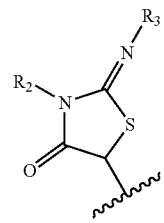

wherein $R_2$ and $R_3$ are as defined in WO 2004/014313 and WO 2004/014852; and provided that the compound is not
2-(3-Methylphenylcarbamoyl-pyrrolidine-1-carboxylic acid benzyl ester;
2-(4-Iodo-phenylcarbamoyl)-pyrrolidine-1-carboxylic acid benzyl ester;
2-(2,4-Dimethyl-phenylcarbamoyl)-pyrrolidine-1-carboxylic acid benzyl ester;
2-(2,5-Dimethyl-phenylcarbamoyl)-pyrrolidine-1-carboxylic acid benzyl ester;
2-(4-Methylphenylcarbamoyl)-5-oxo-pyrrolidine-1-carboxylic acid benzyl ester;
2-(2,4-Dimethyl-phenylcarbamoyl)-5-oxo-pyrrolidine-1-carboxylic acid benzyl ester;
2-(2,5-Dimethyl-phenylcarbamoyl)-5-oxo-pyrrolidine-1-carboxylic acid benzyl ester;
2-(3-Methylphenylcarbamoyl)-5-oxo-pyrrolidine-1-carboxylic acid benzyl ester;
2-(4-Methoxy-phenylcarbamoyl)-5-oxo-pyrrolidine-1-carboxylic acid benzyl ester;
2-Oxo-5-phenylcarbamoyl-pyrrolidine-1-carboxylic acid benzyl ester;
4-Hydroxy-2-(4-methoxy-phenylcarbamoyl)-pyrrolidine-1-carboxylic acid benzyl ester;
4-Hydroxy-2-(2-methoxy-phenylcarbamoyl)-pyrrolidine-1-carboxylic acid benzyl ester;
2-(2,5-Dimethyl-phenylcarbamoyl)-4-hydroxy-pyrrolidine-1-carboxylic acid benzyl ester;
4-Hydroxy-2-(4-iodo-2-methyl-phenylcarbamoyl)-pyrrolidine-1-carboxylic acid benzyl ester;
2-(4-Bromo-phenylcarbamoyl)-4-hydroxy-pyrrolidine-1-carboxylic acid benzyl ester;
4-Hydroxy-2-(4-iodo-phenylcarbamoyl)-pyrrolidine-1-carboxylic acid benzyl ester;
2-{4-[(Furan-2-carbonyl)-amino]-phenylcarbamoyl}-pyrrolidine-1-carboxylic acid benzyl ester;
2-{4-[(Pyridin-2-ylmethyl)-sulfamoyl]-phenylcarbamoyl}-pyrrolidine-1-carboxylic acid benzyl ester;
2-(4-Phenoxy-phenylcarbamoyl)-pyrrolidine-1-carboxylic acid benzyl ester;
2-(4-Methoxycarbonyl-phenylcarbamoyl)-pyrrolidine-1-carboxylic acid benzyl ester;
2-[3-(2-Isopropyl-5-methyl-phenoxy)-5-nitro-phenylcarbamoyl]-pyrrolidine-1-carboxylic acid benzyl ester;
2-[4-Hydroxy-3-(5-methyl-benzooxazol-2-yl)-phenylcarbamoyl]-pyrrolidine-1-carboxylic acid benzyl ester;
2-[3-Hydroxy-4-(5-methyl-benzooxazol-2-yl)-phenylcarbamoyl]-pyrrolidine-1-carboxylic acid benzyl ester;
2-[3-(4-Fluoro-phenylsulfanyl)-5-nitro-phenylcarbamoyl]-pyrrolidine-1-carboxylic acid benzyl ester;
Benzyl 2-(4-(decahydroquinoline-1-carbonyl)phenylcarbamoyl)pyrrolidine-1-carboxylate; or
Benzyl 2-(2-(methoxycarbonyl)phenylcarbamoyl)pyrrolidine-1-carboxylate.

In some embodiments, the present invention provides a compound of Formula (II) wherein the carbon atom bearing $Q^1$ and N has the S or R stereochemistry.

In some embodiments, the present invention provides a compound of Formula (II) wherein $R^3$ is aryl, substituted aryl, heteroaryl, or substituted heteroaryl and L is a bond, —$CH_2$—, —C(O)—, —NH—, or —$SO_2$— attached to the para position of the phenyl ring. In some aspects, L is a bond and $R^3$ is substituted or unsubstituted phenyl. In other aspects, L is —$CH_2$— and $R^3$ is substituted or unsubstituted benzimidazol-2-yl or naphthimidazol-2-yl, where substituted benzimidazol-2-yl or substituted naphthimidazol-2-yl are substituted with the same groups as substituted heteroaryl.

In other embodiments, the present invention provides a compound of Formula (II) wherein L is a bond and $R^3$ is aryl, substituted aryl, heteroaryl, or substituted heteroaryl attached to the meta position of the phenyl ring.

In some embodiments, R is hydrogen.

In some embodiments, $Q^1$ and $Q^2$ are $CH_2$. In some aspects R is hydrogen and p is 0. In some aspects $R^1$ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, and arylalkoxy.

In still other embodiments, the present invention provides compounds of Formula (I) or (II) wherein at least one $R^2$ is selected from the group consisting of nitro, halo, hydroxy, indol-5-yl, 5,6-dimethylbenzimidazol-2-ylmethyl, naphtho[2,3-d]imidazol-2-ylmethyl, 3-(phenyl)-phenyl), phenyloxy, pyridin-3-yloxy, 2,5-dimethoxyphenyl, 2,3-dimethoxyphenyl, 2,4-dimethoxyphenyl, 4-(4-methylphenylsulfonyl)phenyloxy, thien-2-yl, 3-methoxyphenyl, 3-phenoxymethylphenyl, 6-bromo-4,5-dimethylbenzimidazol-2-ylmethyl, 3,4-dimethoxyphenyl, 2-methoxyphenyl, 6-methoxybenzothiazol-2-yl-NHC(O)—, 2,6-dimethoxyphenyl, 6,7,8,9-tetrahydrodibenzofuran-2-yloxy, phenyl, phenyl-$SO_2$, pentafluorophenyloxy, 2,6-dimethoxyphenyl, 4-methoxyphenyl, 3-methylphenyloxy, benzimidazol-2-yl-methyl, phenyl-$SO_2$NH—, 5-furan-2-yl-[1,3,4]oxadiazol-2-yl, 4-methylpiperidin-1-yl-$SO_2$—, 2,6-dichlorophenyl-NHC(O)—, (3-methyl-5-oxo-1-phenylpyrazol-4-ylidenemethyl, 4-methoxyphenyl, 3-ethyl-2,6-dioxo-piperidin-3-yl, 2-chlorophenyl-NHC(O)$CH_2$C(O)—, 4-methylpiperazin-1-yl, morpholin-4-yl, piperidin-1-yl, piperidin-1-yl-C(O)—, 4-ethylamino-6-isopropylamino-[1,3,5]-triazin-2-yl-$NHSO_2$—, 4-methylpyridin-2-yl-$NHSO_2$—, morpholin-4-yl-C(O)—, benzothiazol-2-yl, morpholin-4-ylmethyl, pyrrolidin-1-ylmethyl, 5-chloro-pyridin-3-yloxy, 4-nitrophenyloxy, quinazolin-4-ylamino, morpholin-4-yl-C(O)$CH_2$O—, pyridin-4-yl, biphenyl, 5-cyano-benzimidazol-2-ylmethyl, pyridin-4-yl, 5-tert-butylbenzimidazol-2-ylmethyl, 5-bromobenzimidazol-2-ylmethyl, 4-methylbenzimidazol-2-ylmethyl, 5-methylbenzimidazol-2-ylmethyl, 4,5-dimethylbenzimidazol-2-ylmethyl, furan-2-yl-C(O)NH—, 2-pyridyl-$CH_2$$NHSO_2$—, 2-isopropyl-5-methylphenyloxy, 5-methylbenzo[d]oxazol-2-yl, 5-methylbenzo[d]oxazol-2-yl, 4-fluorophenyl, 4-aminomethylphenyl, benzo[1,3]dioxol-5-yl, naphthalen-2-yl, 4-dimethylaminophenyl, 4-methanesulfonylphenyl, 5-acetyl-thiophen-2-yl, 1-methyl-indol-5-yl, 4-acetylphenyl, 4-nitrophenyl, 3-aminophenyl, 2-carboxy-vinylphenyl, 4-acetylaminophenyl, 3-acetylaminophenyl, quinolin-3-yl, indol-4-yl, 2-oxo-2,3-dihydro-indol-5-yl, 2,3-dioxo-2,3-dihydro-indol-5-yl, and 2-methyl-quinolin-6-yl.

In still other embodiments, the present invention provides compounds of Formula (I) or (TI) wherein at least one $R^2$ is selected from the corresponding $R^2$ group in Table 1.

In yet other embodiments, the present invention provides a compound, stereoisomer, tautomer, or a pharmaceutically acceptable salt thereof selected from Table 1.

TABLE 1

| Ex. | Compound Structure | Compound Name |
|---|---|---|
| 6001 | 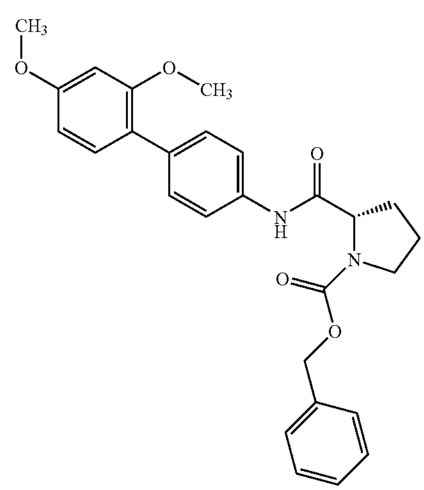 | 2-(2',4'-Dimethoxy-biphenyl-4-ylcarbamoyl)-pyrrolidine-1-carboxylic acid benzyl ester |

TABLE 1-continued

| Ex. | Compound Structure | Compound Name |
|---|---|---|
| 6002 | 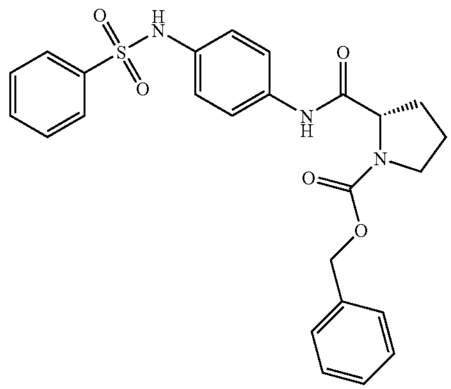 | 2-(4-Benzenesulfonylamino-phenylcarbamoyl)-pyrrolidine-1-carboxylic acid benzyl ester |
| 6003 | 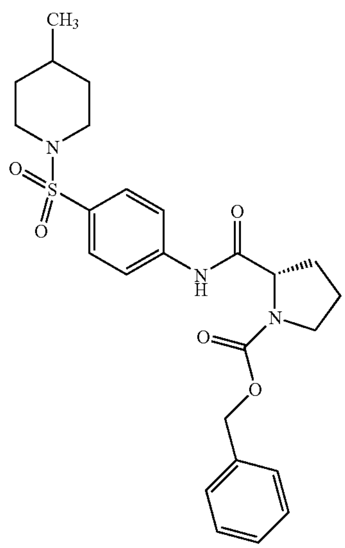 | 2-[4-(4-Methyl-piperidine-1-sulfonyl)-phenylcarbamoyl]-pyrrolidine-1-carboxylic acid benzyl ester |
| 6004 | 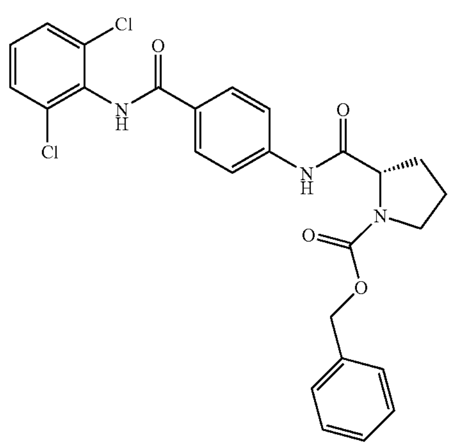 | 2-[4-(2,6-Dichloro-phenylcarbamoyl)-phenylcarbamoyl]-pyrrolidine-1-carboxylic acid benzyl ester |

TABLE 1-continued

| Ex. | Compound Structure | Compound Name |
| --- | --- | --- |
| 6005 | 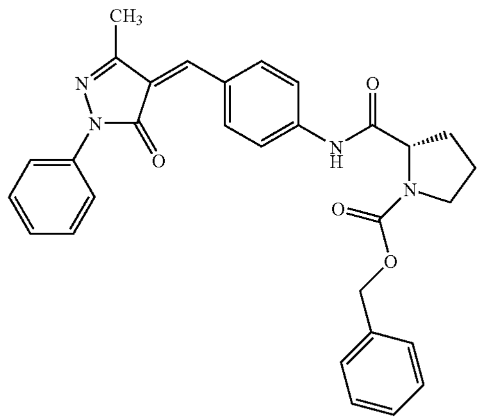 | 2-[4-(3-Methyl-5-oxo-1-phenyl-1,5-dihydro-pyrazol-4-ylidenemethyl)-phenylcarbamoyl]-pyrrolidine-1-carboxylic acid benzyl ester |
| 6006 | 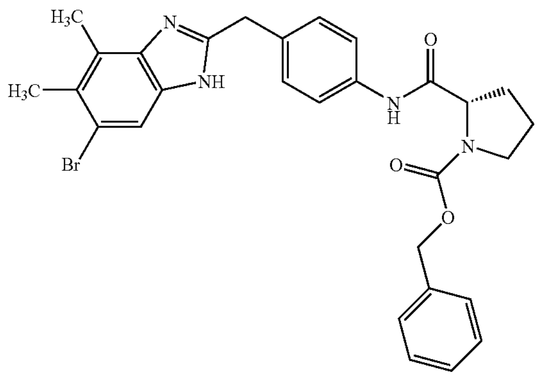 | 2-[4-(6-Bromo-4,5-dimethyl-1H-benzoimidazol-2-ylmethyl)-phenylcarbamoyl]-pyrrolidine-1-carboxylic acid benzyl ester |
| 6007 | 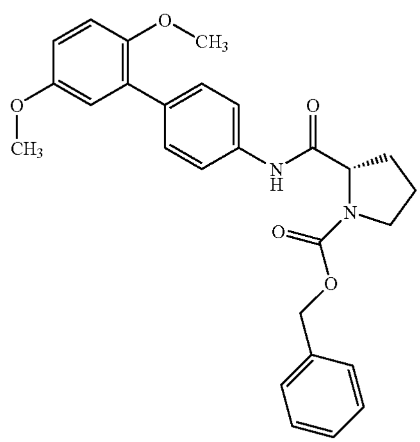 | 2-(2',5'-Dimethoxy-biphenyl-4-ylcarbamoyl)-pyrrolidine-1-carboxylic acid benzyl ester |
| 6008 | 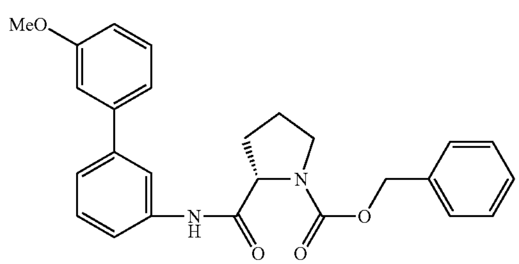 | 2-(3'-Methoxy-biphenyl-3-ylcarbamoyl)-pyrrolidine-1-carboxylic acid benzyl ester |

TABLE 1-continued

| Ex. | Compound Structure | Compound Name |
| --- | --- | --- |
| 6009 | 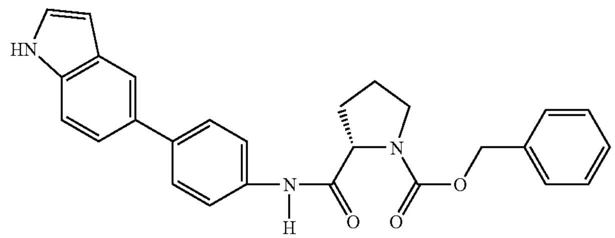 | 2-[4-(1H-Indol-5-yl)-phenylcarbamoyl]-pyrrolidine-1-carboxylic acid benzyl ester |
| 6010 | 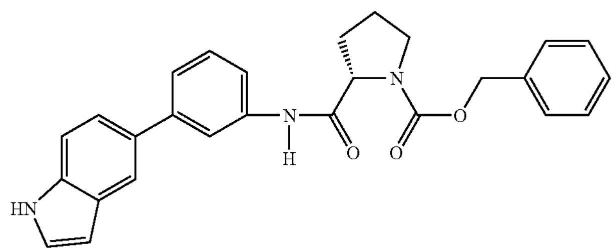 | 2-[3-(1H-Indol-5-yl)-phenylcarbamoyl]-pyrrolidine-1-carboxylic acid benzyl ester |
| 6011 | 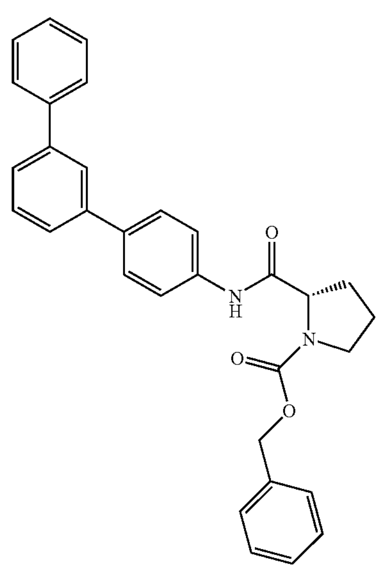 | 2-([1,1';3',1'']Terphenyl-4-ylcarbamoyl)-pyrrolidine-1-carboxylic acid benzyl ester |

TABLE 1-continued
| Ex. | Compound Structure | Compound Name |
|---|---|---|
| 6012 | 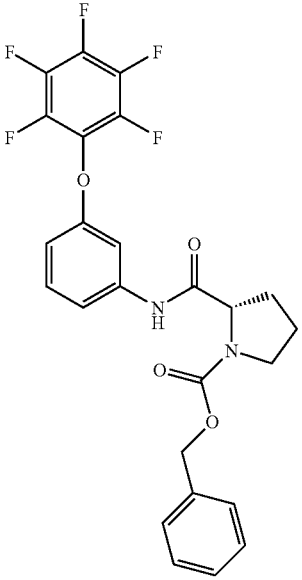 | 2-(3-Pentafluorophenyloxy-phenylcarbamoyl)-pyrrolidine-1-carboxylic acid benzyl ester |
| 6013 | 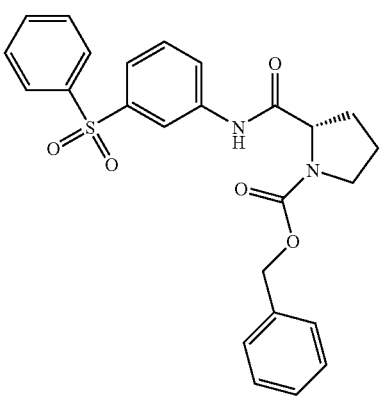 | 2-(3-Benzenesulfonyl-phenylcarbamoyl)-pyrrolidine-1-carboxylic acid benzyl ester |
| 6014 | 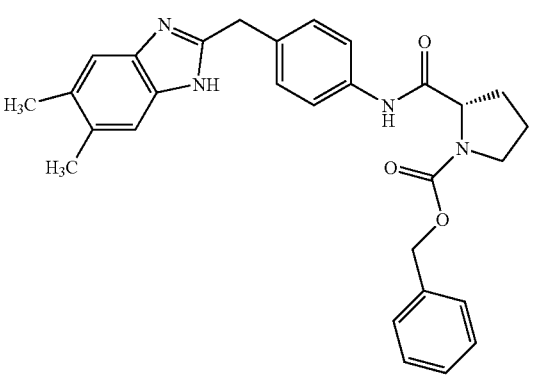 | 2-[4-(5,6-Dimethyl-1H-benzoimidazol-2-ylmethyl)-phenylcarbamoyl]-pyrrolidine-1-carboxylic acid benzyl ester |

TABLE 1-continued

| Ex. | Compound Structure | Compound Name |
|---|---|---|
| 6015 | 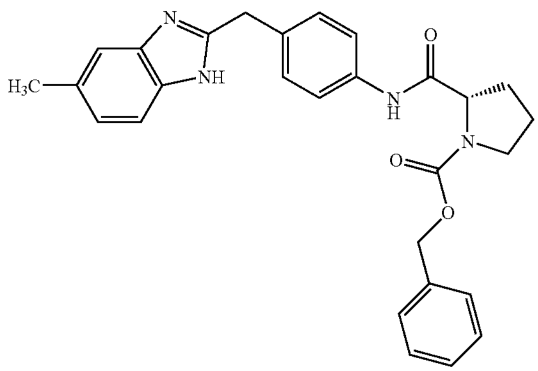 | 2-[4-(5-Methyl-1H-benzoimidazol-2-ylmethyl)-phenylcarbamoyl]-pyrrolidine-1-carboxylic acid benzyl ester |
| 6016 | 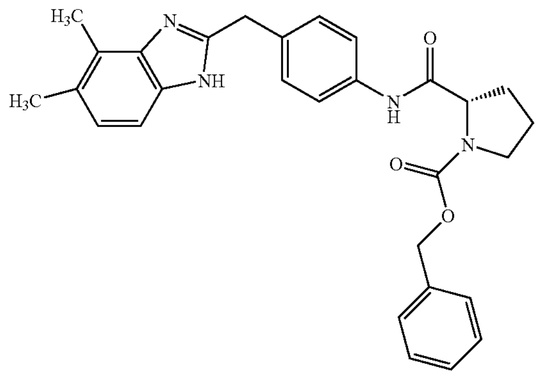 | 2-[4-(4,5-Dimethyl-1H-benzoimidazol-2-ylmethyl)-phenylcarbamoyl]-pyrrolidine-1-carboxylic acid benzyl ester |
| 6017 | 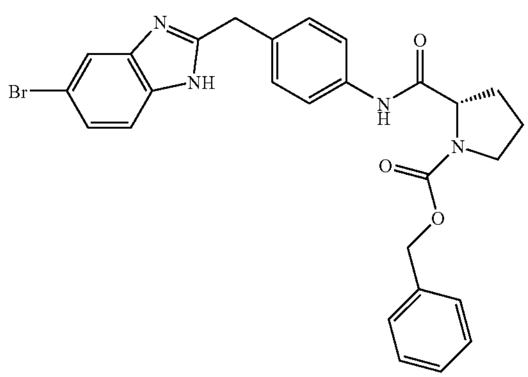 | 2-[4-(5-Bromo-1H-benzoimidazol-2-ylmethyl)-phenylcarbamoyl]-pyrrolidine-1-carboxylic acid benzyl ester |
| 6018 | 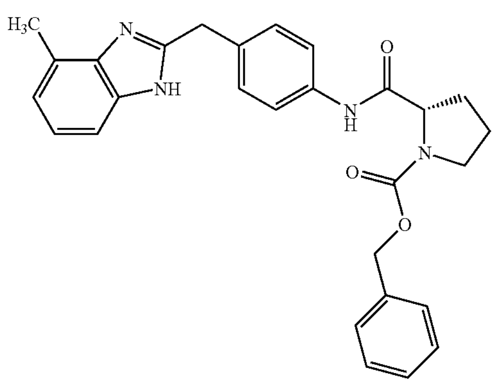 | 2-[4-(4-Methyl-1H-benzoimidazol-2-ylmethyl)-phenylcarbamoyl]-pyrrolidine-1-carboxylic acid benzyl ester |

TABLE 1-continued

| Ex. | Compound Structure | Compound Name |
|---|---|---|
| 6019 | 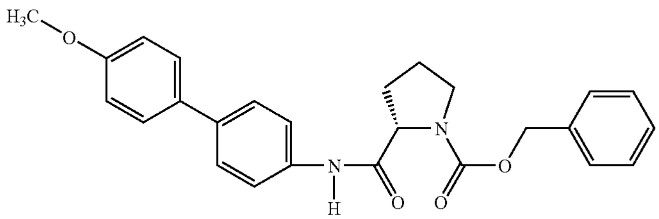 | 2-(4'-Methoxy-biphenyl-4-ylcarbamoyl)-pyrrolidine-1-carboxylic acid benzyl ester |
| 6020 | 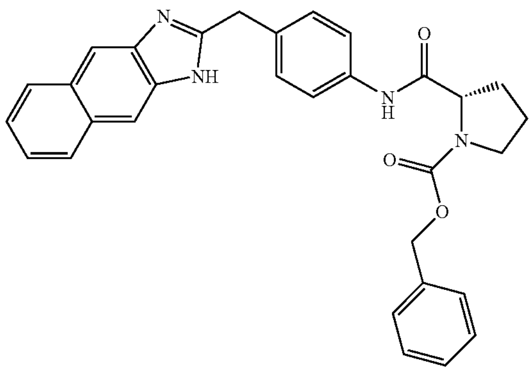 | 2-[4-(1H-Naphtho[2,3-d]imidazol-2-ylmethyl)-phenylcarbamoyl]-pyrrolidine-1-carboxylic acid benzyl ester |
| 6021 | 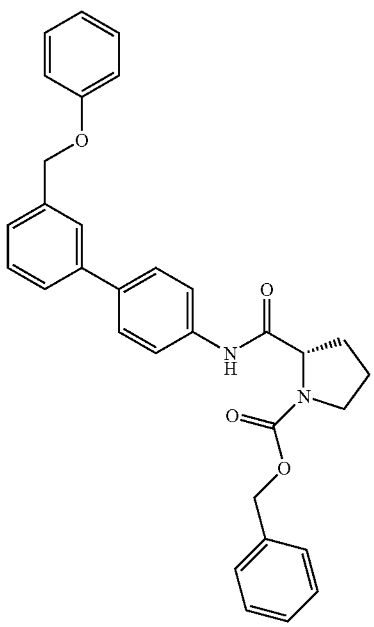 | 2-(3'-Phenoxymethyl-biphenyl-4-ylcarbamoyl)-pyrrolidine-1-carboxylic acid benzyl ester |
| 6022 | 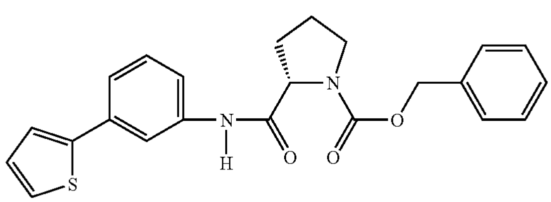 | 2-(3-Thiophen-2-yl-phenylcarbamoyl)-pyrrolidine-1-carboxylic acid benzyl ester |
| 6023 | 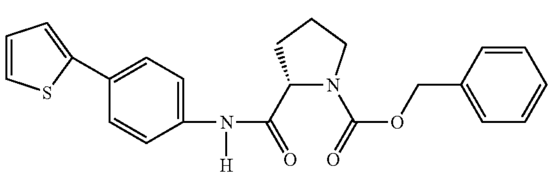 | 2-(4-Thiophen-2-yl-phenylcarbamoyl)-pyrrolidine-1-carboxylic acid benzyl ester |

TABLE 1-continued

| Ex. | Compound Structure | Compound Name |
|---|---|---|
| 6024 | 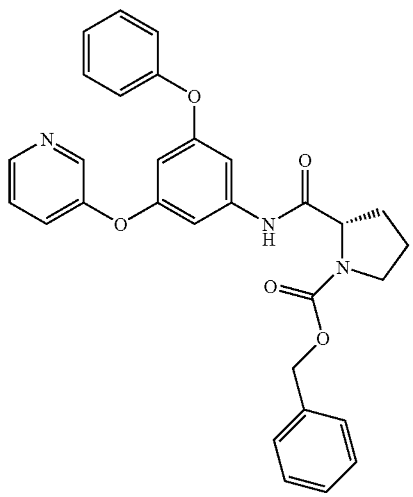 | 2-[3-Phenoxy-5-(pyridin-3-yloxy)-phenylcarbamoyl]-pyrrolidine-1-carboxylic acid benzyl ester |
| 6025 | 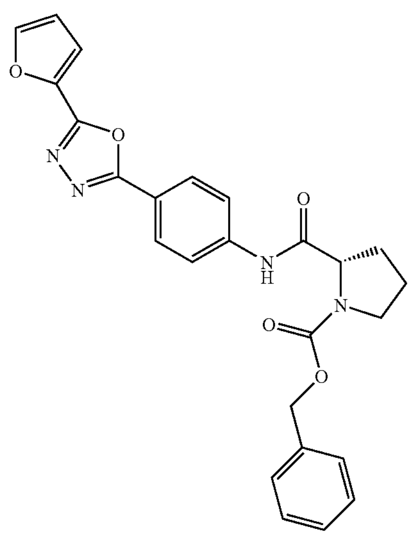 | 2-[4-(5-Furan-2-yl-[1,3,4]oxadiazol-2-yl)-phenylcarbamoyl]-pyrrolidine-1-carboxylic acid benzyl ester |
| 6026 | 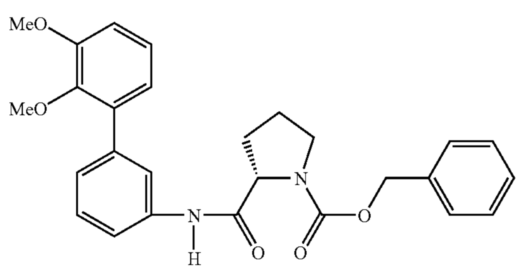 | 2-(2',3'-Dimethoxybiphenyl-3-yl-carbamoyl)-pyrrolidine-1-carboxylic acid benzyl ester |

TABLE 1-continued

| Ex. | Compound Structure | Compound Name |
| --- | --- | --- |
| 6027 | 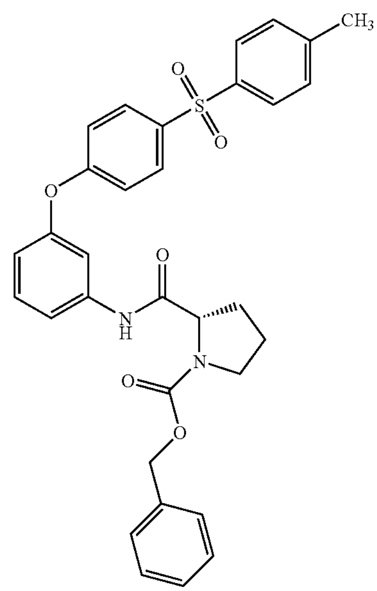 | 2-{3-[4-(Toluene-4-sulfonyl)-phenoxy]-phenylcarbamoyl}-pyrrolidine-1-carboxylic acid benzyl ester |
| 6028 | 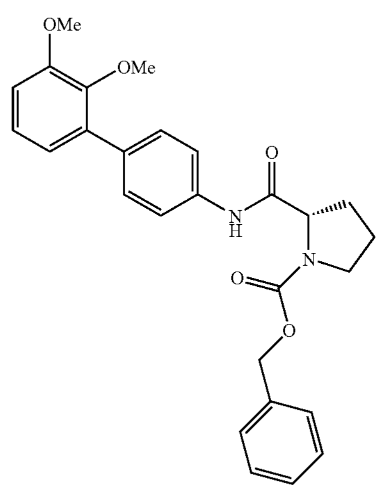 | 2-(2',3'-Dimethoxy-biphenyl-4-ylcarbamoyl)-pyrrolidine-1-carboxylic acid benzyl ester |
| 6029 | 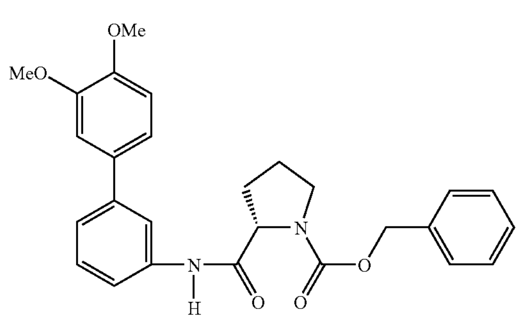 | 2-(3',4'-Dimethoxybiphenyl-3-yl-carbamoyl)-pyrrolidine-1-carboxylic acid benzyl ester |

TABLE 1-continued

| Ex. | Compound Structure | Compound Name |
|---|---|---|
| 6030 | 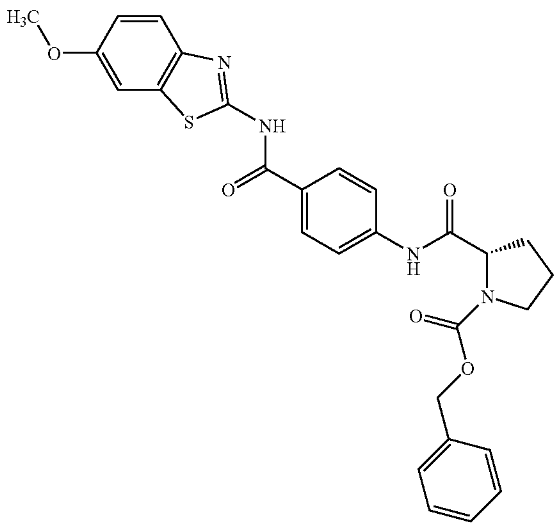 | 2-[4-(6-Methoxy-benzothiazol-2-ylcarbamoyl)-phenylcarbamoyl]-pyrrolidine-1-carboxylic acid benzyl ester |
| 6031 | 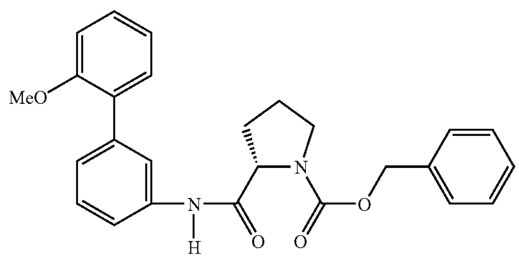 | 2-(2'-Methoxybiphenyl-3-yl-carbamoyl)-pyrrolidine-1-carboxylic acid benzyl ester |
| 6032 | 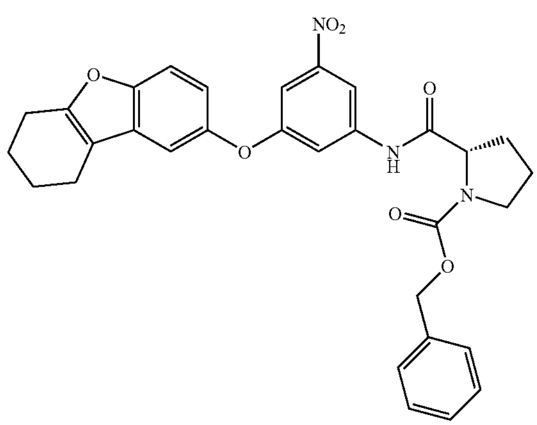 | 2-[3-Nitro-5-(6,7,8,9-tetrahydro-dibenzofuran-2-yloxy)-phenylcarbamoyl]-pyrrolidine-1-carboxylic acid benzyl ester |
| 6033 | 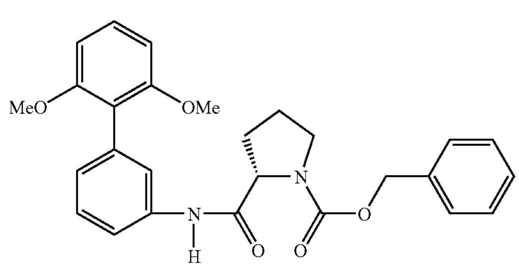 | 2-(2',6'-Dimethoxybiphenyl-3-yl-carbamoyl)-pyrrolidine-1-carboxylic acid benzyl ester |

TABLE 1-continued

| Ex. | Compound Structure | Compound Name |
| --- | --- | --- |
| 6034 | 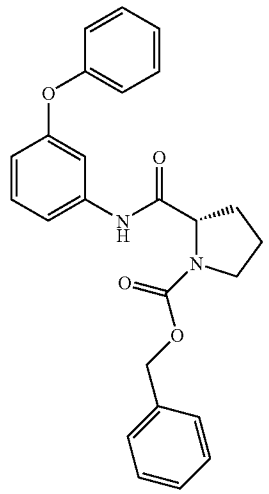 | 2-(3-Phenoxy-phenylcarbamoyl)-pyrrolidine-1-carboxylic acid benzyl ester |
| 6035 | 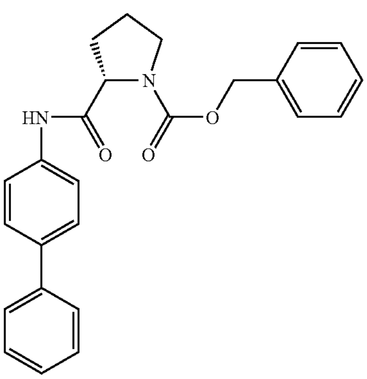 | 2-(Biphenyl-4-ylcarbamoyl)-pyrrolidine-1-carboxylic acid benzyl ester |
| 6036 | 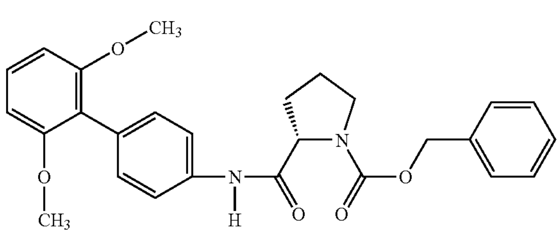 | 2-(2',6'-Dimethoxy-biphenyl-4-ylcarbamoyl)-pyrrolidine-1-carboxylic acid benzyl ester |
| 6037 | 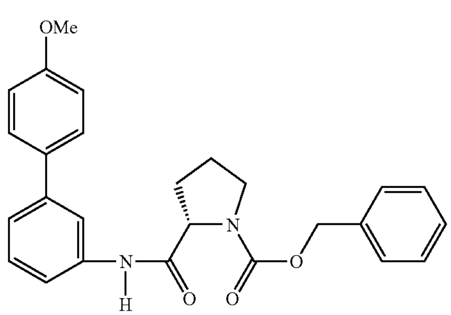 | 2-(4'-Methoxybiphenyl-3-yl-carbamoyl)-pyrrolidine-1-carboxylic acid benzyl ester |

TABLE 1-continued

| Ex. | Compound Structure | Compound Name |
|---|---|---|
| 6038 | 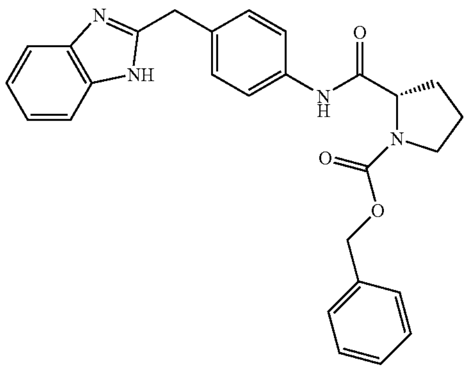 | 2-[4-(1H-Benzoimidazol-2-ylmethyl)-phenylcarbamoyl]-pyrrolidine-1-carboxylic acid benzyl ester |
| 6039 | 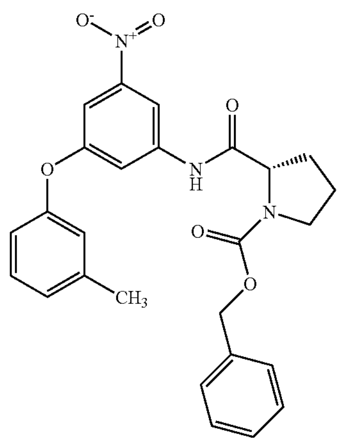 | 2-(3-Nitro-5-m-tolyloxy-phenylcarbamoyl)-pyrrolidine-1-carboxylic acid benzyl ester |
| 6040 | 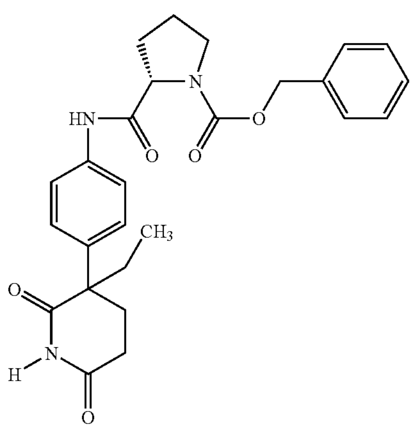 | 2-[4-(3-Ethyl-2,6-dioxo-piperidin-3-yl)-phenylcarbamoyl]-pyrrolidine-1-carboxylic acid benzyl ester |
| 6041 | 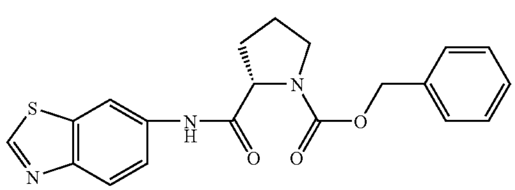 | 2-(Benzothiazol-6-ylcarbamoyl)-pyrrolidine-1-carboxylic acid benzyl ester |

TABLE 1-continued

| Ex. | Compound Structure | Compound Name |
|---|---|---|
| 6042 | 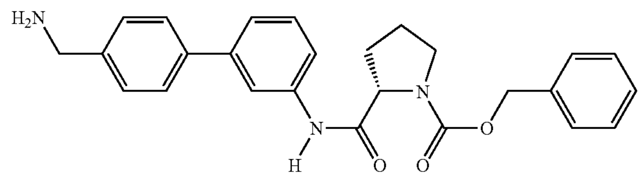 | 2-(4'-Aminomethyl-biphenyl-3-ylcarbamoyl)-pyrrolidine-1-carboxylic acid benzyl ester |
| 6043 | 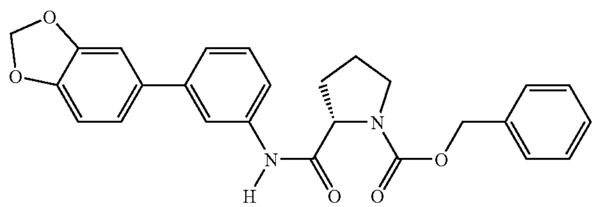 | 2-(3-Benzo[1,3]dioxol-5-yl-phenylcarbamoyl)-pyrrolidine-1-carboxylic acid benzyl ester |
| 6044 | 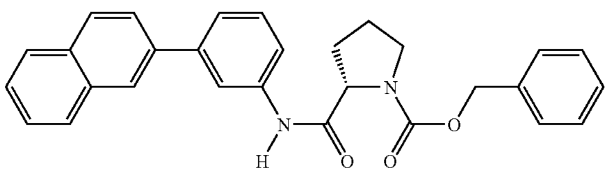 | 2-(3-Naphthalen-2-yl-phenylcarbamoyl)-pyrrolidine-1-carboxylic acid benzyl ester |
| 6045 | 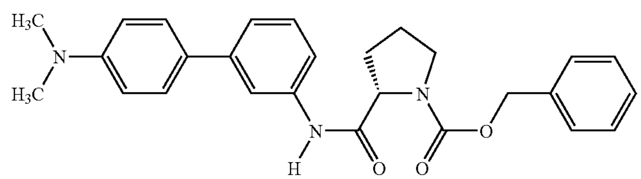 | 2-(4'-Dimethylamino-biphenyl-3-ylcarbamoyl)-pyrrolidine-1-carboxylic acid benzyl ester |
| 6046 | 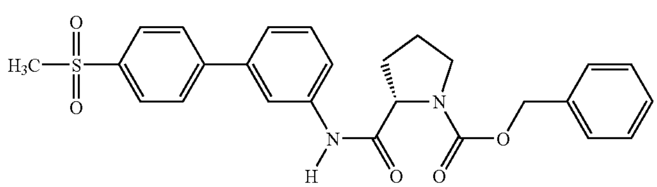 | 2-(4'-Methanesulfonyl-biphenyl-3-ylcarbamoyl)-pyrrolidine-1-carboxylic acid benzyl ester |
| 6047 | 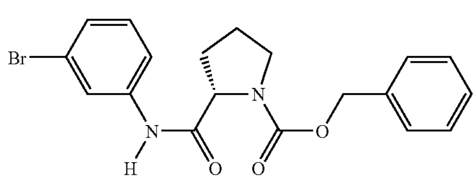 | 2-(3-Bromo-phenylcarbamoyl)-pyrrolidine-1-carboxylic acid benzyl ester |
| 6048 | 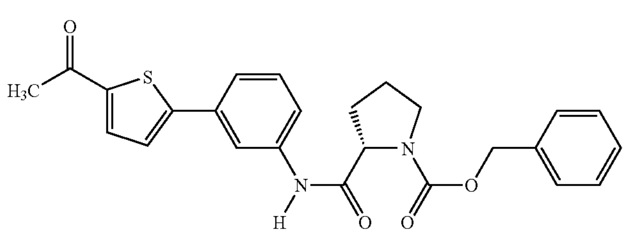 | 2-[3-(5-Acetyl-thiophen-2-yl)-phenylcarbamoyl]-pyrrolidine-1-carboxylic acid benzyl ester |

TABLE 1-continued

| Ex. | Compound Structure | Compound Name |
|---|---|---|
| 6049 | 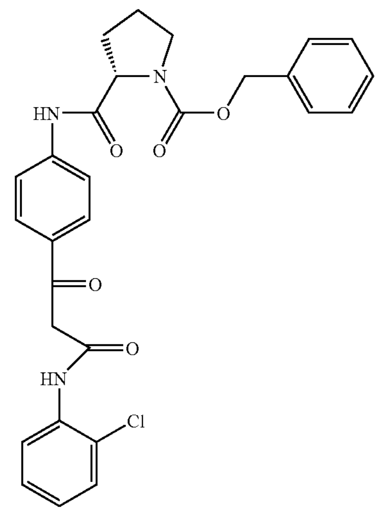 | 2-{4-[2-(2-Chloro-phenylcarbamoyl)-acetyl]-phenylcarbamoyl}-pyrrolidine-1-carboxylic acid benzyl ester |
| 6050 | 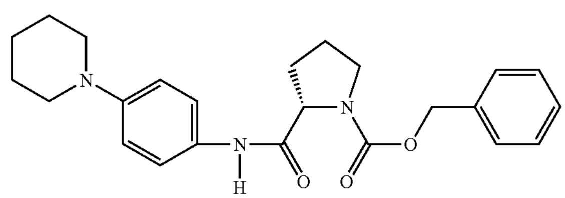 | 2-(4-Piperidin-1-yl-phenylcarbamoyl)-pyrrolidine-1-carboxylic acid benzyl ester |
| 6051 | 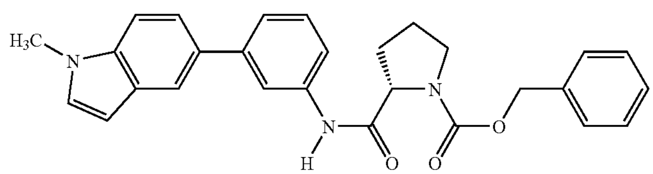 | 2-[3-(1-Methyl-1H-indol-5-yl)-phenylcarbamoyl]-pyrrolidine-1-carboxylic acid benzyl ester |
| 6052 | 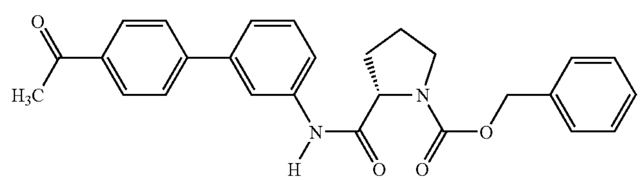 | 2-(4'-Acetyl-biphenyl-3-ylcarbamoyl)-pyrrolidine-1-carboxylic acid benzyl ester |
| 6053 | 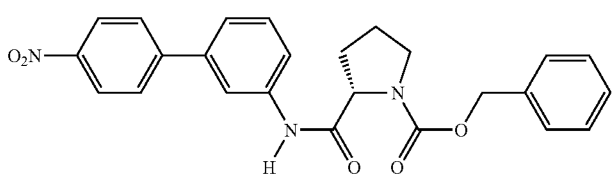 | 2-(4'-Nitro-biphenyl-3-ylcarbamoyl)-pyrrolidine-1-carboxylic acid benzyl ester |
| 6054 | 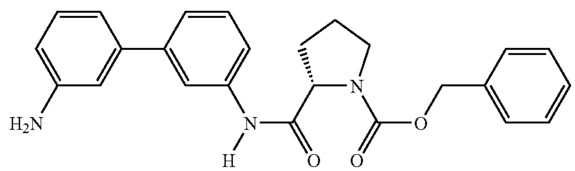 | 2-(3'-Amino-biphenyl-3-ylcarbamoyl)-pyrrolidine-1-carboxylic acid benzyl ester |

TABLE 1-continued

| Ex. | Compound Structure | Compound Name |
|---|---|---|
| 6055 | 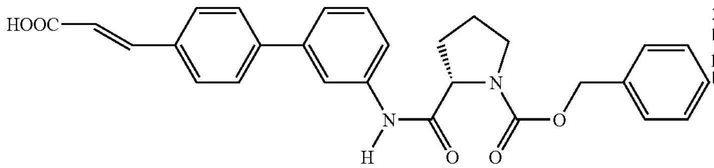 | 2-[4'-(2-Carboxy-vinyl)-biphenyl-3-ylcarbamoyl]-pyrrolidine-1-carboxylic acid benzyl ester |
| 6056 | 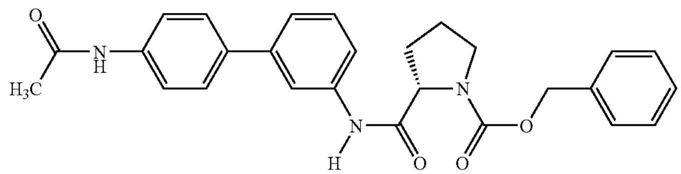 | 2-(4'-Acetylamino-biphenyl-3-ylcarbamoyl)-pyrrolidine-1-carboxylic acid benzyl ester |
| 6057 | 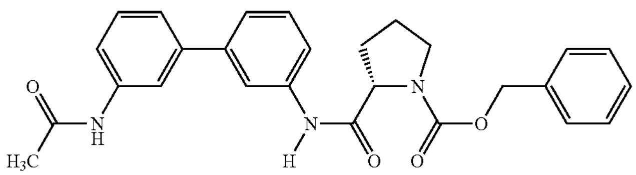 | 2-(3'-Acetylamino-biphenyl-3-ylcarbamoyl)-pyrrolidine-1-carboxylic acid benzyl ester |
| 6058 | 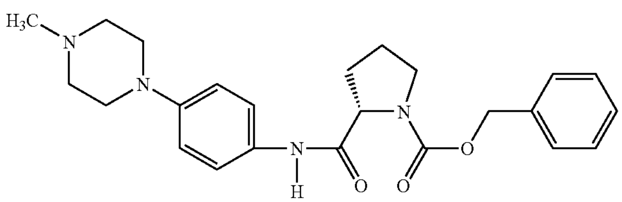 | 2-[4-(4-Methyl-piperazin-1-yl)-phenylcarbamoyl]-pyrrolidine-1-carboxylic acid benzyl ester |
| 6059 | 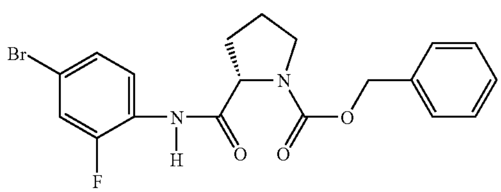 | 2-(4-Bromo-2-fluoro-phenylcarbamoyl)-pyrrolidine-1-carboxylic acid benzyl ester |
| 6060 | 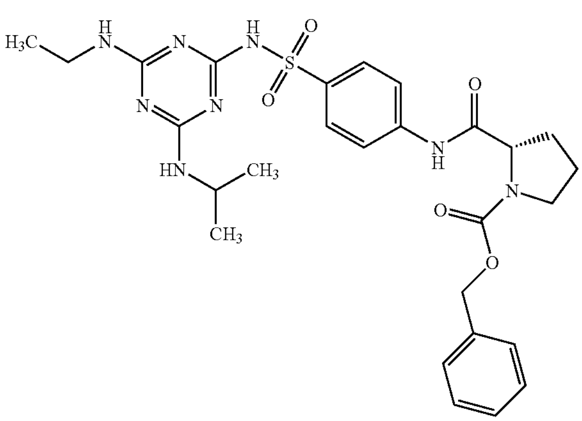 | 2-[4-(4-Ethylamino-6-isopropylamino-[1,3,5]triazin-2-ylsulfamoyl)-phenylcarbamoyl]-pyrrolidine-1-carboxylic acid benzyl ester |

TABLE 1-continued

| Ex. | Compound Structure | Compound Name |
|---|---|---|
| 6061 | 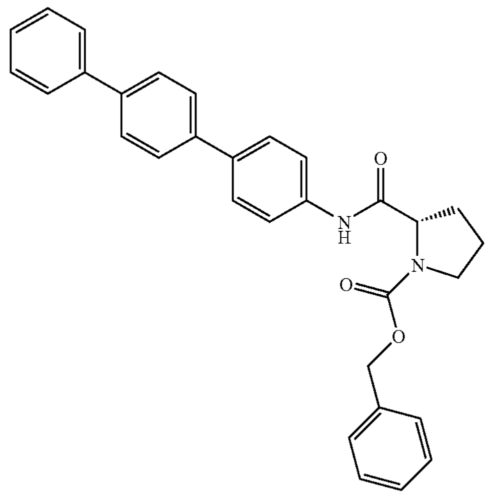 | 2-([1,1';4',1"]Terphenyl-4-ylcarbamoyl)-pyrrolidine-1-carboxylic acid benzyl ester |
| 6062 | 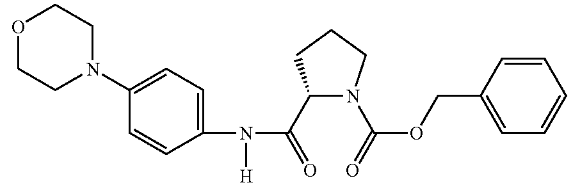 | 2-(4-Morpholin-4-yl-phenylcarbamoyl)-pyrrolidine-1-carboxylic acid benzyl ester |
| 6063 | 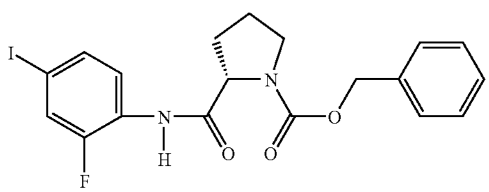 | 2-(2-Fluoro-4-iodo-phenylcarbamoyl)-pyrrolidine-1-carboxylic acid benzyl ester |
| 6064 | 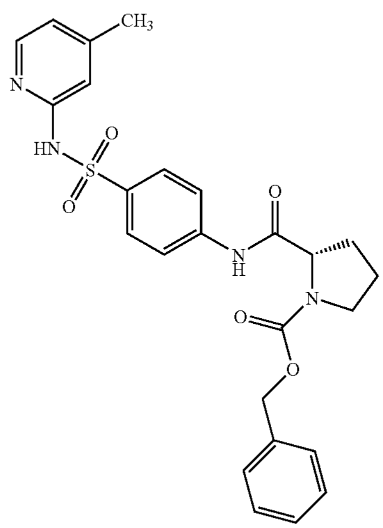 | 2-[4-(4-Methyl-pyridin-2-ylsulfamoyl)-phenylcarbamoyl]-pyrrolidine-1-carboxylic acid benzyl ester |

TABLE 1-continued

| Ex. | Compound Structure | Compound Name |
|---|---|---|
| 6065 | 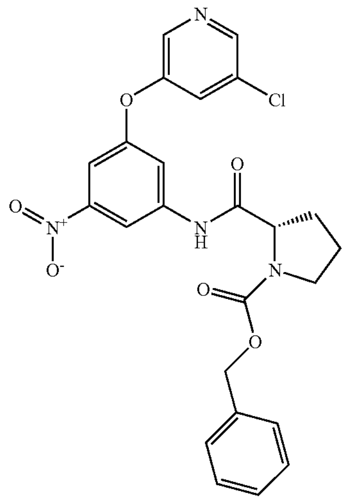 | 2-[3-(5-Chloro-pyridin-3-yloxy)-5-nitro-phenylcarbamoyl]-pyrrolidine-1-carboxylic acid benzyl ester |
| 6066 | 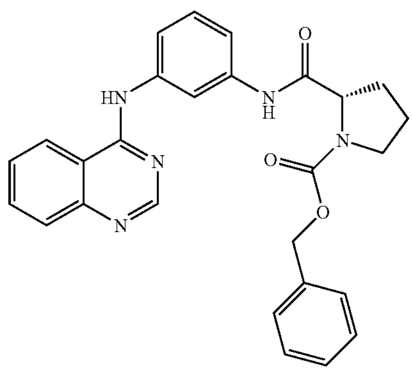 | 2-[3-(Quinazolin-4-ylamino)-phenylcarbamoyl]-pyrrolidine-1-carboxylic acid benzyl ester |
| 6067 | 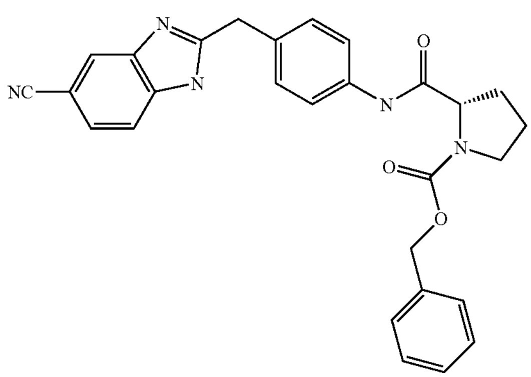 | 2-[4-(5-Cyano-1H-benzoimidazol-2-ylmethyl)-phenylcarbamoyl]-pyrrolidine-1-carboxylic acid benzyl ester |
| 6068 | 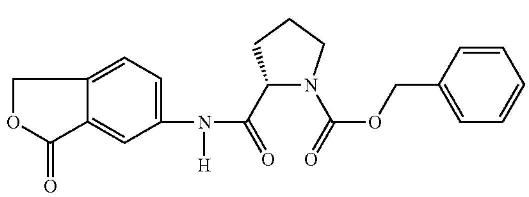 | 2-(3-Oxo-1,3-dihydro-isobenzofuran-5-ylcarbamoyl)-pyrrolidine-1-carboxylic acid benzyl ester |

TABLE 1-continued

| Ex. | Compound Structure | Compound Name |
| --- | --- | --- |
| 6069 | 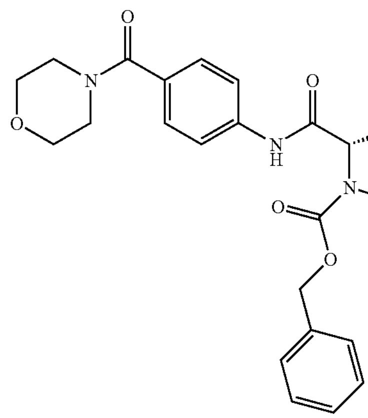 | 2-[4-(Morpholine-4-carbonyl)-phenylcarbamoyl]-pyrrolidine-1-carboxylic acid benzyl ester |
| 6070 | 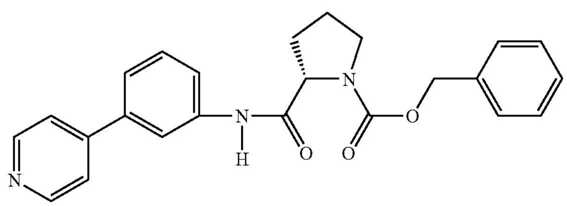 | 2-(3-Pyridin-4-yl-phenylcarbamoyl)-pyrrolidine-1-carboxylic acid benzyl ester |
| 6071 | 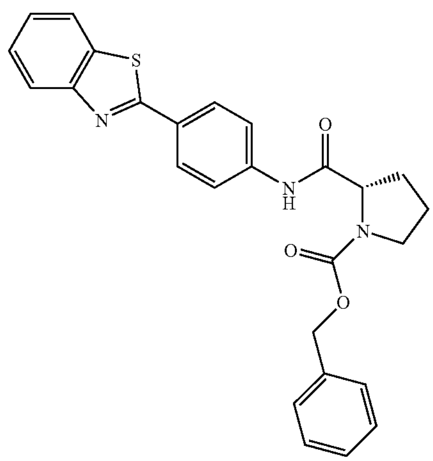 | 2-(4-Benzothiazol-2-yl-phenylcarbamoyl)-pyrrolidine-1-carboxylic acid benzyl ester |
| 6072 | 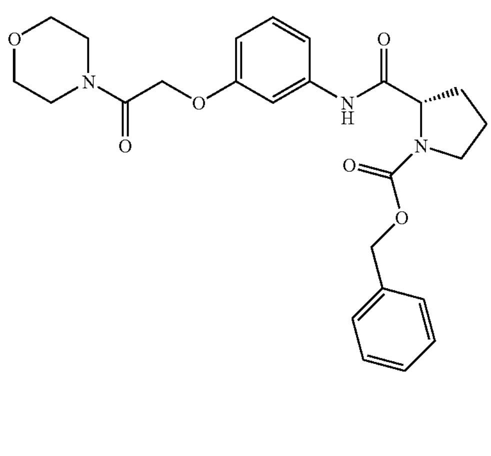 | 2-[3-(2-Morpholin-4-yl-2-oxo-ethoxy)-phenylcarbamoyl]-pyrrolidine-1-carboxylic acid benzyl ester |

TABLE 1-continued

| Ex. | Compound Structure | Compound Name |
| --- | --- | --- |
| 6073 | 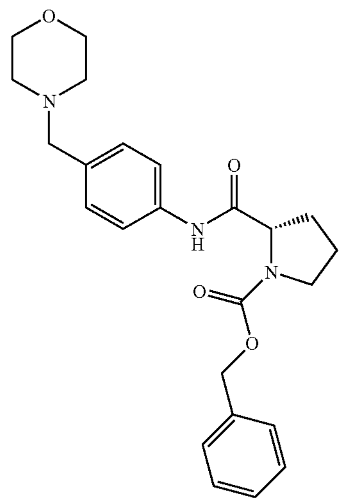 | 2-(4-Morpholin-4-ylmethyl-phenylcarbamoyl)-pyrrolidine-1-carboxylic acid benzyl ester |
| 6074 | 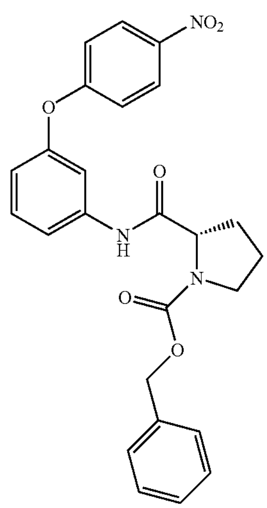 | 2-[3-(4-Nitro-phenoxy)-phenylcarbamoyl]-pyrrolidine-1-carboxylic acid benzyl ester |
| 6075 | 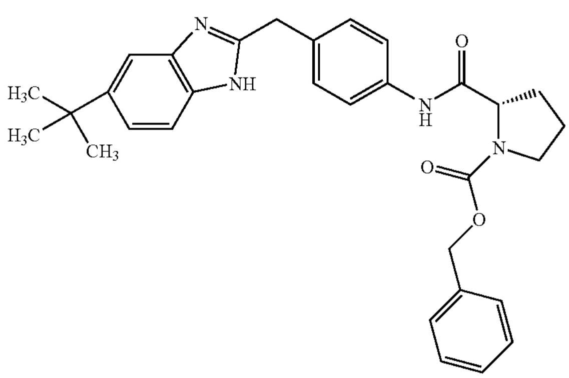 | 2-[4-(5-tert-Butyl-1H-benzoimidazol-2-ylmethyl)-phenylcarbamoyl]-pyrrolidine-1-carboxylic acid benzyl ester |
| 6076 | 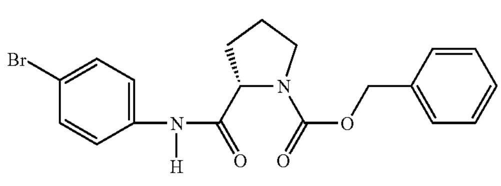 | 2-(4-Bromo-phenylcarbamoyl)-pyrrolidine-1-carboxylic acid benzyl ester |

TABLE 1-continued

| Ex. | Compound Structure | Compound Name |
| --- | --- | --- |
| 6077 | 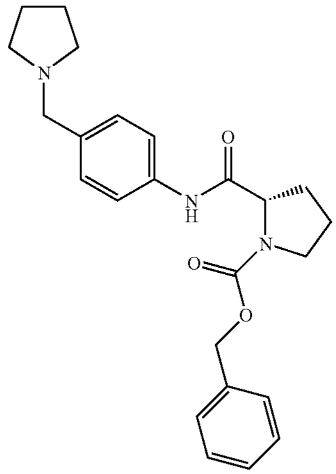 | 2-(4-Pyrrolidin-1-ylmethyl-phenylcarbamoyl)-pyrrolidine-1-carboxylic acid benzyl ester |
| 6078 | 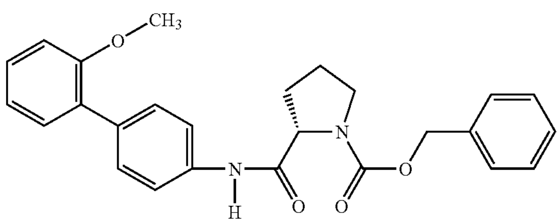 | 2-(2'-Methoxy-biphenyl-4-ylcarbamoyl)-pyrrolidine-1-carboxylic acid benzyl ester |
| 6079 | 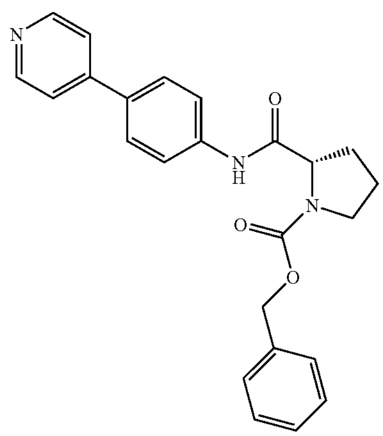 | 2-(4-Pyridin-4-yl-phenylcarbamoyl)-pyrrolidine-1-carboxylic acid benzyl ester |
| 6080 | 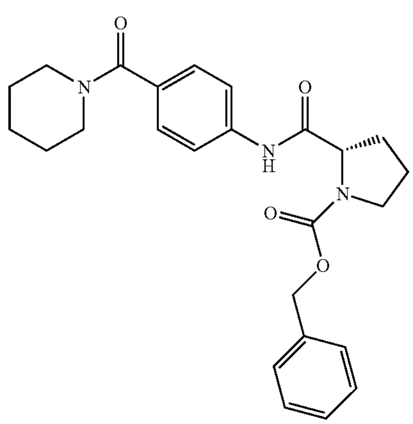 | 2-[4-(Piperidine-1-carbonyl)-phenylcarbamoyl]-pyrrolidine-1-carboxylic acid benzyl ester |

TABLE 1-continued

| Ex. | Compound Structure | Compound Name |
| --- | --- | --- |
| 6081 | 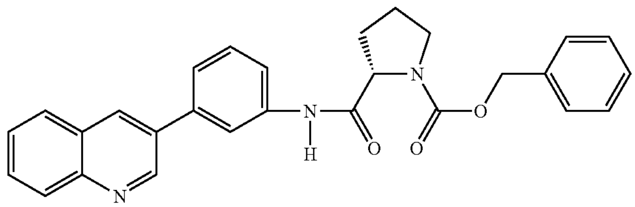 | 2-(3-Quinolin-3-yl-phenylcarbamoyl)-pyrrolidine-1-carboxylic acid benzyl ester |
| 6082 | 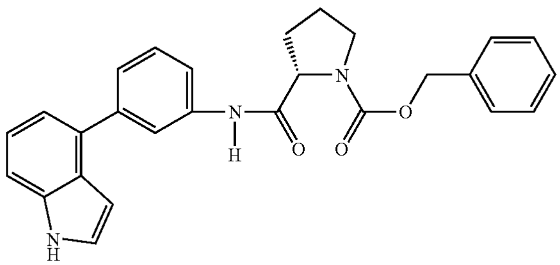 | 2-[3-(1H-Indol-4-yl)-phenylcarbamoyl]-pyrrolidine-1-carboxylic acid benzyl ester |
| 6083 | 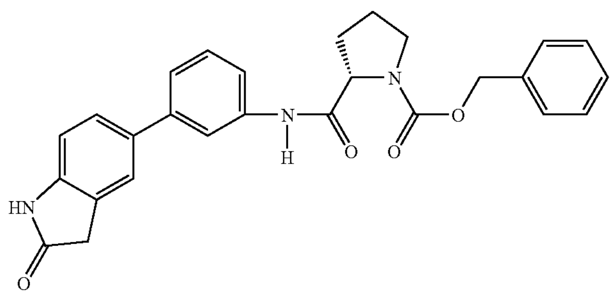 | 2-[3-(2-Oxo-2,3-dihydro-1H-indol-5-yl)-phenylcarbamoyl]-pyrrolidine-1-carboxylic acid benzyl ester |
| 6084 | 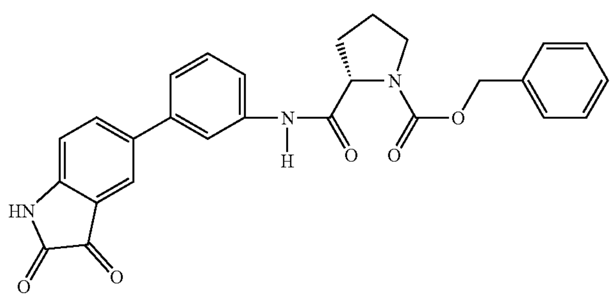 | 2-[3-(2,3-Dioxo-2,3-dihydro-1H-indol-5-yl)-phenylcarbamoyl]-pyrrolidine-1-carboxylic acid benzyl ester |
| 6085 | 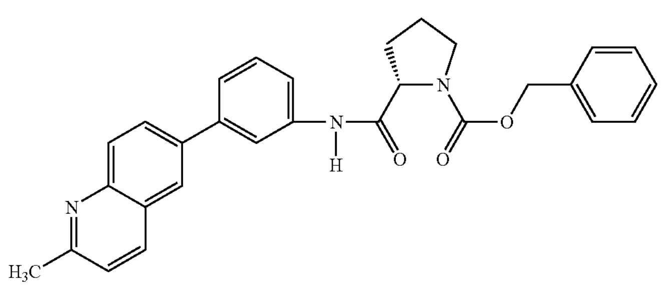 | 2-[3-(2-Methyl-quinolin-6-yl)-phenylcarbamoyl]-pyrrolidine-1-carboxylic acid benzyl ester |
| 6086 | 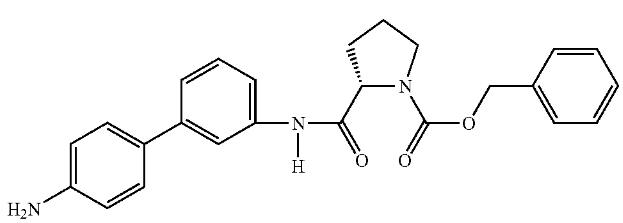 | 2-(4'-Amino-biphenyl-3-ylcarbamoyl)-pyrrolidine-1-carboxylic acid benzyl ester |

TABLE 1-continued

| Ex. | Compound Structure | Compound Name |
|---|---|---|
| 6087 | 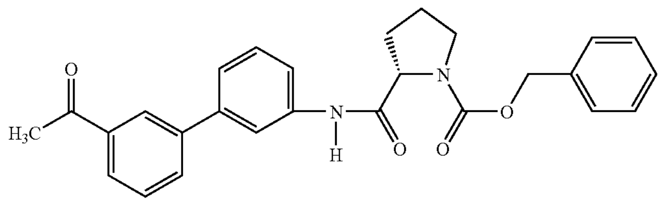 | 2-(3'-Acetyl-biphenyl-3-ylcarbamoyl)-pyrrolidine-1-carboxylic acid benzyl ester |
| 6088 | 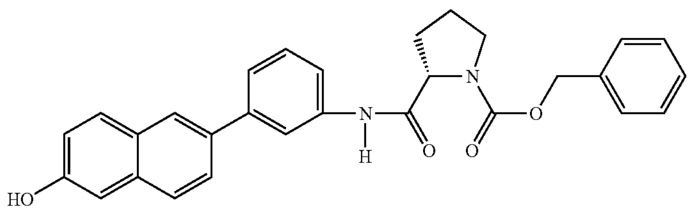 | 2-[3-(6-Hydroxy-naphthalen-2-yl)-phenylcarbamoyl]-pyrrolidine-1-carboxylic acid benzyl ester |
| 6089 | 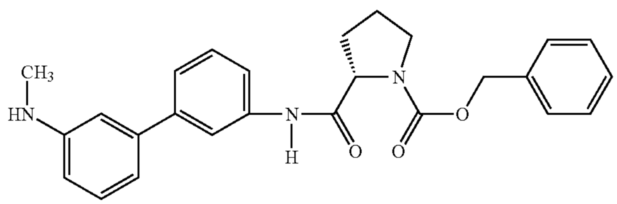 | 2-(3'-Methylamino-biphenyl-3-ylcarbamoyl)-pyrrolidine-1-carboxylic acid benzyl ester |
| 6090 | 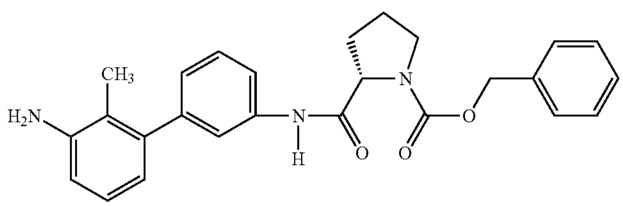 | 2-(3'-Amino-2'-methyl-biphenyl-3-ylcarbamoyl)-pyrrolidine-1-carboxylic acid benzyl ester |
| 6091 | 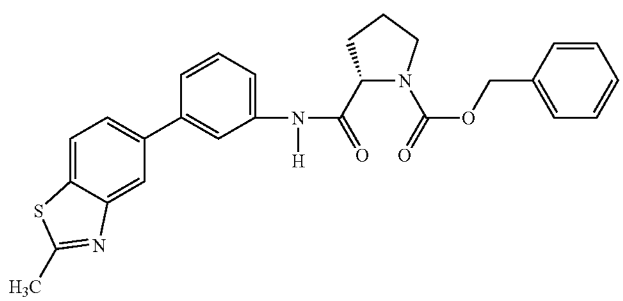 | 2-[3-(2-Methyl-benzothiazol-5-yl)-phenylcarbamoyl]-pyrrolidine-1-carboxylic acid benzyl ester |
| 6092 | 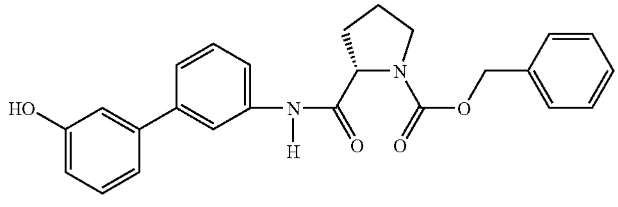 | 2-(3'-Hydroxy-biphenyl-3-ylcarbamoyl)-pyrrolidine-1-carboxylic acid benzyl ester |
| 6093 | 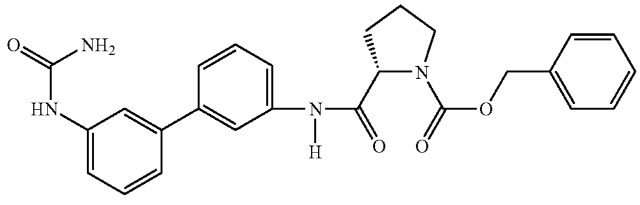 | 2-(3'-Ureido-biphenyl-3-ylcarbamoyl)-pyrrolidine-1-carboxylic acid benzyl ester |

TABLE 1-continued

| Ex. | Compound Structure | Compound Name |
|---|---|---|
| 6094 | 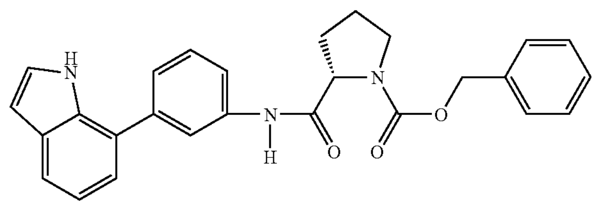 | 2-[3-(1H-Indol-7-yl)-phenylcarbamoyl]-pyrrolidine-1-carboxylic acid benzyl ester |
| 6095 | 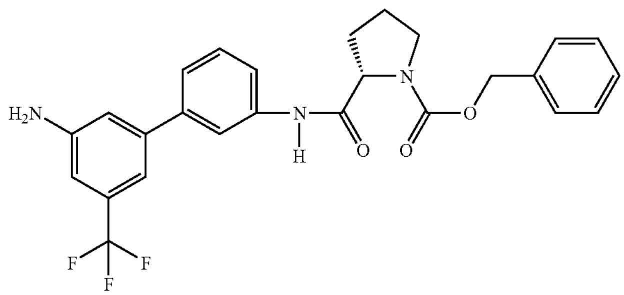 | 2-(3'-Amino-5'-trifluoromethyl-biphenyl-3-ylcarbamoyl)-pyrrolidine-1-carboxylic acid benzyl ester |
| 6096 | 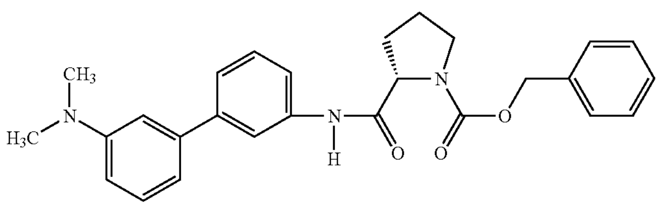 | 2-(3'-Dimethylamino-biphenyl-3-ylcarbamoyl)-pyrrolidine-1-carboxylic acid benzyl ester |
| 6097 | 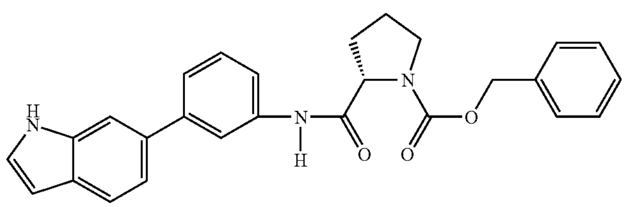 | 2-[3-(1H-Indol-6-yl)-phenylcarbamoyl]-pyrrolidine-1-carboxylic acid benzyl ester |
| 6201 | 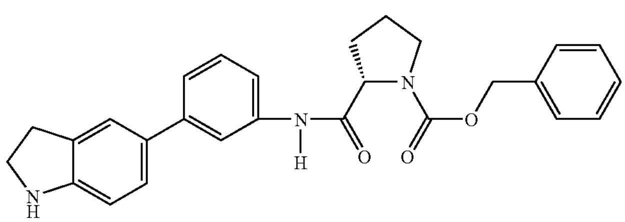 | 2-[3-(2,3-Dihydro-1H-indol-5-yl)-phenylcarbamoyl]-pyrrolidine-1-carboxylic acid benzyl ester |
| 6202 | 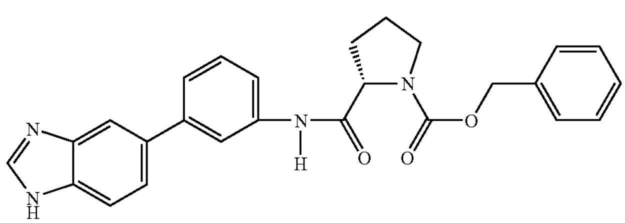 | 2-[3-(1H-Benzoimidazol-5-yl)-phenylcarbamoyl]-pyrrolidine-1-carboxylic acid benzyl ester |

TABLE 1-continued

| Ex. | Compound Structure | Compound Name |
|---|---|---|
| 6203 | 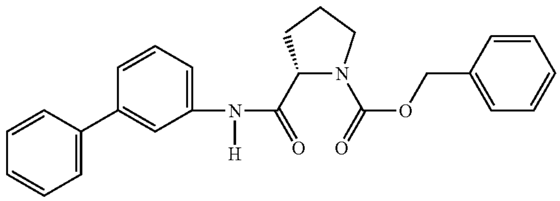 | 2-(Biphenyl-3-ylcarbamoyl)-pyrrolidine-1-carboxylic acid benzyl ester |
| 6204 | 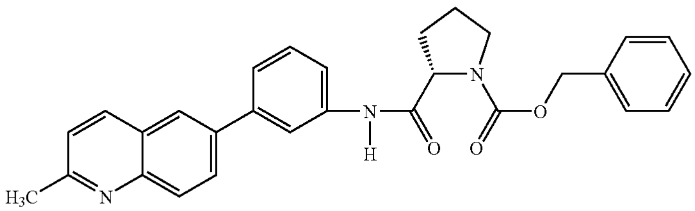 | 2-[3-(2-Methyl-quinolin-6-yl)-phenylcarbamoyl]-pyrrolidine-1-carboxylic acid benzyl ester |
| 6205 | 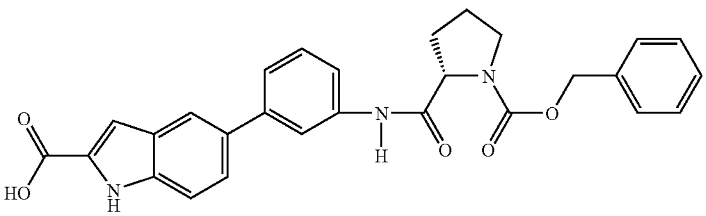 | 5-{3-[(1-Benzyloxycarbonyl-pyrrolidine-2-carbonyl)-amino]-phenyl}-1H-indole-2-carboxylic acid |
| 6206 | 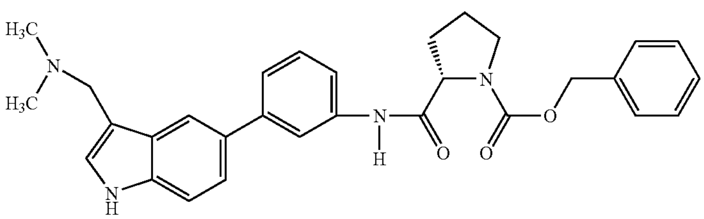 | 2-[3-(3-Dimethylaminomethyl-1H-indol-5-yl)-phenylcarbamoyl]-pyrrolidine-1-carboxylic acid benzyl ester |
| 6207 | 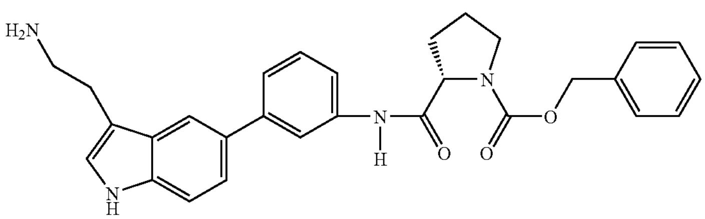 | 2-{3-[3-(2-Amino-ethyl)-1H-indol-5-yl]-phenylcarbamoyl}-pyrrolidine-1-carboxylic acid benzyl ester |
| 6208 | 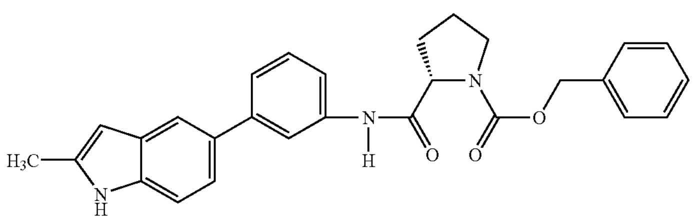 | 2-[3-(2-Methyl-1H-indol-5-yl)-phenylcarbamoyl]-pyrrolidine-1-carboxylic acid benzyl ester |
| 6209 | 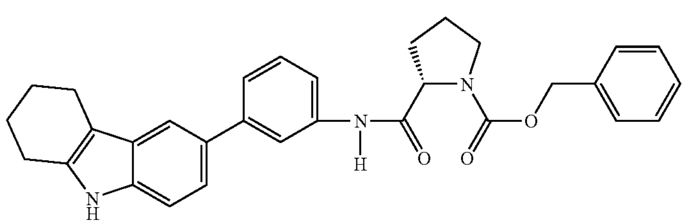 | 2-[3-(6,7,8,9-Tetrahydro-5H-carbazol-3-yl)-phenylcarbamoyl]-pyrrolidine-1-carboxylic acid benzyl ester |

TABLE 1-continued

| Ex. | Compound Structure | Compound Name |
|---|---|---|
| 6210 | 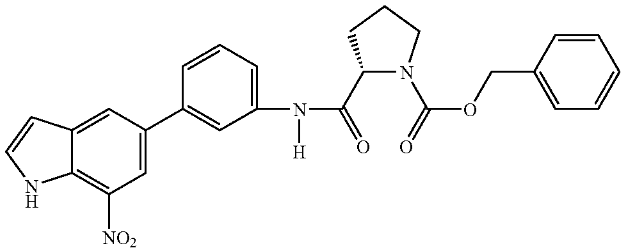 | 2-[3-(7-Nitro-1H-indol-5-yl)-phenylcarbamoyl]-pyrrolidine-1-carboxylic acid benzyl ester |
| 6211 | 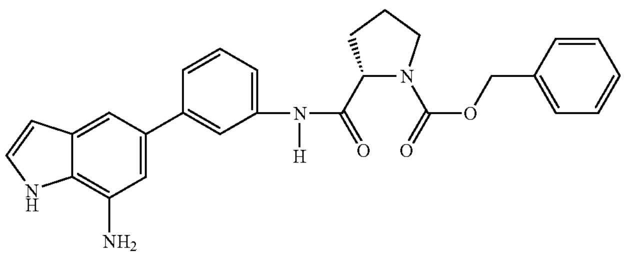 | 2-[3-(7-Amino-1H-indol-5-yl)-phenylcarbamoyl]-pyrrolidine-1-carboxylic acid benzyl ester |
| 6212 | 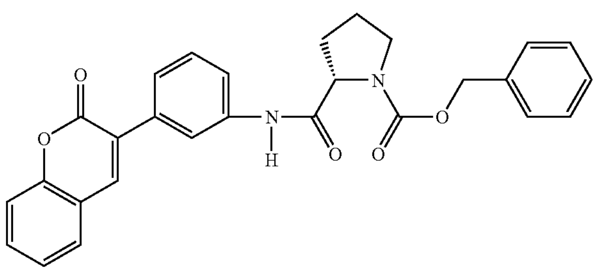 | 2-[3-(2-Oxo-2H-chromen-3-yl)-phenylcarbamoyl]-pyrrolidine-1-carboxylic acid benzyl ester |
| 6213 | 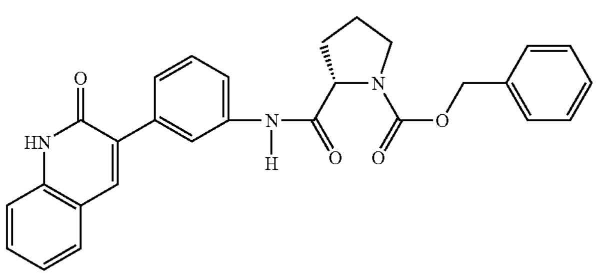 | 2-[3-(2-Oxo-1,2-dihydro-quinolin-3-yl)-phenylcarbamoyl]-pyrrolidine-1-carboxylic acid benzyl ester |
| 6214 | 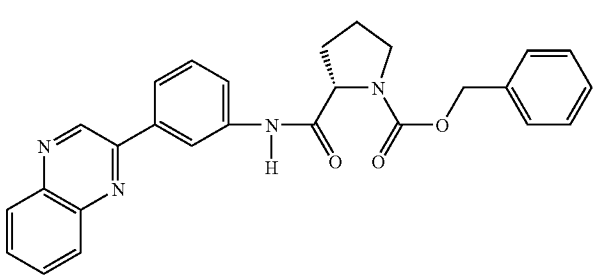 | 2-(3-Quinoxalin-2-yl-phenylcarbamoyl)-pyrrolidine-1-carboxylic acid benzyl ester |

TABLE 1-continued

| Ex. | Compound Structure | Compound Name |
|---|---|---|
| 6215 | 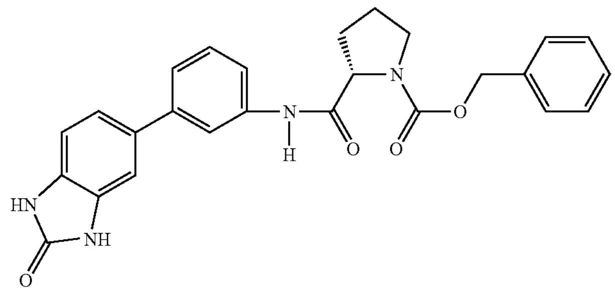 | 2-[3-(2-Oxo-2,3-dihydro-1H-benzoimidazol-5-yl)-phenylcarbamoyl]-pyrrolidine-1-carboxylic acid benzyl ester |
| 6216 | 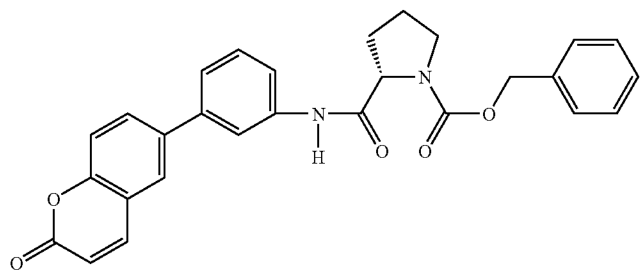 | 2-[3-(2-Oxo-2H-chromen-6-yl)-phenylcarbamoyl]-pyrrolidine-1-carboxylic acid benzyl ester |
| 6217 | 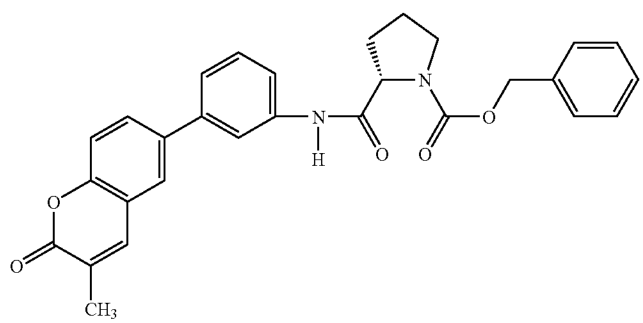 | 2-[3-(3-Methyl-2-oxo-2H-chromen-6-yl)-phenylcarbamoyl]-pyrrolidine-1-carboxylic acid benzyl ester |
| 6218 | 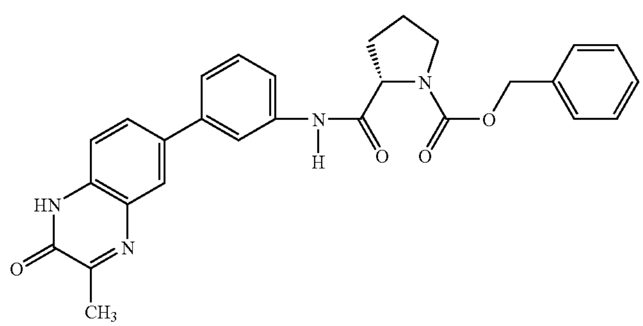 | 2-[3-(3-Methyl-2-oxo-1,2-dihydro-quinoxalin-6-yl)-phenylcarbamoyl]-pyrrolidine-1-carboxylic acid benzyl ester |
| 6219 | 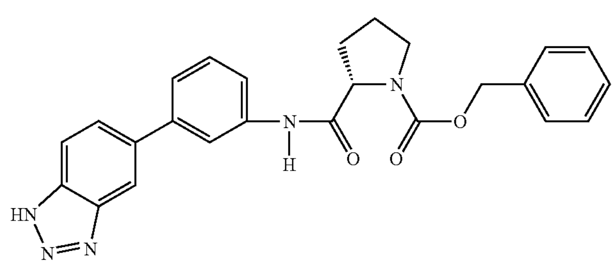 | 2-[3-(1H-Benzotriazol-5-yl)-phenylcarbamoyl]-pyrrolidine-1-carboxylic acid benzyl ester |

TABLE 1-continued

| Ex. | Compound Structure | Compound Name |
|---|---|---|
| 6220 | 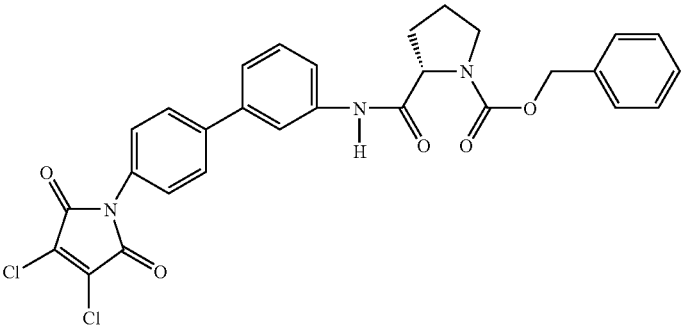 | 2-[4'-(3,4-Dichloro-2,5-dioxo-2,5-dihydro-pyrrol-1-yl)-biphenyl-3-ylcarbamoyl]-pyrrolidine-1-carboxylic acid benzyl ester |
| 6221 | 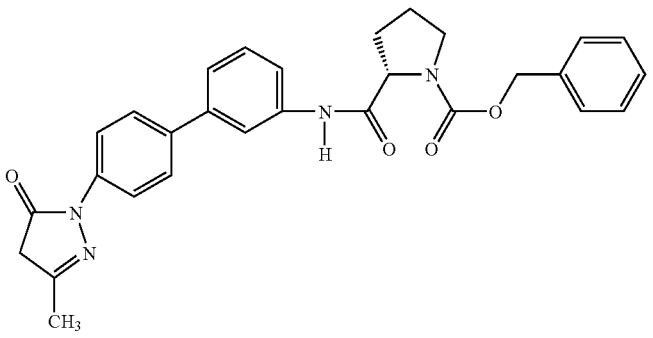 | 2-[4'-(3-Methyl-5-oxo-4,5-dihydro-pyrazol-1-yl)-biphenyl-3-ylcarbamoyl]-pyrrolidine-1-carboxylic acid benzyl ester |
| 6222 | 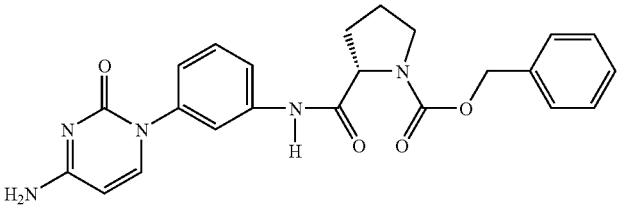 | 2-[3-(4-Amino-2-oxo-2H-pyrimidin-1-yl)-phenylcarbamoyl]-pyrrolidine-1-carboxylic acid benzyl ester |
| 6223 | 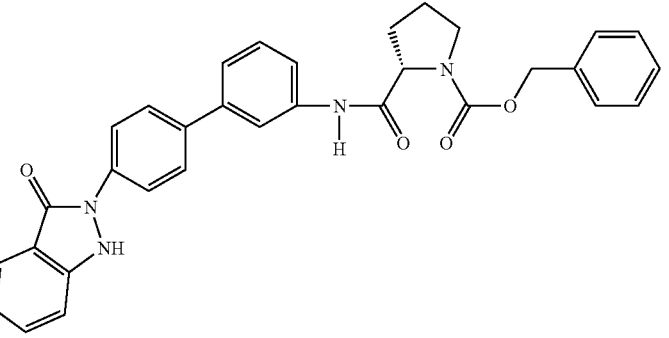 | 2-[4'-(3-Oxo-1,3-dihydro-indazol-2-yl)-biphenyl-3-ylcarbamoyl]-pyrrolidine-1-carboxylic acid benzyl ester |
| 6224 | 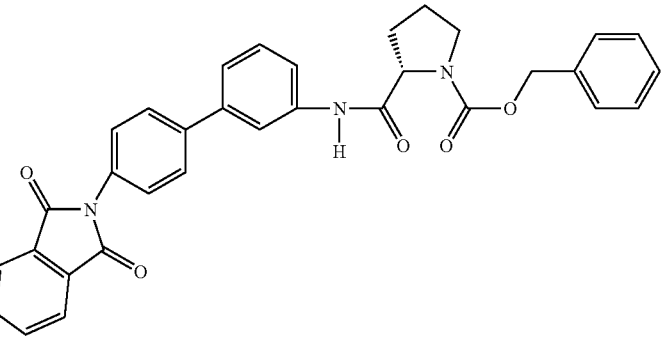 | 2-[4'-(1,3-Dioxo-1,3-dihydro-isoindol-2-yl)-biphenyl-3-ylcarbamoyl]-pyrrolidine-1-carboxylic acid benzyl ester |

TABLE 1-continued

| Ex. | Compound Structure | Compound Name |
|---|---|---|
| 6225 | 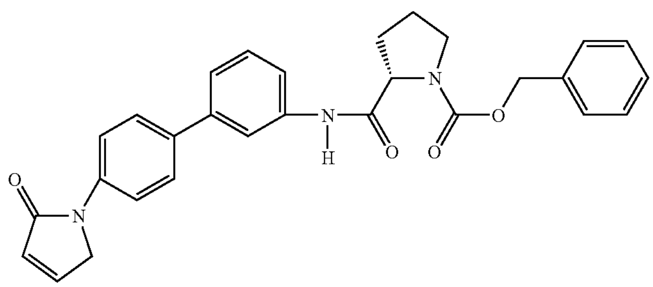 | 2-[4'-(2-Oxo-2,5-dihydro-pyrrol-1-yl)-biphenyl-3-ylcarbamoyl]-pyrrolidine-1-carboxylic acid benzyl ester |
| 6226 | 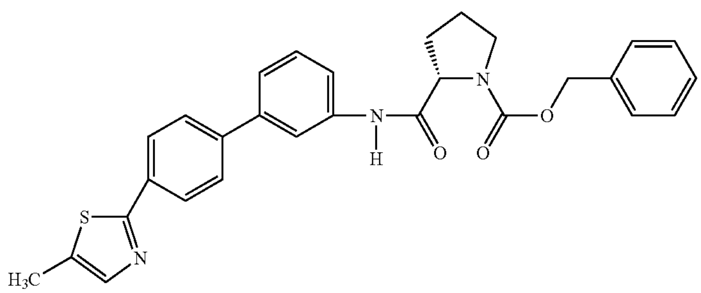 | 2-[4'-(5-Methyl-thiazol-2-yl)-biphenyl-3-ylcarbamoyl]-pyrrolidine-1-carboxylic acid benzyl ester |
| 6227 | 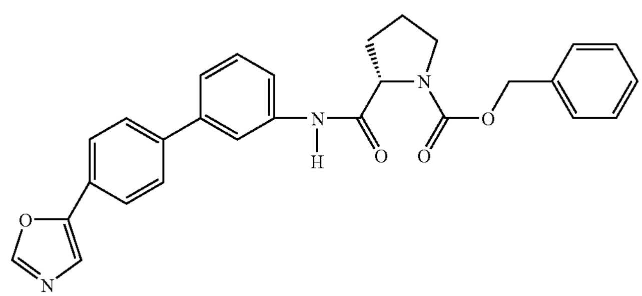 | 2-(4'-Oxazol-5-yl-biphenyl-3-ylcarbamoyl)-pyrrolidine-1-carboxylic acid benzyl ester |
| 6228 | 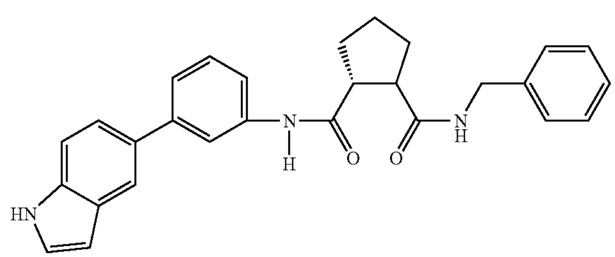 | Cyclopentane-1,2-dicarboxylic acid 1-benzylamide 2-{[3-(1H-indol-5-yl)-phenyl]-amide} |
| 6229 | 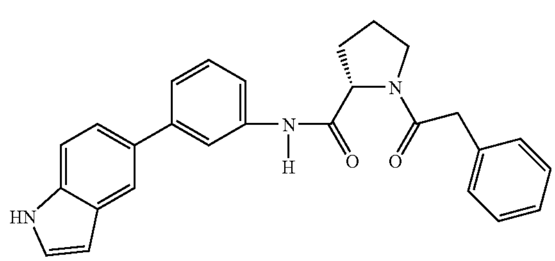 | 1-Phenylacetyl-pyrrolidine-2-carboxylic acid [3-(1H-indol-5-yl)-phenyl]-amide |

TABLE 1-continued

| Ex. | Compound Structure | Compound Name |
|---|---|---|
| 6229 | 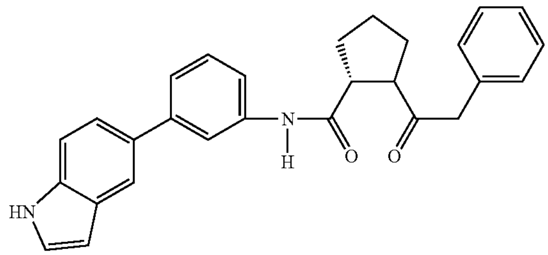 | 2-Phenylacetyl-cyclopentanecarboxylic acid [3-(1H-indol-5-yl)-phenyl]-amide |
| 6231 | 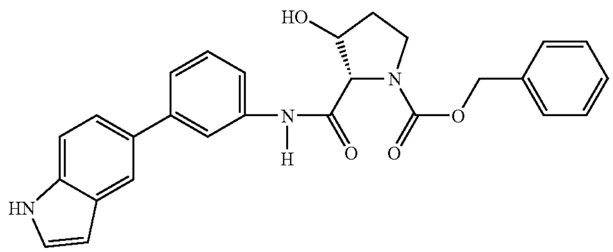 | 3-Hydroxy-2-[3-(1H-indol-5-yl)-phenylcarbamoyl]-pyrrolidine-1-carboxylic acid benzyl ester |
| 6232 | 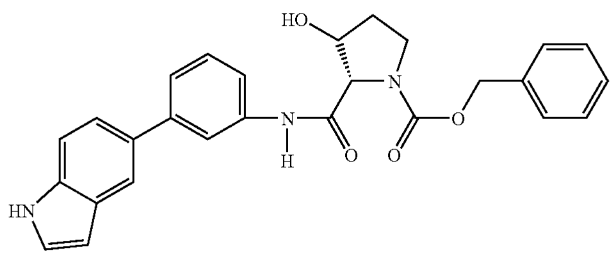 | 3-Hydroxy-2-[3-(1H-indol-5-yl)-phenylcarbamoyl]-pyrrolidine-1-carboxylic acid benzyl ester |
| 6233 | 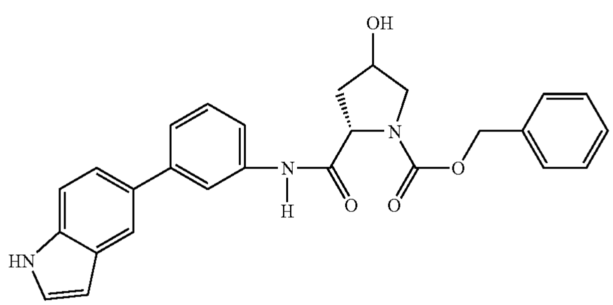 | 4-Hydroxy-2-[3-(1H-indol-5-yl)-phenylcarbamoyl]-pyrrolidine-1-carboxylic acid benzyl ester |
| 6234 | 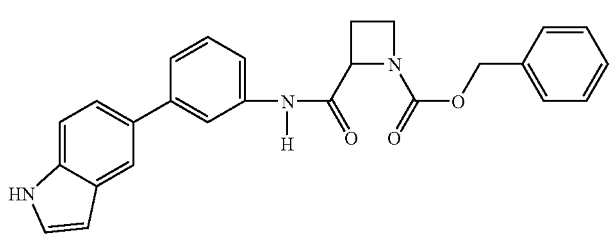 | 2-[3-(1H-Indol-5-yl)-phenylcarbamoyl]-azetidine-1-carboxylic acid benzyl ester |
| 6235 | 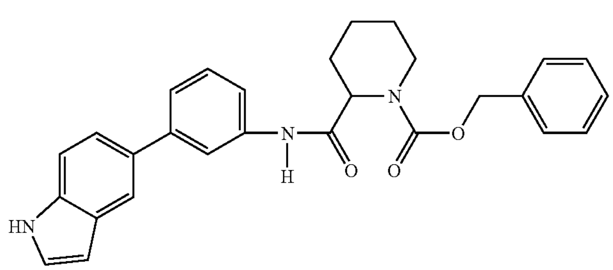 | 2-[3-(1H-Indol-5-yl)-phenylcarbamoyl]-piperidine-1-carboxylic acid benzyl ester |

TABLE 1-continued

| Ex. | Compound Structure | Compound Name |
| --- | --- | --- |
| 6236 | 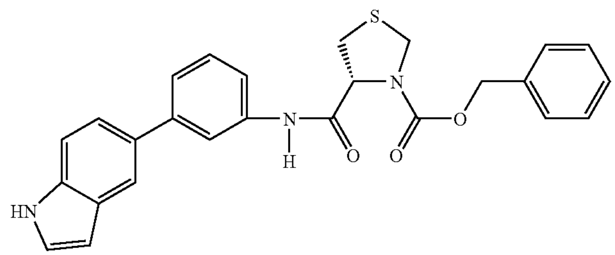 | 4-[3-(1H-Indol-5-yl)-phenylcarbamoyl]-thiazolidine-3-carboxylic acid benzyl ester |
| 6237 | 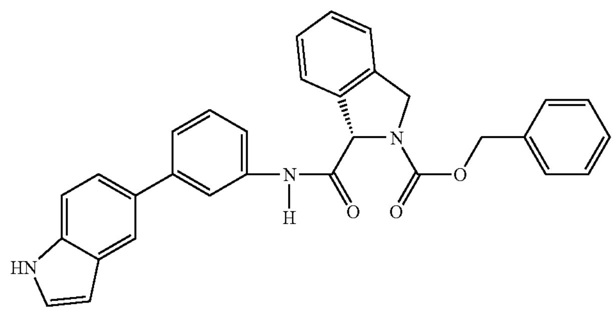 | 1-[3-(1H-Indol-5-yl)-phenylcarbamoyl]-1,3-dihydro-isoindole-2-carboxylic acid benzyl ester |
| 6238 | 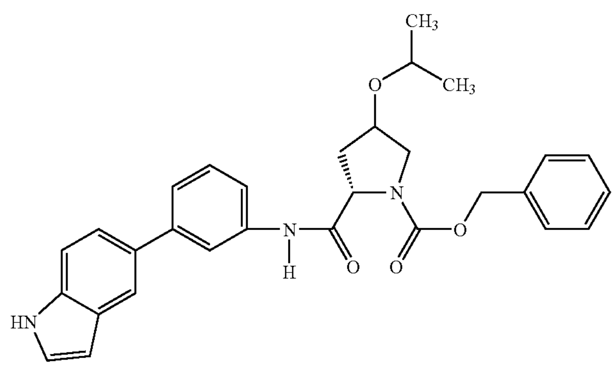 | 2-[3-(1H-Indol-5-yl)-phenylcarbamoyl]-4-isopropoxy-pyrrolidine-1-carboxylic acid benzyl ester |
| 6239 | 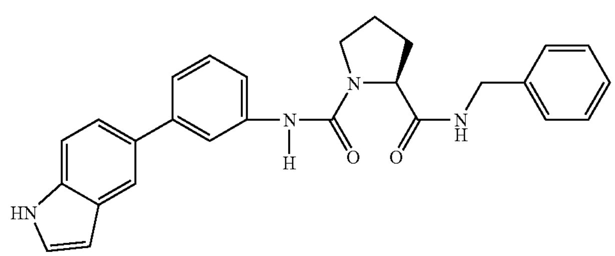 | Pyrrolidine-1,2-dicarboxylic acid 2-benzylamide 1-{[3-(1H-indol-5-yl)-phenyl]-amide} |
| 6240 | 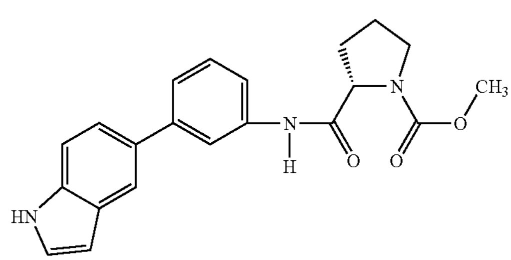 | 2-[3-(1H-Indol-5-yl)-phenylcarbamoyl]-pyrrolidine-1-carboxylic acid methyl ester |

TABLE 1-continued

| Ex. | Compound Structure | Compound Name |
|---|---|---|
| 6241 | 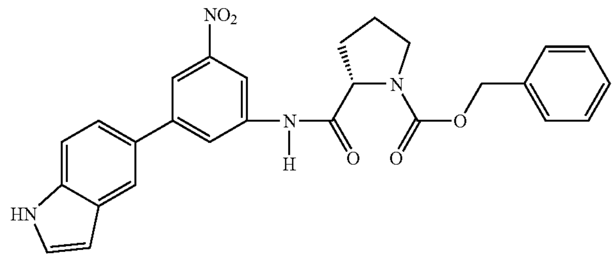 | 2-[3-(1H-Indol-5-yl)-5-nitro-phenylcarbamoyl]-pyrrolidine-1-carboxylic acid benzyl ester |
| 6242 | 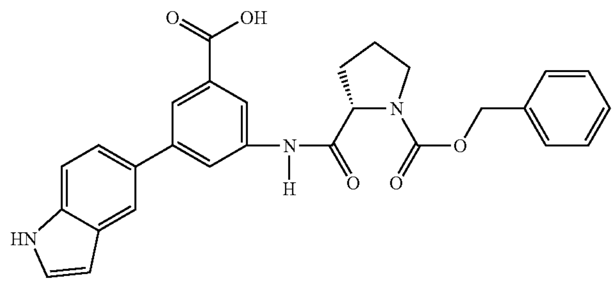 | 2-[3-Carboxy-5-(1H-indol-5-yl)-phenylcarbamoyl]-pyrrolidine-1-carboxylic acid benzyl ester |
| 6243 | 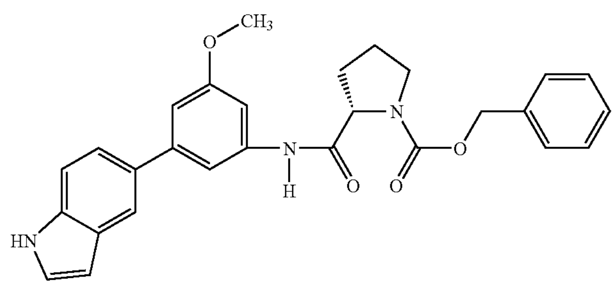 | 2-[3-(1H-Indol-5-yl)-5-methoxy-phenylcarbamoyl]-pyrrolidine-1-carboxylic acid benzyl ester |
| 6244 | 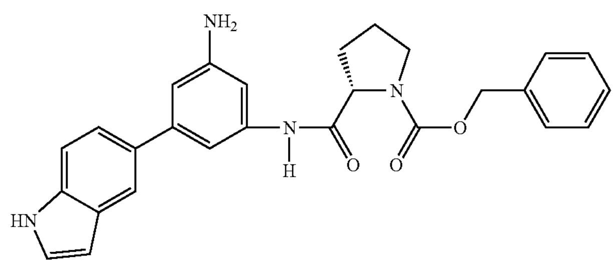 | 2-[3-Amino-5-(1H-indol-5-yl)-phenylcarbamoyl]-pyrrolidine-1-carboxylic acid benzyl ester |
| 6301 | 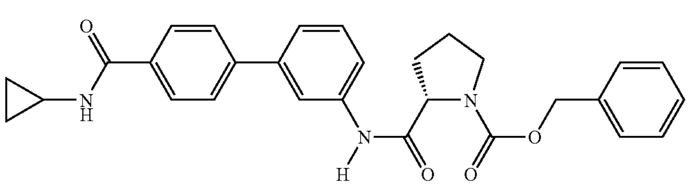 | 2-(4'-Cyclopropylcarbamoyl-biphenyl-3-ylcarbamoyl)-pyrrolidine-1-carboxylic acid benzyl ester |
| 6302 | 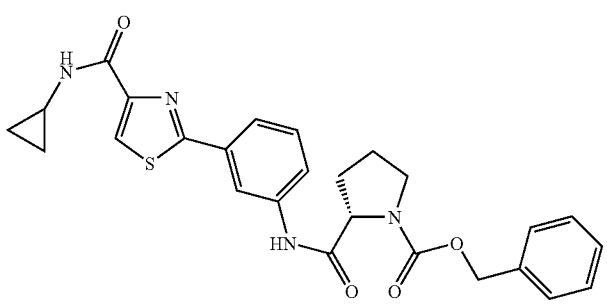 | 2-[3-(4-Cyclopropylcarbamoyl-thiazol-2-yl)-phenylcarbamoyl]-pyrrolidine-1-carboxylic acid benzyl ester |

TABLE 1-continued

| Ex. | Compound Structure | Compound Name |
| --- | --- | --- |
| 6303 | 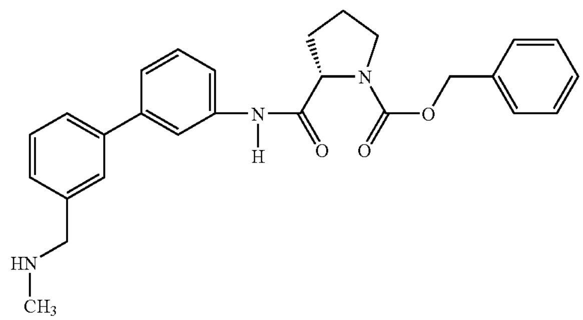 | 2-(3'-Methylaminomethyl-biphenyl-3-ylcarbamoyl)-pyrrolidine-1-carboxylic acid benzyl ester |
| 6304 | 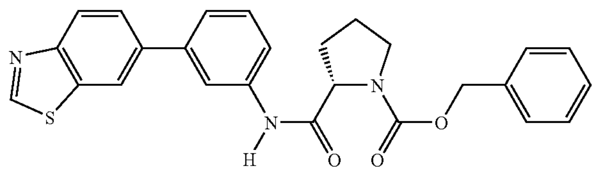 | 2-(3-Benzothiazol-6-yl-phenylcarbamoyl)-pyrrolidine-1-carboxylic acid benzyl ester |
| 6305 | 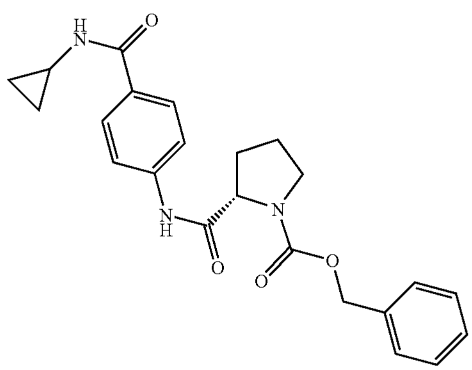 | 2-(4-Cyclopropylcarbamoyl-phenylcarbamoyl)-pyrrolidine-1-carboxylic acid benzyl ester |
| 6306 | 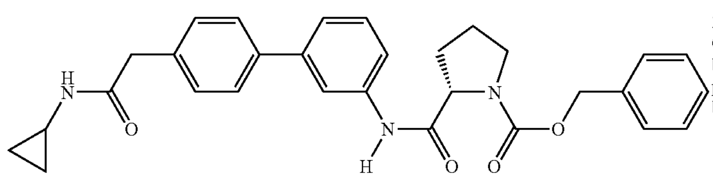 | 2-(4'-Cyclopropylcarbamoylmethyl-biphenyl-3-ylcarbamoyl)-pyrrolidine-1-carboxylic acid benzyl ester |
| 6307 | 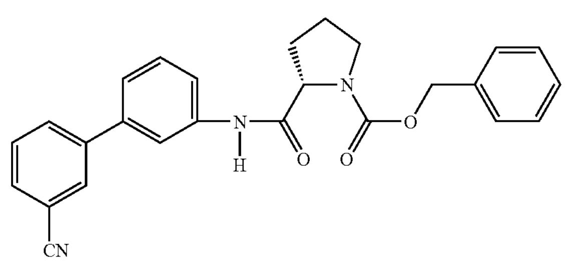 | 2-(3'-Cyano-biphenyl-3-ylcarbamoyl)-pyrrolidine-1-carboxylic acid benzyl ester |
| 6308 | 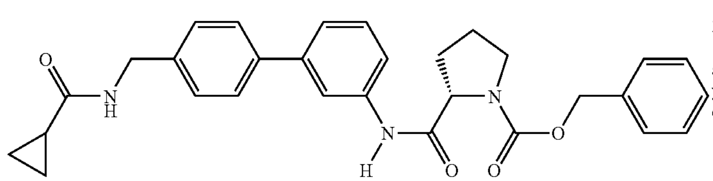 | 2-{4'-[(Cyclopropanecarbonyl-amino)-methyl]-biphenyl-3-ylcarbamoyl}-pyrrolidine-1-carboxylic acid benzyl ester |

TABLE 1-continued

| Ex. | Compound Structure | Compound Name |
|---|---|---|
| 6309 | 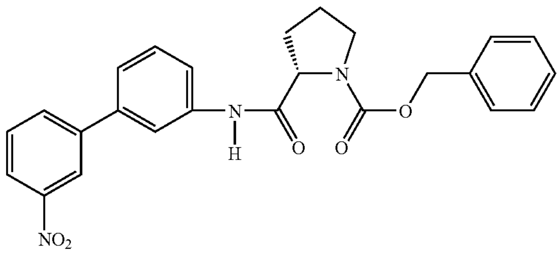 | 2-(3'-Nitro-biphenyl-3-ylcarbamoyl)-pyrrolidine-1-carboxylic acid benzyl ester |
| 6310 | 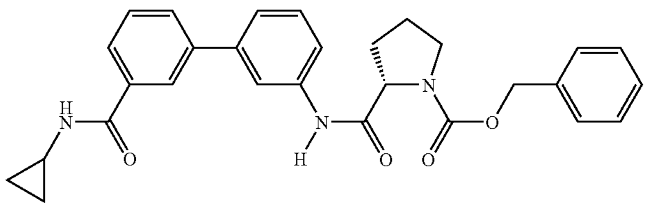 | 2-(3'-Cyclopropylcarbamoyl-biphenyl-3-ylcarbamoyl)-pyrrolidine-1-carboxylic acid benzyl ester |
| 6311 | 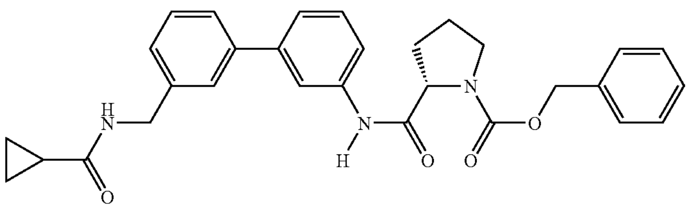 | 2-{3'-[(Cyclopropanecarbonyl-amino)-methyl]-biphenyl-3-ylcarbamoyl}-pyrrolidine-1-carboxylic acid benzyl ester |
| 6312 | 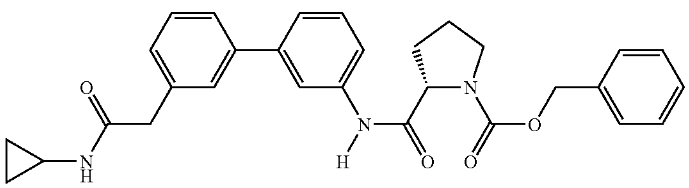 | 2-(3'-Cyclopropylcarbamoylmethyl-biphenyl-3-ylcarbamoyl)-pyrrolidine-1-carboxylic acid benzyl ester |

In another embodiment, the present invention provides a pharmaceutical composition comprising a pharmaceutically acceptable carrier and a therapeutically effective amount of a compound of Formula (I)-(II) or a stereoisomer, tautomer, or a pharmaceutically acceptable salt thereof for treating or preventing in a patient a viral infection mediated at least in part by a virus in the Flaviviridae family of viruses.

In some embodiments, the composition is for treating or preventing HCV.

In other embodiments, the composition comprises a compound from Table 1 or a stereoisomer, tautomer, or a pharmaceutically acceptable salt thereof.

In other embodiments, the composition comprises a compound or a stereoisomer, tautomer, or a pharmaceutically acceptable salt thereof that is 2-(3-Methylphenylcarbamoyl-pyrrolidine-1-carboxylic acid benzyl ester;

2-(4-Iodo-phenylcarbamoyl)-pyrrolidine-1-carboxylic acid benzyl ester;

2-(2,4-Dimethyl-phenylcarbamoyl)-pyrrolidine-1-carboxylic acid benzyl ester;

2-(2,5-Dimethyl-phenylcarbamoyl)-pyrrolidine-1-carboxylic acid benzyl ester;

2-(4-Methylphenylcarbamoyl)-5-oxo-pyrrolidine-1-carboxylic acid benzyl ester;

2-(2,4-Dimethyl-phenylcarbamoyl)-5-oxo-pyrrolidine-1-carboxylic acid benzyl ester;

2-(2,5-Dimethyl-phenylcarbamoyl)-5-oxo-pyrrolidine-1-carboxylic acid benzyl ester;

2-(3-Methylphenylcarbamoyl)-5-oxo-pyrrolidine-1-carboxylic acid benzyl ester;

2-(4-Methoxy-phenylcarbamoyl)-5-oxo-pyrrolidine-1-carboxylic acid benzyl ester;

2-Oxo-5-phenylcarbamoyl-pyrrolidine-1-carboxylic acid benzyl ester;

4-Hydroxy-2-(4-methoxy-phenylcarbamoyl)-pyrrolidine-1-carboxylic acid benzyl ester;

4-Hydroxy-2-(2-methoxy-phenylcarbamoyl)-pyrrolidine-1-carboxylic acid benzyl ester;

2-(2,5-Dimethyl-phenylcarbamoyl)-4-hydroxy-pyrrolidine-1-carboxylic acid benzyl ester;

4-Hydroxy-2-(4-iodo-2-methyl-phenylcarbamoyl)-pyrrolidine-1-carboxylic acid benzyl ester;

2-(4-Bromo-phenylcarbamoyl)-4-hydroxy-pyrrolidine-1-carboxylic acid benzyl ester;

4-Hydroxy-2-(4-iodo-phenylcarbamoyl)-pyrrolidine-1-carboxylic acid benzyl ester;

2-{4-[(Furan-2-carbonyl)-amino]-phenylcarbamoyl}-pyrrolidine-1-carboxylic acid benzyl ester;

2-{4-[(Pyridin-2-ylmethyl)-sulfamoyl]-phenylcarbamoyl}-pyrrolidine-1-carboxylic acid benzyl ester;

2-(4-Phenoxy-phenylcarbamoyl)-pyrrolidine-1-carboxylic acid benzyl ester;
2-(4-Methoxycarbonyl-phenylcarbamoyl)-pyrrolidine-1-carboxylic acid benzyl ester;
2-[3-(2-Isopropyl-5-methyl-phenoxy)-5-nitro-phenylcarbamoyl]-pyrrolidine-1-carboxylic acid benzyl ester;
2-[4-Hydroxy-3-(5-methyl-benzooxazol-2-yl)-phenylcarbamoyl]-pyrrolidine-1-carboxylic acid benzyl ester;
2-[3-Hydroxy-4-(5-methyl-benzooxazol-2-yl)-phenylcarbamoyl]-pyrrolidine-1-carboxylic acid benzyl ester; or
2-[3-(4-Fluoro-phenylsulfanyl)-5-nitro-phenylcarbamoyl]-pyrrolidine-1-carboxylic acid benzyl ester.

In one embodiment, the present invention provides a method for treating or preventing a viral infection in a patient mediated at least in part by a virus in the Flaviviridae family of viruses which method comprises administering to the patient a compound of Formula (I)-(II) or a stereoisomer, tautomer, or a pharmaceutically acceptable salt thereof.

In one embodiment, the present invention provides use of a compound or a stereoisomer, tautomer, or a pharmaceutically acceptable salt thereof as described herein in the manufacture of a medicament for treating a viral infection in a patient, wherein the viral infection is mediated at least in part by a virus in the Flaviviridae family of viruses.

In some aspects, the viral infection is a hepatitis C mediated viral infection.

In other aspects, the administration of a therapeutically effective amount of the compounds of the invention are used in combination with one or more agents active against hepatitis C virus.

In some embodiments, the agent active against hepatitis C virus is an inhibitor of HCV proteases, HCV polymerase, HCV helicase, HCV NS4B protein, HCV entry, HCV assembly, HCV egress, HCV NS5A protein, or inosine 5'-monophosphate dehydrogenase.

In other embodiments, agent active against hepatitis C virus is interferon.

In still other embodiments of the method of treatment or prevention, the compound is selected from the group consisting of a compound from Table 1 or a stereoisomer, tautomer, or a pharmaceutically acceptable salt thereof.

In other embodiments, the composition comprises a compound or a stereoisomer, tautomer, or a pharmaceutically acceptable salt thereof that is 2-(3-Methylphenylcarbamoyl-pyrrolidine-1-carboxylic acid benzyl ester;
2-(4-Iodo-phenylcarbamoyl)-pyrrolidine-1-carboxylic acid benzyl ester;
2-(2,4-Dimethyl-phenylcarbamoyl)-pyrrolidine-1-carboxylic acid benzyl ester;
2-(2,5-Dimethyl-phenylcarbamoyl)-pyrrolidine-1-carboxylic acid benzyl ester;
2-(4-Methylphenylcarbamoyl)-5-oxo-pyrrolidine-1-carboxylic acid benzyl ester;
2-(2,4-Dimethyl-phenylcarbamoyl)-5-oxo-pyrrolidine-1-carboxylic acid benzyl ester;
2-(2,5-Dimethyl-phenylcarbamoyl)-5-oxo-pyrrolidine-1-carboxylic acid benzyl ester;
2-(3-Methylphenylcarbamoyl)-5-oxo-pyrrolidine-1-carboxylic acid benzyl ester;
2-(4-Methoxy-phenylcarbamoyl)-5-oxo-pyrrolidine-1-carboxylic acid benzyl ester;
2-Oxo-5-phenylcarbamoyl-pyrrolidine-1-carboxylic acid benzyl ester;
4-Hydroxy-2-(4-methoxy-phenylcarbamoyl)-pyrrolidine-1-carboxylic acid benzyl ester;
4-Hydroxy-2-(2-methoxy-phenylcarbamoyl)-pyrrolidine-1-carboxylic acid benzyl ester;
2-(2,5-Dimethyl-phenylcarbamoyl)-4-hydroxy-pyrrolidine-1-carboxylic acid benzyl ester;
4-Hydroxy-2-(4-iodo-2-methyl-phenylcarbamoyl)-pyrrolidine-1-carboxylic acid benzyl ester;
2-(4-Bromo-phenylcarbamoyl)-4-hydroxy-pyrrolidine-1-carboxylic acid benzyl ester;
4-Hydroxy-2-(4-iodo-phenylcarbamoyl)-pyrrolidine-1-carboxylic acid benzyl ester;
2-{4-[(Furan-2-carbonyl)-amino]-phenylcarbamoyl}-pyrrolidine-1-carboxylic acid benzyl ester;
2-{4-[(Pyridin-2-ylmethyl)-sulfamoyl]-phenylcarbamoyl}-pyrrolidine-1-carboxylic acid benzyl ester;
2-(4-Phenoxy-phenylcarbamoyl)-pyrrolidine-1-carboxylic acid benzyl ester;
2-(4-Methoxycarbonyl-phenylcarbamoyl)-pyrrolidine-1-carboxylic acid benzyl ester;
2-[3-(2-Isopropyl-5-methyl-phenoxy)-5-nitro-phenylcarbamoyl]-pyrrolidine-1-carboxylic acid benzyl ester;
2-[4-Hydroxy-3-(5-methyl-benzooxazol-2-yl)-phenylcarbamoyl]-pyrrolidine-1-carboxylic acid benzyl ester;
2-[3-Hydroxy-4-(5-methyl-benzooxazol-2-yl)-phenylcarbamoyl]-pyrrolidine-1-carboxylic acid benzyl ester;
2-[3-(4-Fluoro-phenylsulfanyl)-5-nitro-phenylcarbamoyl]-pyrrolidine-1-carboxylic acid benzyl ester;
Benzyl 2-(3-(N-(3-chlorophenyl)-N-(2-isopropoxy-2-oxoethyl)sulfamoyl)phenylcarbamoyl)pyrrolidine-1-carboxylate;
Benzyl 2-(4-(decahydroquinoline-1-carbonyl)phenylcarbamoyl)pyrrolidine-1-carboxylate;
Benzyl 2-(2-(methoxycarbonyl)phenylcarbamoyl)pyrrolidine-1-carboxylate;
Benzyl 2-(4-aminoquinazolin-6-ylcarbamoyl)pyrrolidine-1-carboxylate;
Benzyl 2-(2,4-diaminoquinazolin-6-ylcarbamoyl)pyrrolidine-1-carboxylate; or
tert-Butyl 2-(2,4-diaminoquinazolin-6-ylcarbamoyl)pyrrolidine-1-carboxylate.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician.

Therapeutically effective amounts of compounds of Formula (I) may range from approximately 0.05 to 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-700 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of Formula (I) based on the total formulation, with the balance being one or more suitable pharmaceutical excipients. Preferably, the compound is present at a level of about 1-80 wt %. Representative pharmaceutical formulations containing a compound of Formula (I) are described below.

Additionally, the present invention is directed to a pharmaceutical composition comprising a therapeutically effective amount of a compound of the present invention in combination with a therapeutically effective amount of another active agent against RNA-dependent RNA virus and, in particular, against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffman-LaRoche, Nutley, N.J.), interferon-α2b (such as Intron-A interferon available from Schering Corp., Kenilworth, N.J., USA), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.,* 35:201-210 (2000).

The agents active against hepatitis C virus also include agents that inhibit HCV proteases, HCV polymerase, HCV helicase, HCV NS4B protein, HCV entry, HCV assembly, HCV egress, HCV NS5A protein, and inosine 5'-monophosphate dehydrogenase. Other agents include nucleoside analogs for the treatment of an HCV infection. Still other compounds include those disclosed in WO 2004/014313 and WO 2004/014852 and in the references cited therein. The patent applications WO 2004/014313 and WO 2004/014852 are hereby incorporated by references in their entirety.

Specific antiviral agents include Omega IFN (BioMedicines Inc.), BILN-2061 (Boehringer Ingelheim), Summetrel (Endo Pharmaceuticals Holdings Inc.), Roferon A (F. Hoffman-La Roche), Pegasys (F. Hoffman-La Roche), Pegasys/Ribaravin (F. Hoffman-La Roche), CellCept (F. Hoffman-La Roche), Wellferon (GlaxoSmithKline), Albuferon-α (Human Genome Sciences Inc.), Levovirin (ICN Pharmaceuticals), IDN-6556 (Idun Pharmaceuticals), IP-501 (Indevus Pharmaceuticals), Actimmune (InterMune Inc.), Infergen A (InterMune Inc.), ISIS 14803 (ISIS Pharmaceuticals Inc.), JTK-003 (Japan Tobacco Inc.), Pegasys/Ceplene (Maxim Pharmaceuticals), Ceplene (Maxim Pharmaceuticals), Civacir (Nabi Biopharmaceuticals Inc.), Intron A/Zadaxin (RegeneRx), Levovirin (Ribapharm Inc.), Viramidine (Ribapharm Inc.), Heptazyme (Ribozyme Pharmaceuticals), Intron A (Schering-Plough), PEG-Intron (Schering-Plough), Rebetron (Schering-Plough), Ribavirin (Schering-Plough), PEG-Intron/Ribavirin (Schering-Plough), Zadazim (SciClone), Rebif (Serono), IFN-β/EMZ701 (Transition Therapeutics), T67 (Tularik Inc.), VX-497 (Vertex Pharmaceuticals Inc.), VX-950/LY-570310 (Vertex Pharmaceuticals Inc.), Omniferon (Viragen Inc.), XTL-002 (XTL Biopharmaceuticals), SCH 503034 (Schering-Plough), isatoribine and its prodrugs ANA971 and ANA975 (Anadys), R1479 (Roche Biosciences), Valopicitabine (Idenix), NIM811 (Novartis), and Actilon (Coley Pharmaceuticals).

In some embodiments, the compositions and methods of the present invention contain a compound of Formula (I) and interferon. In some aspects, the interferon is selected from the group consisting of interferon alpha 2B, pegylated interferon alpha, consensus interferon, interferon alpha 2A, and lymphoblastoid interferon tau.

In other embodiments the compositions and methods of the present invention contain a compound of Formula (I) and a compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'monophosphate dehydrogenase inhibitor, amantadine, and rimantadine.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4th Edition), and Larock's *Comprehensive Organic Transformations* (VCH Publishers Inc., 1989).

The various starting materials, intermediates, and compounds of the invention may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Accordingly, in one embodiment the present invention provides a method for synthesizing a compound, stereoisomer, tautomer, or a pharmaceutically acceptable salt of Formula (I)

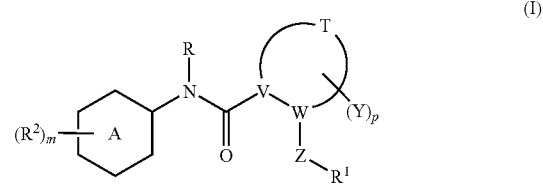

(I)

wherein the method comprises reacting an amine having the formula

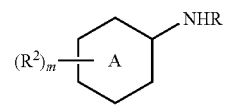

with an acid having the formula

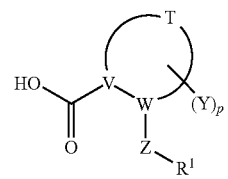

in the presence of an amide coupling reagent, wherein A, R, $R^1$, $R^2$, T, V, W, Z, Y, m, and p are as previously defined;
provided that when A is phenyl, V is CH, and W is N, then $R^2$ is not a substituted heterocycle having the structure

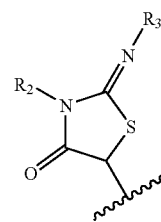

wherein $R_2$ and $R_3$ are as defined in WO 2004/014313 and WO 2004/014852; and provided that the compound is not
2-(3-Methylphenylcarbamoyl-pyrrolidine-1-carboxylic acid benzyl ester;
2-(4-Iodo-phenylcarbamoyl)-pyrrolidine-1-carboxylic acid benzyl ester;
2-(2,4-Dimethyl-phenylcarbamoyl)-pyrrolidine-1-carboxylic acid benzyl ester;
2-(2,5-Dimethyl-phenylcarbamoyl)-pyrrolidine-1-carboxylic acid benzyl ester;

2-(4-Methylphenylcarbamoyl)-5-oxo-pyrrolidine-1-carboxylic acid benzyl ester;
2-(2,4-Dimethyl-phenylcarbamoyl)-5-oxo-pyrrolidine-1-carboxylic acid benzyl ester;
2-(2,5-Dimethyl-phenylcarbamoyl)-5-oxo-pyrrolidine-1-carboxylic acid benzyl ester;
2-(3-Methylphenylcarbamoyl)-5-oxo-pyrrolidine-1-carboxylic acid benzyl ester;
2-(4-Methoxy-phenylcarbamoyl)-5-oxo-pyrrolidine-1-carboxylic acid benzyl ester;
2-Oxo-5-phenylcarbamoyl-pyrrolidine-1-carboxylic acid benzyl ester;
4-Hydroxy-2-(4-methoxy-phenylcarbamoyl)-pyrrolidine-1-carboxylic acid benzyl ester;
4-Hydroxy-2-(2-methoxy-phenylcarbamoyl)-pyrrolidine-1-carboxylic acid benzyl ester;
2-(2,5-Dimethyl-phenylcarbamoyl)-4-hydroxy-pyrrolidine-1-carboxylic acid benzyl ester;
4-Hydroxy-2-(4-iodo-2-methyl-phenylcarbamoyl)-pyrrolidine-1-carboxylic acid benzyl ester;
2-(4-Bromo-phenylcarbamoyl)-4-hydroxy-pyrrolidine-1-carboxylic acid benzyl ester;
4-Hydroxy-2-(4-iodo-phenylcarbamoyl)-pyrrolidine-1-carboxylic acid benzyl ester;
2-{4-[(Furan-2-carbonyl)-amino]-phenylcarbamoyl}-pyrrolidine-1-carboxylic acid benzyl ester;
2-{4-[(Pyridin-2-ylmethyl)-sulfamoyl]-phenylcarbamoyl}-pyrrolidine-1-carboxylic acid benzyl ester;
2-(4-Phenoxy-phenylcarbamoyl)-pyrrolidine-1-carboxylic acid benzyl ester;
2-(4-Methoxycarbonyl-phenylcarbamoyl)-pyrrolidine-1-carboxylic acid benzyl ester;
2-[3-(2-Isopropyl-5-methyl-phenoxy)-5-nitro-phenylcarbamoyl]-pyrrolidine-1-carboxylic acid benzyl ester;
2-[4-Hydroxy-3-(5-methyl-benzooxazol-2-yl)-phenylcarbamoyl]-pyrrolidine-1-carboxylic acid benzyl ester;
2-[3-Hydroxy-4-(5-methyl-benzooxazol-2-yl)-phenylcarbamoyl]-pyrrolidine-1-carboxylic acid benzyl ester;
2-[3-(4-Fluoro-phenylsulfanyl)-5-nitro-phenylcarbamoyl]-pyrrolidine-1-carboxylic acid benzyl ester;
Benzyl 2-(3-(N-(3-chlorophenyl)-N-(2-isopropoxy-2-oxoethyl)sulfamoyl)phenylcarbamoyl)pyrrolidine-1-carboxylate;
Benzyl 2-(4-(decahydroquinoline-1-carbonyl)phenylcarbamoyl)pyrrolidine-1-carboxylate;
Benzyl 2-(2-(methoxycarbonyl)phenylcarbamoyl)pyrrolidine-1-carboxylate;
Benzyl 2-(4-aminoquinazolin-6-ylcarbamoyl)pyrrolidine-1-carboxylate;
Benzyl 2-(2,4-diaminoquinazolin-6-ylcarbamoyl)pyrrolidine-1-carboxylate; or
tert-Butyl 2-(2,4-diaminoquinazolin-6-ylcarbamoyl)pyrrolidine-1-carboxylate.

A variety of amide coupling reagents may be used to from the amide bond, including the use of carbodiimides such as N—N'-dicyclohexylcarbodiimide (DCC), N—N'-diisopropylcarbodiimide (DIPCDI), and 1-ethyl-3-(3'-dimethylaminopropyl)carbodiimide (EDCI). The carbodiimides may be used in conjunction with additives such as benzotriazoles 7-aza-1-hydroxybenzotriazole (HOAt), 1-hydroxybenzotriazole (HOBt), and 6-chloro-1-hydroxybenzotriazole (Cl-HOBt).

Amide coupling reagents also include amininum and phosphonium based reagents. Aminium salts include
N-[(dimethylamino)-1H-1,2,3-triazolo[4,5-b]pyridine-1-yl-methylene]-N-methylmethanaminium hexafluorophosphate N-oxide (HATU),
N-[(1H-benzotriazol-1-yl)(dimethylamino)methylene]-N-methylmethanaminium hexafluorophosphate N-oxide (HBTU),
N-[(1H-6-chlorobenzotriazol-1-yl)(dimethylamino)methylene]-N-methylmethanaminium hexafluorophosphate N-oxide (HCTU),
N-[(1H-benzotriazol-1-yl)(dimethylamino)methylene]-N-methylmethanaminium tetrafluoroborate N-oxide (TBTU), and
N-[(1H-6-chlorobenzotriazol-1-yl)(dimethylamino)methylene]-N-methylmethanaminium tetrafluoroborate N-oxide (TCTU). Phosphonium salts include
7-azabenzotriazol-1-yl-N-oxy-tris(pyrrolidino)phosphonium hexafluorophosphate (PyAOP) and benzotriazol-1-yl-N-oxy-tris(pyrrolidino)phosphonium hexafluorophosphate (PyBOP).

The amide formation step may be conducted in a polar solvent such as dimethylformamide (DMF) and may also include an organic base such as diisopropylethylamine (DIEA).

Scheme 1 shows the synthesis of the compounds of the invention where A is a phenyl, R is hydrogen, V, W, and T together form a (S)-pyrrolidine ring, p is 0, and Z-R$^1$ together form a benzyloxycarbonyl group. Amine 1.1 is coupled with N-benzyloxycarbonyl protected L-proline (Z-Pro-OH) using standard peptide coupling procedures to form the amide 1.3.

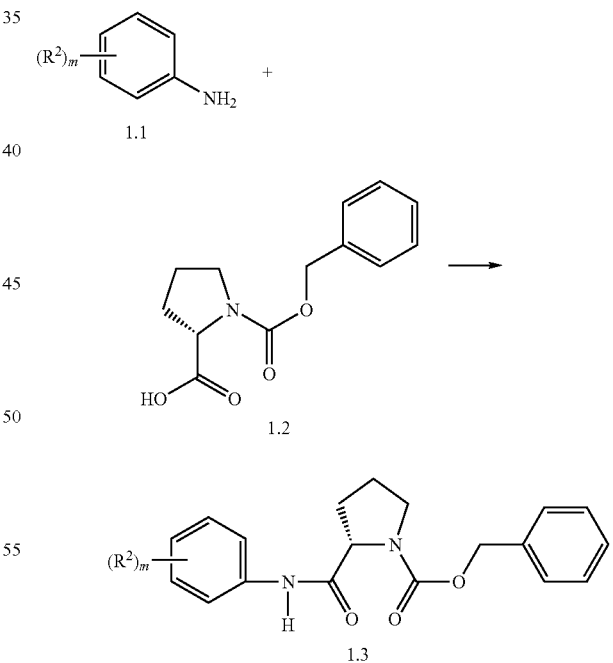

Scheme 2 shows the synthesis of the compounds of the invention where R$^2$ is an substituted or unsubstituted phenyl group. Starting material 2.1, where X is a halo group such as iodide or bromide, is synthesized as in Scheme 1 and is coupled to boronic acid 2.2 under Suzuki coupling conditions to form the biaryl compound 1.2.

Scheme 2

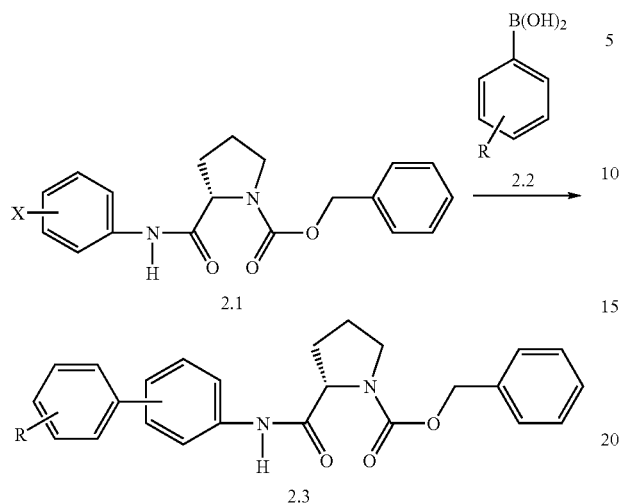

Scheme 3 shows the synthesis of the compounds of the invention where $R^2$ is an substituted or unsubstituted benzimidazolmethyl group. Acid 3.1, synthesized as in Scheme 1 from the appropriate starting materials, is coupled to diamine 3.2 under amide coupling conditions to form compound 3.3. Cyclization of 3.2 to 3.3 may be effected by heating and optionally in the presence of a dehydrating agent such as acetic acid.

The foregoing and other aspects of the present invention may be better understood in connection with the following representative examples.

EXAMPLES

The examples below as well as throughout the application, the following abbreviations have the following meanings. If not defined, the terms have their generally accepted meanings.

| | |
|---|---|
| atm = | atmospheres |
| cm = | centimeter |
| DMF = | dimethylformamide |
| DIEA = | diisopropylethylamine |
| DMSO = | dimethylsulfoxide |
| eq. = | Equivalents |
| F.W. = | Formula weight |
| g = | gram |
| HATU = | N-[(dimethylamino)-1H-1,2,3-triazolo[4,5-b]pyridine-1-ylmethylene]-N-methylmethanaminium hexafluorophosphate N-oxide |
| HPLC = | high pressure liquid chromatography |
| KOAc = | potassium acetate |
| L = | liter |
| MeCN = | acetonitrile |
| mg = | milligram |
| mL = | milliliter |
| mmol = | millimole |
| MS = | mass spectrum |
| TEA = | triethylamine |

Scheme 3

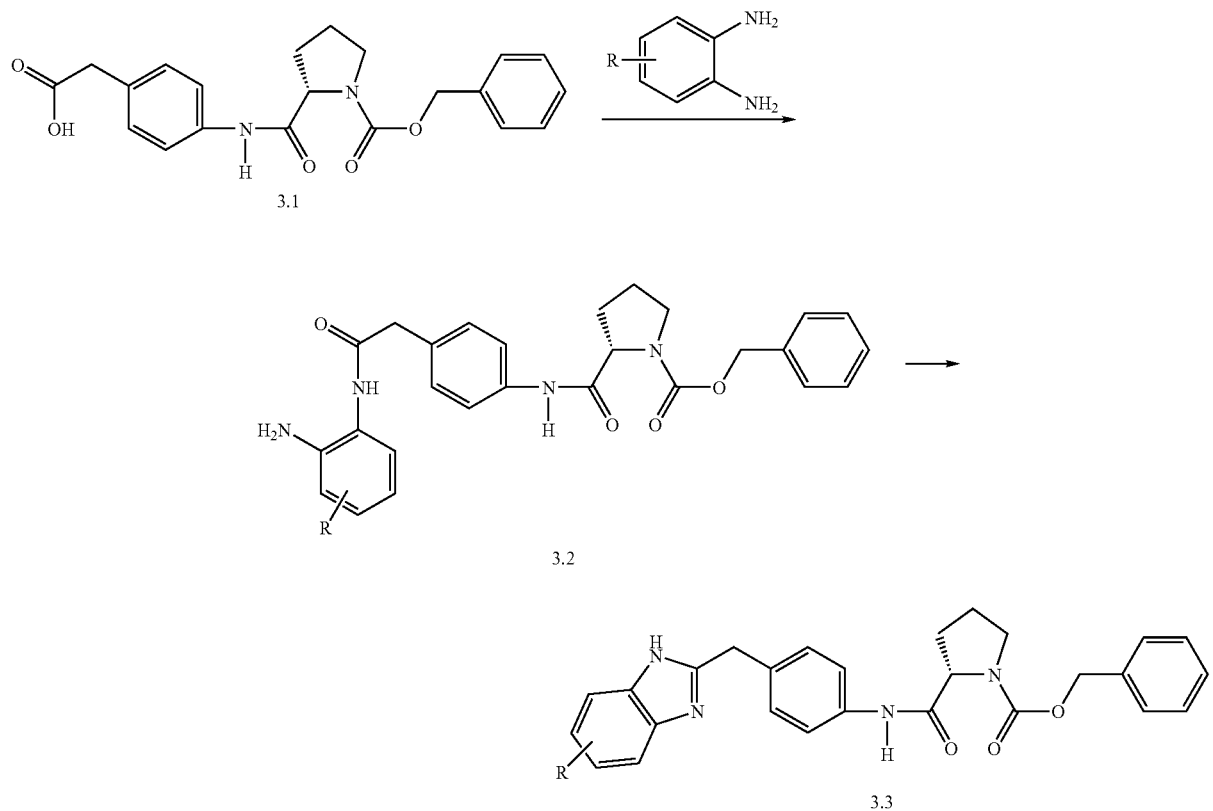

| | |
|---|---|
| TFA = | trifluoroacetic acid |
| THF = | tetrahydrofuran |
| TLC = | thin layer chromatography |
| v/v = | volume/volume |
| μL = | microliter |

Example 1

General Procedure A

A mixture of (S)-Pyrrolidine-1,2-dicarboxylic acid 1-benzyl ester (F.W.=249.27, 0.54 g, 2.15 mmol), HATU (F.W.=380.25, 0.82 g, 2.16 mmol), and DIEA (0.4 mL, 0.05 mmol) in DMF (30 mL) was stirred at room temperature for 1 h to provide a 0.072 mM solution. To each of the amines described in the following Examples was added 1 mL of this solution (0.072 mM) and the reaction mixtures were stirred at room temperature overnight. The resulting mixtures were diluted with DMF (5 mL) and water (0.5 mL) then purified by reverse phase HPLC to furnish the corresponding products.

General Procedure B

A mixture of (S)-Pyrrolidine-1,2-dicarboxylic acid 1-benzyl ester (F.W.=249.27, 0.35 g, 1.4 mmol), HATU (F.W.=380.25, 0.53 g, 1.4 mmol), and DIEA (0.4 mL, 0.05 mmol) in DMF (20 mL) was stirred at room temperature for 1 h to provide a 0.070 mM solution. To each of the amines described in the following Examples was added 1 mL of this solution (0.070 mM) and the reaction mixtures were stirred at room temperature overnight. The resulting mixtures were diluted with DMF (5 mL) and water (0.5 mL) then purified by reverse phase HPLC to furnish the corresponding products.

General Procedure C

A mixture of (S)-Pyrrolidine-1,2-dicarboxylic acid 1-benzyl ester (F.W.=249.27, 0.15 g, 0.6 mmol), HATU (F.W.=380.25, 0.209 g, 0.55 mmol), and DIEA (0.1 mL, 0.76 mmol) in DMF (5 mL) was stirred at room temperature for 1 h. This mixture had to be prepared each time for the reactions of the amines described in the following Examples. The individual mixtures were stirred at room temperature for 20 h., then filtered and separated by reverse phase HPLC (20-100% of buffer B; buffer A: water containing 0.1% TFA; buffer B: MeCN containing 0.1% TFA). The combined fraction was evaporated to dryness to furnish the desired products.

General Procedure D

A mixture of (S)-Pyrrolidine-1,2-dicarboxylic acid 1-benzyl ester (F.W.=249.27, 1.5 g, 4.0 mmol), HATU (1.6 g, 3.9 mmol), and DIEA (0.7 mL, 4.97 mmol) in DMF (30 mL) was stirred at room temperature for 1 h. (4-Amino-phenyl)-acetic acid (FW=151.17, 0.5 g, 3.31 mmol) was added. The reaction mixture was stirred at room temperature for 20 h. The mixture was filtered and separated by reverse phase HPLC (0-100% of buffer B; buffer A: water containing 0.1% TFA; buffer B: MeCN containing 0.1% TFA). The combined fraction was evaporated to furnish the desired product (S)-2-(4-Carboxymethyl-phenylcarbamoyl)-pyrrolidine-1-carboxylic acid benzyl ester.

A mixture of (S)-2-(4-Carboxymethyl-phenylcarbamoyl)-pyrrolidine-1-carboxylic acid benzyl ester (0.5 g, 1.3 mmol), HATU (0.5 g, 1.3 mmol), and DIEA (0.25 mL, 1.9 mmol) in DMF (16 mL) was stirred at room temperature for 1 h. To each of the diamines described in the following Examples was added 2 mL of this solution and the mixture were stirred at room temperature for 20 h. The resulting mixtures (intermediates) were washed with water, dried in speed vacuum overnight. Each resulting intermediate was dissolved in glacial acetic acid (10 mL) and the mixture was heated to reflux for 3 h then concentrated to give the crude product. Purification of the crude products by reverse phase HPLC (20-100% of buffer B; buffer A: water containing 0.1% TFA; buffer B: MeCN containing 0.1% TFA) furnished the corresponding desired products.

General Procedure E

A mixture of (S)-2-(4-Iodo-phenylcarbamoyl)-pyrrolidine-1-carboxylic acid benzyl ester (0.050 g, 0.11 mmol), aryl boronic acids (1.5 eq) described in the following Examples, Pd[P(Ph$_3$)]$_4$ (11 mol %, 15 mg), in MeOH (5 mL), NaHCO$_3$ (sat. aq., 1 mL) was degassed and heated to 70° C. overnight. The resulting mixture was filtered, concentrated, and purified by reverse phase HPLC (20-100% of buffer B; buffer A: water containing 0.1% TFA; buffer B: MeCN containing 0.1 TFA). The combined fraction was evaporated to dryness to furnish the desired products.

General Procedure F

A mixture of (S)-2-(3-Iodo-phenylcarbamoyl)-pyrrolidine-1-carboxylic acid benzyl ester (0.040 g, 0.09 mmol), aryl boronic acids (1.6 eq) described in the following Examples, Pd[P(Ph$_3$)]$_4$ (14 mol %, 15 mg), in MeOH (5 mL), NaHCO$_3$ (sat. aq., 1 mL) was degassed and heated to 70° C. overnight. The resulting mixture was filtered, concentrated, and purified by reverse phase HPLC (20-100% of buffer B; buffer A: water containing 0.1% TFA; buffer B: MeCN containing 0.1 TFA). The combined fraction was evaporated to dryness to furnish the desired products.

General Procedure G

A mixture of Z-Pro-OH (0.96 g, 3.84 mmol), HATU (1.46 g, 3.84 mmol), and DIEA (0.094 mL, 5.4 mmol) in DMF (30 mL) was stirred at room temperature for 1 hour. 1 or 2 mL of this solution was added to the amines described in the following Examples and reaction mixtures stirred at room temperature overnight. The resulting mixtures were diluted with DMF (5 mL) and water (0.5 mL) and purified using reverse phase HPLC to furnish the corresponding products.

General Procedure H

A mixture of (S)-2-(4-Iodo-phenylcarbamoyl)-pyrrolidine-1-carboxylic acid benzyl ester (0.040 g, 0.089 mmol), appropriate boronic acids described in the following Examples, tetrakis palladium (15 mg), sat. sodium bicarbonate (1 mL) in 1 mL of MeOH was degassed and then heated under reflux overnight. Reaction mixtures were filtered and evaporated. The resulting mixtures were diluted with DMF (5 mL) and water (0.5 mL) and purified using reverse phase HPLC to furnish the corresponding products.

General Procedure J

A solution of (S)-2-(3-Bromo-phenylcarbamoyl)-pyrrolidine-1-carboxylic acid benzyl ester (100 mg, 0.25 mmol), aryl boronic acid (1 eq) described in the following Examples, Pd[P(Ph)$_3$]$_4$ (5 mol %, 14 mg) in methanol (2 mL), NaHCO$_3$ (sat. aq., 300 uL) and DMF (400 uL) was degassed and heated to 70° C. overnight in a sealed vial. The reaction was cooled, filtered and the solvents removed. The resulting mixture was redissolved in 5 mL of 90% DMF, 10% water with 0.1% TFA and purified by reverse phase HPLC to give the products.

General Procedure K

A solution of (S)-2-[3-(4,4,5,5-Tetramethyl-[1,3,2]dioxaborolan-2-yl)-phenylcarbamoyl]-pyrrolidine-1-carboxylic acid benzyl ester (90 mg, 0.25 mmol), aryl bromide (1 eq) described in the following Examples, Pd[P(Ph)$_3$]$_4$ (5 mol %, 14 mg), in methanol (2 mL), NaHCO$_3$ (sat. aq., 300 uL) and DMF (400 uL) was degassed and heated to 70° C. overnight in a sealed vial. The reaction was cooled, filtered and the solvents removed. The resulting mixture was redissolved in 5 mL of 90% DMF, 10% water with 0.1% TFA and purified by reverse phase HPLC to give the products.

Example 1

2-(2',4'-Dimethoxy-biphenyl-4-ylcarbamoyl)-pyrrolidine-1-carboxylic acid benzyl ester (Compound 6001)

Using General Procedure H from 18.7 mg of 2,4-dimethoxyphenyl boronic acid.
MS: 461.1 (M+H$^+$).

Example 2

2-(4-Benzenesulfonylamino-phenylcarbamoyl)-pyrrolidine-1-carboxylic acid benzyl ester (Compound 6002)

Using General Procedure A from 10 mg of N-(4-Aminophenyl)-benzenesulfonamide. MS: 480.1 (M+H$^+$).

Example 3

2-[4-(4-Methyl-piperidine-1-sulfonyl)-phenylcarbamoyl]-pyrrolidine-1-carboxylic acid benzyl ester (Compound 6003)

Using General Procedure A from 10 mg of 3-(4-Methyl-piperidine-1-sulfonyl)-phenylamine. MS: 486.1 (M+H$^+$).

Example 4

2-[5-(2,3-Dichloro-benzyl)-thiazol-2-ylcarbamoyl]-pyrrolidine-1-carboxylic acid benzyl ester (Compound 6004)

Using General Procedure A from 10 mg of 4-Amino-N-(2,6-dichloro-phenyl)-benzamide. MS: 512.1 (M+H$^+$).

Example 5

2-[4-(3-Methyl-5-oxo-1-phenyl-1,5-dihydro-pyrazol-4-ylidenemethyl)-phenylcarbamoyl]-pyrrolidine-1-carboxylic acid benzyl ester (Compound 6005)

Using General Procedure A from 10 mg of 4-[1-(4-Aminophenyl)-meth-(Z)-ylidene]-5-methyl-2-phenyl-2,4-dihydro-pyrazol-3-one. MS: 509.1 (M+H$^+$).

Example 6

2-[4-(6-Bromo-4,5-dimethyl-H-benzoimidazol-2-ylmethyl)-phenylcarbamoyl]-pyrrolidine-1-carboxylic acid benzyl ester (Compound 6006)

Using General Procedure D from 40 mg of 3-Bromo-4,5-dimethyl-benzene-1,2-diamine. MS: 562.1 (M+H$^+$).

Example 7

2-(2,5-Dimethoxy-biphenyl-4-ylcarbamoyl)-pyrrolidine-1-carboxylic acid benzyl ester (Compound 6007)

Using General Procedure H from 18.7 mg of 2,5-dimethoxyphenyl boronic acid.
MS: 461.1 (M+H$^+$).

Example 8

2-(3'-Methoxy-biphenyl-3-ylcarbamoyl)-pyrrolidine-1-carboxylic acid benzyl ester (Compound 6008)

Using General Procedure F from 25 mg of 3-Methoxy phenyl boronic acid. Yield 15 mg. MS: 431.1 (M+H$^+$).

Example 9

2-[4-(1H-Indol-5-yl)-phenylcarbamoyl]-pyrrolidine-1-carboxylic acid benzyl ester (Compound 6019)

Using General Procedure E from 27 mg of 1H-indole 5 boronic acid. Yield 11 mg.
MS: 440.1 (M+H$^+$).

Example 10

2-[3-(1H-Indol-5-yl)-phenylcarbamoyl]-pyrrolidine-1-carboxylic acid benzyl ester (Compound 6010)

Using General Procedure F from 27 mg of 1H-indole 5 boronic acid. Yield 12.5 mg.
MS: 440.1 (M+H$^+$).

Example 11

2-([1,1';3',1'']Terphenyl-4-ylcarbamoyl)-pyrrolidine-1-carboxylic acid benzyl ester (Compound 6011)

Using General Procedure H from 27.7 mg of 2-biphenyl boronic acid. MS: 477.1 (M+H$^+$)

Example 12

2-(3-Pentafluorophenyloxy-phenylcarbamoyl)-pyrrolidine-1-carboxylic acid benzyl ester (Compound 6012)

Using General Procedure B from 10 mg of 3-Pentafluorophenyloxy-phenylamine.
MS: 507.1 (M+H$^+$).

Example 13

2-(3-Benzenesulfonyl-phenylcarbamoyl)-pyrrolidine-1-carboxylic acid benzyl ester (Compound 6013)

Using General Procedure B from 10 mg of 3-Benzenesulfonyl-phenylamine. MS: 465.1 (M+H$^+$)

Example 14

2-[4-(5,6-Dimethyl-1H-benzoimidazol-2-ylmethyl)-phenylcarbamoyl]-pyrrolidine-1-carboxylic acid benzyl ester (Compound 6014)

Using General Procedure D from 30 mg of 4,5-Dimethyl-benzene-1,2-diamine. MS: 483.2 (M+H$^+$)

Example 15

2-[4-(5-Methyl-1H-benzoimidazol-2-ylmethyl)-phenylcarbamoyl]-pyrrolidine-1-carboxylic acid benzyl ester (Compound 6015)

Using General Procedure D from 30 mg of 4-Methyl-benzene-1,2-diamine. MS: 469.1 (M+H$^+$)

Example 16

2-[4-(4,5-Dimethyl-1H-benzoimidazol-2-ylmethyl)-phenylcarbamoyl]-pyrrolidine-1-carboxylic acid benzyl ester (Compound 6016)

Using General Procedure D from 30 mg of 3,4-Dimethyl-benzene-1,2-diamine. MS: 483.1 (M+H$^+$)

Example 17

2-[4-(5-Bromo-1H-benzoimidazol-2-ylmethyl)-phenylcarbamoyl]-pyrrolidine-1-carboxylic acid benzyl ester (Compound 6017)

Using General Procedure D from 40 mg of 4-Bromo-benzene-1,2-diamine. MS: 534.1 (M+H$^+$)

Example 18

2-[4-(4-Methyl-1H-benzoimidazol-2-ylmethyl)-phenylcarbamoyl]-pyrrolidine-1-carboxylic acid benzyl ester (Compound 6018)

Using General Procedure D from 30 mg of 3-Methyl-benzene-1,2-diamine. MS: 469.1 (M+H$^+$)

Example 19

2-(4'-Methoxy-biphenyl-4-ylcarbamoyl)-pyrrolidine-1-carboxylic acid benzyl ester (Compound 6019)

Using General Procedure E from 25 mg of 4-Methoxy phenyl boronic acid. Yield 24 mg. MS: 431.1 (M+H$^+$).

Example 20

2-[4-(1H-Naphtho[2,3-d]imidazol-2-ylmethyl)-phenylcarbamoyl]-pyrrolidine-1-carboxylic acid benzyl ester (Compound 6020)

Using General Procedure A from 10 mg of 4-(1H-Naphtho[2,3-d]imidazol-2-ylmethyl)-phenylamine. MS: 505.1 (M+H$^+$).

Example 21

2-(3-Phenoxymethyl-biphenyl-4-ylcarbamoyl)-pyrrolidine-1-carboxylic acid benzyl ester (Compound 6021)

Using General Procedure H from 3-benzyloxyphenyl boronic acid. MS: 507.1 (M+H$^+$).

Example 22

2-(3-Thiophen-2-yl-phenylcarbamoyl)-pyrrolidine-1-carboxylic acid benzyl ester (Compound 6022)

Using General Procedure F from 23 mg of Thiophene-2-boronic acid. Yield 18 mg.
MS: 407.1 (M+H$^+$).

Example 23

2-(4-Thiophen-2-yl-phenylcarbamoyl)-pyrrolidine-1-carboxylic acid benzyl ester (Compound 6023)

Using General Procedure E from 22 mg of Thiophene-2-boronic acid. MS: 407.1 (M+H$^+$)

Example 24

2-[3-Phenoxy-5-(pyridine-3-yloxy)-phenylcarbamoyl]-pyrrolidine-1-carboxylic acid benzyl ester (Compound 6024)

Using General Procedure G from 10 mfg of 3-Phenoxy-5-(pyridine-3-yloxy)-phenylamine in 1 mL of solution. MS: 510.1 (M+H$^+$).

Example 25

2-[4-(5-Furan-2-yl-[1,3,4]oxadiazol-2-yl)-phenylcarbamoyl]-pyrrolidine-1-carboxylic acid benzyl ester (Compound 6025)

Using General Procedure A from 10 mg of 4-(5-Furan-2-yl-[1,3,4]oxadiazol-2-yl)-phenylamine. MS: 459.1 (M+H$^+$).

Example 26

(S)-2-(2',3'-Dimethoxy-biphenyl-4-ylcarbamoyl)-pyrrolidine-1-carboxylic acid benzyl ester (Compound 6026)

Using General Procedure F from 30 mg of 2,3-Dimethoxy phenyl boronic acid.
Yield 24 mg. MS: 461.1 (M+H$^+$).

Example 27

2-{3-[4[(Toluene-4-sulfonyl)-phenoxy]-phenylcarbamoyl}-pyrrolidine-1-carboxylic acid benzyl ester (Compound 6027)

Using General Procedure G from 10 mg of 3-[4-(Toluene-3-sulfonyl)-phenoxy]-phenylamine in 1 mL of solution. MS: 571.1 (M+H$^+$).

Example 28

2-(2,3-Dimethoxy-biphenyl-4-ylcarbamoyl)-pyrrolidine-1-carboxylic acid benzyl ester (Compound 6028)

Using General Procedure H from 18.7 mg of 2,3-dimethoxyphenyl boronic acid.
MS: 461.1 (M+H$^+$).

Example 29

2-(3',4'-Dimethoxybiphenyl-3-yl-carbamoyl)-pyrrolidine-1-carboxylic acid benzyl ester (Compound 6029)

Using General Procedure F from 30 mg of 2,6-Dimethoxy phenyl boronic acid.
Yield 16 mg. MS: 461.1 (M+H$^+$).

Example 30

2-[4-(6-Methoxy-benzothiazol-2-ylcarbamoyl)-phenylcarbamoyl]-pyrrolidine-1-carboxylic acid benzyl ester (Compound 6030)

Using General Procedure A from 10 mg of 4-Amino-N-(6-methoxy-benzothiazol-2-yl)-benzamide. MS: 531.1 (M+H$^+$).

Example 31

2-(2'-Methoxybiphenyl-3-yl-carbamoyl)-pyrrolidine-1-carboxylic acid benzyl ester (Compound 6031)

Using General Procedure F from 25 mg of 2-Methoxy phenyl boronic acid. Yield 30 mg. MS: 431.1 (M+H$^+$).

Example 32

2-[3-Nitro-5-(6,7,8,9-tetrahydro-dibenzofuran-2-yloxy)-phenylcarbamoyl]-pyrrolidine-1-carboxylic acid benzyl ester (Compound 6032)

Using General Procedure G from 10 mg of 3-nitro-5-(6,7,8,9-tetrahydro-dibenzofuran-2-yloxy)-phenylamine in 1 mL of solution. MS: 556.1 (M+H$^+$).

Example 33

2-(2',6'-Dimethoxybiphenyl-3-yl-carbamoyl)-pyrrolidine-1-carboxylic acid benzyl ester (Compound 6033)

Using General Procedure F from 30 mg of 2,6-Dimethoxy phenyl boronic acid.
Yield 24 mg. MS: 461.1 (M+H$^+$).

Example 34

2-(3-Phenoxy-phenylcarbamoyl)-pyrrolidine-1-carboxylic acid benzyl ester (Compound 6034)

Using General Procedure G from 30 mg of 3-Phenoxy-phenylamine in 2 mL of solution. MS: 417.7 (M+H$^+$).

Example 35

2-(Biphenyl-4-ylcarbamoyl)-pyrrolidine-1-carboxylic acid benzyl ester (Compound 6035)

Using General Procedure C from 0.085 g (0.5 mmol) of Biphenyl-4-ylamine. MS: 401.1 (M+H$^+$)

Example 36

2-(2',6'-Dimethoxy-biphenyl-4-ylcarbamoyl)-pyrrolidine-1-carboxylic acid benzyl ester (Compound 6036)

Using General Procedure E from 30 mg of 2,6-Dimethoxy phenyl boronic acid.
Yield 28 mg. MS: 461.1 (M+H$^+$).

Example 37

2-(4'-Methoxybiphenyl-3-yl-carbamoyl)-pyrrolidine-1-carboxylic acid benzyl ester (Compound 6037)

Using General Procedure F from 25 mg of 4-Methoxy phenyl boronic acid. Yield 25 mg. MS: 431.1 (M+H$^+$).

Example 38

2-[4-(1H-Benzoimidazol-2-ylmethyl)-phenylcarbamoyl]-pyrrolidine-1-carboxylic acid benzyl ester (Compound 6038)

Using General Procedure A from 10 mg of 4-(1H-Benzoimidazol-2-ylmethyl)-phenylamine. MS: 455.1 (M+H$^+$).

Example 39

2-(3-Nitro-5-m-tolyloxy-phenylcarbamoyl)-pyrrolidine-1-carboxylic acid benzyl ester (Compound 6039)

Using General Procedure G from 10 mg of 3-Nitro-5-m-tolyloxy-phenylamine in 1 mL of solution. MS: 476.7 (M+H$^+$).

Example 40

2-[4-(3-Ethyl-2,6-dioxo-piperidin-3-yl)-phenylcarbamoyl]-pyrrolidine-1-carboxylic acid benzyl ester (Compound 6040)

Using General Procedure C from 0.116 g (0.5 mmol) of 3-(4-Amino-phenyl)-3-ethyl-piperidine-2,6-dione. MS: 464.1 (M+H$^+$).

Example 41

2-(Benzothiazol-6-ylcarbamoyl)-pyrrolidine-1-carboxylic acid benzyl ester (Compound 6041)

Using General Procedure C from 0.075 g (0.5 mmol) of Benzothiazol-6-ylamine.
MS: 382.1 (M+H$^+$).

Example 42

(S)-2-(4'-Aminomethyl-biphenyl-3-yl carbamoyl)-pyrrolidine-1-carboxylic acid benzyl ester (Compound 6042)

Using General Procedure J from 45 mg of 4-benzylamino phenyl boronic acid. Yield 9.7 mg. MS: 430.1 (M+H$^+$); H$^1$-NMR (DMSO-d$_6$): δ (ppm) 10.15 (s, 1H), 8.15 (m, 2H), 8.01 (s, 1H), 7.67-7.06 (m, 10H), 5.1-4.9 (m, 2H), 4.38 (m, 1H) 4.09 (m, 2H), 3.5 (m, 2H), 2.22 (m, 1H), 1.92 (m, 3H).

Example 43

(S)-2-(3-Benzo[1,3]dioxol-5-yl-phenylcarbamoyl)-pyrrolidine-1-carboxylic acid benzyl ester (Compound 6043)

Using General Procedure J from 33 mg of 3,4-methylenedioxyphenylboronic acid.
Yield 27.7 mg. MS: 445.1 (M+H$^+$); H$^1$-NMR (DMSO-d$_6$): δ (ppm) 10.05 (s, 1H), 7.84 (m, 1H), 7.48 (m, 1H), 7.35-6.98 (m, 10H), 6.05 (s, 2H), 5.1-4.9 (m, 2H), 4.38 (m, 1H), 3.5 (m, 2H), 2.22 (m, 1H), 1.92 (m, 3H).

Example 44

(S)-2-(3-Naphthalen-2-yl-phenylcarbamoyl)-pyrrolidine-1-carboxylic acid benzyl ester (Compound 6044)

Using General Procedure J from 35 mg of Naphthalene-2-boronic acid. Yield 19.4 mg. MS: 451.1 (M+H$^+$); H$^1$-NMR (DMSO-d$_6$): δ (ppm) 10.15 (s, 1H), 8.12-7.92 (m, 5H), 7.75 (m, 1H), 7.56-7.43 (m, 5H), 7.37 (m, 2H), 7.24 (m, 1H), 7.09 (m, 2H), 5.1-4.9 (m, 2H), 4.38 (m, 1H), 3.5 (m, 2H), 2.22 (m, 1H), 1.92 (m, 3H).

Example 45

(S)-2-(4'-Dimethylamino-biphenyl-3-ylcarbamoyl)-pyrrolidine-1-carboxylic acid benzyl ester (Compound 6045)

Using General Procedure J from 33 mg of 4-Dimethylaminohenylboronic acid. Yield 44.4 mg. MS: 444.1 (M+H$^+$); H$^1$-NMR (DMSO-d$_6$): δ (ppm) 10.03 (s, 1H), 7.82 (m, 1H), 7.46-7.03 (m, 10H), 6.80 (m, 2H) 5.1-4.9 (m, 2H), 4.38 (m, 1H), 3.5 (m, 2H), 2.94 (s, 6H), 2.22 (m, 1H), 1.92 (m, 3H).

Example 46

(S)-2-(4'-Methanesulfonyl-biphenyl-3-ylcarbamoyl)-pyrrolidine-1-carboxylic acid benzyl ester (Compound 6046)

Using General Procedure J from 42.5 mg of 1-Methanesulfonyl-4-phenyl boronic acid. Yield 18 mg. MS: 479.1 (M+H$^+$); H$^1$-NMR (DMSO-d$_6$): δ (ppm) 10.15 (s, 1H), 8.04 (m, 3H), 7.83 (m, 2H), 7.60 (m, 1H), 7.49 (m, 2H), 7.36 (m, 2H), 7.22 (m, 1H), 7.08 (m, 2H), 5.1-4.9 (m, 2H), 4.38 (m, 1H), 3.5 (m, 2H), 3.25 (s, 3H), 2.22 (m, 1H), 1.92 (m, 3H).

Example 47

(S)-2-(3-Bromo-phenylcarbamoyl)-pyrrolidine-1-carboxylic acid benzyl ester (Compound 6047)

Z-protected proline (6.22 g) was dissolved in DMF (50 mL) and treated with HATU (1.1 eq. 10.5 g) and DIEA (2.1 eq, 9.6 mL) and stirred for 15 minutes. Then 3-bromoaniline (1 eq, 2.72 mL) was added and the mixture stirred at ambient temperature overnight. The solvent was removed and the mixture purified on a silica gel column eluting with 0-100% EtOAc in hexanes. The solvents were removed and the syrup crystallized with trituration with methanol (10 mL). Yield 8.2 g. MS: 403.1 (M+H$^+$); H$^1$-NMR (DMSO-d$_6$): δ (ppm) 10.19 (s, 1H), 7.92 (m, 1H), 7.46-7.01 (m, 8H), 5.1-4.9 (m, 2H), 4.4 (m, 1H), 3.5 (m, 2H), 2.28 (m, 1H), 1.92 (m, 3H).

Example 48

(S)-2-[3-(5-Acetyl-thiophen-2-yl)-phenylcarbamoyl]-pyrrolidine-1-carboxylic acid benzyl ester (Compound 6048)

Using General Procedure J from 35 mg of 5-Acetyl-thiophene-2-boronic acid. Yield 30.6 mg. MS: 443.1 (M+H$^+$); H$^1$-NMR (DMSO-d$_6$): δ (ppm) 10.19 (s, 1H), 8.02-7.95 (m, 2H), 7.56-7.01 (m, 11H), 5.1-4.9 (m, 2H), 4.4 (m, 1H), 3.5 (m, 2H), 2.28 (m, 1H), 2.08 (s, 3H), 1.92 (m, 3H).

Example 49

2-{4-[2-(2-Chloro-phenylcarbamoyl)-acetyl]-phenylcarbamoyl}-pyrrolidine-1-carboxylic acid benzyl ester (Compound 6049)

Using General Procedure C from 0.144 g (0.5 mmol) of 3-(4-Amino-phenyl)-N-(2-chloro-phenyl)-3-oxo-propionamide. MS: 520.1 (M+H$^+$).

Example 50

2-(4-Piperidin-1-yl-phenylcarbamoyl)-pyrrolidine-1-carboxylic acid benzyl ester (Compound 6050)

Using General Procedure C from 0.088 g (0.5 mmol) of 4-Piperidin-1-yl-phenylamine. MS: 408.1 (M+H$^+$).

Example 51

(S)-2-[3-(1-Methyl-1H-indol-5-yl)-phenylcarbamoyl]-pyrrolidine-1-carboxylic acid benzyl ester (Compound 6051)

Using General Procedure J from 36.5 mg of 1 Methyl-1H-indole 5 boronic acid.
Yield 12.8 mg. MS: 454.1 (M+H$^+$); H$^1$-NMR (DMSO-d$_6$): δ (ppm) 10.05 (s, 1H), 7.94 (m, 1H), 7.75 (s, 1H), 7.50-7.07 (m, 10H), 6.47 (d, 1H, J=3 Hz), 5.1-4.9 (m, 2H), 4.38 (m, 1H), 3.81 (s, 3H), 3.5 (m, 2H), 2.22 (m, 1H), 1.92 (m, 3H).

Example 52

(S)-2-(4'-Acetyl-biphenyl-3-ylcarbamoyl)-pyrrolidine-1-carboxylic acid benzyl ester (Compound 6052)

Using General Procedure J from 33 mg of 4-Acetylphenylboronic acid. Yield 47.4 mg. MS: 443.1 (M+H$^+$); H$^1$-NMR (DMSO-d$_6$): δ (ppm) 10.17 (s, 1H), 8.02 (m, 3H), 7.75 (m, 2H), 7.59 (m, 1H), 7.43-7.37 (m, 4H), 7.22 (m, 1H), 7.06 (m, 1H), 5.1-4.9 (m, 2H), 4.4 (m, 1H), 3.5 (m, 2H), 2.61 (s, 3H), 2.28 (m, 1H), 1.92 (m, 3H).

Example 53

(S)-2-(4'-Nitro-biphenyl-3-ylcarbamoyl)-pyrrolidine-1-carboxylic acid benzyl ester (Compound 6053)

Using General Procedure J from 38 mg of 4-Nitro-phenylboronic acid. Yield 10.4 mg. MS: 446.1 (M+H$^+$); H$^1$-NMR (DMSO-d$_6$): δ (ppm) 10.15 (s, 1H), 8.33 (m, 2H), 8.09 (m, 1H), 7.87 (m, 2H), 7.88 (m, 2H), 7.61 (m, 1H), 7.43 (m, 2H), 7.35 (m, 2H), 7.22 (m, 1H), 7.08 (m, 2H), 5.1-4.9 (m, 2H), 4.39 (m, 1H), 3.5 (m, 2H), 2.22 (m, 1H), 1.92 (m, 3H).

Example 54

(S)-2-(3'-Amino-biphenyl-3-ylcarbamoyl)-pyrrolidine-1-carboxylic acid benzyl ester (Compound 6054)

Using General Procedure J from 33 mg of 3-Aminophenylboronic acid. Yield 20.6 mg. MS: 416.1 (M+H$^+$); H$^1$-NMR (DMSO-d$_6$): δ (ppm) 10.03 (s, 1H), 8.12 (m, 1H), 7.82 (m, 1H), 7.56-7.03 (m, 11H), 5.1-4.9 (m, 2H), 4.38 (m, 1H), 3.5 (m, 2H), 2.22 (m, 1H), 1.92 (m, 3H).

Example 55

(S)-2-[4'-(2-Carboxy-vinyl)-biphenyl-3-ylcarbamoyl]-pyrrolidine-1-carboxylic acid benzyl ester (Compound 6055)

Using General Procedure J from 40.5 mg of 4-(2-Carboxy-vinyl)-phenylboronic acid. Yield 10.3 mg. MS: 446.1 (M+H$^+$); H$^1$—NMR (DMSO-d$_6$): δ (ppm) 10.15 (s, 1H), 7.99 (m, 1H), 7.80 (m, 2H), 7.64-7.55 (m, 4H), 7.37-7.3 (m, 5H), 7.23 (m, 1H), 7.07 (m, 2H), 6.59 (d, 2H, J=14.4 Hz), 5.1-4.9 (m, 2H), 4.39 (m, 1H), 3.5 (m, 2H), 2.22 (m, 1H), 1.92 (m, 3H).

Example 56

(S)-2-(4'-Acetylamino-biphenyl-3-ylcarbamoyl)-pyrrolidine-1-carboxylic acid benzyl ester (Compound 6056)

Using General Procedure K from 37 mg of 1-Bromo 4-Acetamidobenzene. Yield 8.0 mg. MS: 457.1 (M+H$^+$); H$^1$-NMR (DMSO-d$_6$): δ (ppm) 10.15 (s, 1H), 10.03 (s, 1H), 7.84 (m, 1H), 7.68-7.37 (m, 10H), 7.20 (m, 1H), 7.10 (m, 1H), 5.1-4.9 (m, 2H), 4.38 (m, 1H), 3.5 (m, 2H), 2.22 (m, 1H), 2.06 (s, 3H), 1.92 (m, 3H).

Example 57

(S)-2-(3'-Acetylamino-biphenyl-3-ylcarbamoyl)-pyrrolidine-1-carboxylic acid benzyl ester (Compound 6057)

Using General Procedure J from 37 mg of 3-Acetamidophenylboronic acid. Yield 32.0 mg. MS: 414.1 (M-NH-COCH$_3$); H$^1$-NMR (DMSO-d$_6$): δ (ppm) 10.15 (s, 1H), 10.03 (s, 1H), 7.94 (m, 1H), 7.84 (s, 1H), 7.58-7.07 (m, 11H), 5.1-4.9 (m, 2H), 4.38 (m, 1H), 3.5 (m, 2H), 2.22 (m, 1H), 2.06 (s, 3H), 1.92 (m, 3H).

Example 58

2-[4-(4-Methyl-piperazin-1-yl)-phenylcarbamoyl]-pyrrolidine-1-carboxylic acid benzyl ester (Compound 6058)

Using General Procedure C from 0.096 g (0.5 mmol) of 4-(4-Methyl-piperazin-1-yl)-phenylamine. MS: 464.1 (M+H$^+$).

Example 59

2-(4-Bromo-2-fluoro-phenylcarbamoyl)-pyrrolidine-1-carboxylic acid benzyl ester (Compound 6059)

Using General Procedure C from 0.095 g (0.5 mmol) of 4-Bromo-2-fluoro-phenylamine. MS: 404.1 (M+H$^+$).

Example 60

2-[4-(4-Ethylamino-6-isopropylamino-[1,3,5]triazin-2-ylsulfamoyl)-phenylcarbamoyl]-pyrrolidine-1-carboxylic acid benzyl ester (Compound 6060)

Using General Procedure A from 10 mg of 4-Amino-N-(4-ethylamino-6-isopropylamino-[1,3,5]triazin-2-yl)-benzenesulfonamide. MS: 583.1 (M+H$^+$).

Example 61

2-([1,1';4',1'']Terphenyl-4-ylcarbamoyl)-pyrrolidine-1-carboxylic acid benzyl ester (Compound 6061)

Using General Procedure H from 16.0 mg of 4-biphenyl boronic acid. MS: 477.1 (M+H$^+$)

Example 62

2-(4-Morpholin-4-yl-phenylcarbamoyl)-pyrrolidine-1-carboxylic acid benzyl ester (Compound 6062)

Using General Procedure C from 0.089 g (0.5 mmol) of 4-Morpholin-4-yl-phenylamine. MS: 410.1 (M+H$^{30}$).

Example 63

2-(2-Fluoro-4-iodo-phenylcarbamoyl)-pyrrolidine-1-carboxylic acid benzyl ester (Compound 6063)

Using General Procedure C from 0.119 g (0.5 mmol) of 2-Fluoro-4-iodo-phenylamine. MS: 469.1 (M+H$^+$).

Example 64

2-[4-(4-Methyl-pyridin-2-ylsulfamoyl)-phenylcarbamoyl]-pyrrolidine-1-carboxylic acid benzyl ester (Compound 6064)

Using General Procedure A from 10 mg of (S)-2-[4-(4-Methyl-pyridin-2-ylsulfamoyl)-phenylcarbamoyl]-pyrrolidine-1-carboxylic acid benzyl ester. MS: 495.1 (M+H$^+$).

Example 65

2-[3-(5-Chloro-pyridin-3-yloxy)-5-nitro-phenylcarbamoyl]-pyrrolidine-1-carboxylic acid benzyl ester (Compound 6065)

Using General Procedure G from 10 mg of 2-(2-aminothiazol-4-ylmethyl)-isoindole-1,3-dione in 1 mL of solution. MS: 491.1 (M+H$^+$)

Example 66

2-[3-(Quinazolin-4-ylamino)-phenylcarbamoyl]-pyrrolidine-1-carboxylic acid benzyl ester (Compound 6066)

Using General Procedure G from 10 mg of N-quinazolin-4-yl-benzene-1,3-diamine in 1 mL of solution. MS: 468.1 (M+H$^+$)

Example 67

2-[4-(5-Cyano-1H-benzoimidazol-2-ylmethyl)-phenylcarbamoyl]-pyrrolidine-1-carboxylic acid benzyl ester (Compound 6067)

Using General Procedure D from 30 mg of 3,4-Diaminobenzonitrile. MS: 483.1 (M+H$^+$)

Example 68

2-(3-Oxo-1,3-dihydro-isobenzofuran-5-ylcarbamoyl)-pyrrolidine-1-carboxylic acid benzyl ester (Compound 6068)

Using General Procedure C from 0.075 g (0.5 mmol) of 6-Amino-3H-isobenzofuran-1-one. MS: 381.1 (M+H$^+$).

Example 69

2-[4-(Morpholine-4-carbonyl)-phenylcarbamoyl]-pyrrolidine-1-carboxylic acid benzyl ester (Compound 6069)

Using General Procedure A from 10 mg of (4-Aminophenyl)-morpholin-4-yl-methanone. MS: 438.1 (M+H$^+$).

Example 70

2-(3-Pyridin-4-yl-phenylcarbamoyl)-pyrrolidine-1-carboxylic acid benzyl ester (Compound 6070)

Using General Procedure F from 21 mg of Pyridine-4-boronic acid. Yield 12 mg.
MS: 402.1 (M+H$^+$).

Example 71

2-(4-Benzothiazol-2-yl-phenylcarbamoyl)-pyrrolidine-1-carboxylic acid benzyl ester (Compound 6071)

Using General Procedure A from 10 mg of 4-Benzothiazol-2-yl-phenylamine. MS: 458.1 (M+H$^+$)

Example 72

2-[3-(2-Morpholin-4-yl-2-oxo-ethoxy)-phenylcarbamoyl]-pyrrolidine-1-carboxylic acid benzyl ester (Compound 6072)

Using General Procedure G from 10 mg of 2-(3-aminophenoxy)-1-morpholin-4-yl-ethanone in 1 mL of solution. MS: 468.1 (M+H$^+$)

Example 73

2-(4-Morpholin-4-ylmethyl-phenylcarbamoyl)-pyrrolidine-1-carboxylic acid benzyl ester (Compound 6073)

Using General Procedure A from 10 mg of 4-Morpholin-4-ylmethyl-phenylamine.
MS: 424.1 (M+H$^+$).

Example 74

2-[3-(4-Nitro-phenoxy)-phenylcarbamoyl]-pyrrolidine-1-carboxylic acid benzyl ester (Compound 6074)

Using General Procedure G from 10 mg of 3-(4-nitrophenoxy)-phenylamine in 1 mL of solution. MS: 462.2 (M+H$^+$)

Example 75

2-[4-(5-tert-Butyl-1H-benzoimidazol-2-ylmethyl)-phenylcarbamoyl]-pyrrolidine-1-carboxylic acid benzyl ester (Compound 6075)

Using General Procedure D from 35 mg of 4-tert-Butyl-benzene-1,2-diamine. MS: 483.1 (M+H$^+$).

Example 76

2-(4-Bromo-phenylcarbamoyl)-pyrrolidine-1-carboxylic acid benzyl ester (Compound 6076)

Using General Procedure C from 0.075 g (0.5 mmol) of 4-Bromo-phenylamine. MS: 404.1 (M+H$^+$).

Example 77

2-(4-Pyrrolidin-1-ylmethyl-phenylcarbamoyl)-pyrrolidine-1-carboxylic acid benzyl ester (Compound 6077)

Using General Procedure A from 10 mg of 4-Pyrrolidin-1-ylmethyl-phenylamine.
MS: 408.1 (M+H$^+$).

Example 78

2-(2'-Methoxy-biphenyl-4-ylcarbamoyl)-pyrrolidine-1-carboxylic acid benzyl ester (Compound 6078)

Using General Procedure E from 25 mg of 2-Methoxy phenyl boronic acid. Yield 19 mg. MS: 431.1 (M+H$^+$).

Example 79

2-(4-pyridin-4-yl-phenylcarbamoyl)-pyrrolidine-1-carboxylic acid benzyl ester (Compound 6079)

Using General Procedure H from 18.3 mg of pyridine-4-boronic acid. MS: 402.1 (M+H$^+$)

Example 80

2-[4-(Piperidine-1-carbonyl)-phenylcarbamoyl]-pyrrolidine-1-carboxylic acid benzyl ester (Compound 6080)

Using General Procedure A from 10 mg of 4-Amino-phenyl)-piperidin-1-yl-methanone. MS: 436.1 (M+H$^+$).

Example 81

(S)-2-(3-Quinolin-3-yl-phenylcarbamoyl)-pyrrolidine-1-carboxylic acid benzyl ester (Compound 6081)

Using General Procedure K from 51.5 mg of 3-Bromo-quinoline. Yield 24.9 mg.
MS: 452.1 (M+H$^+$); H$^1$-NMR (DMSO-d$_6$): δ (ppm) 10.22 (s, 1H), 9.23 (m, 1H), 8.68 (m, 1H), 8.1 (m, 3H), 7.82 (m, 1H), 7.71-7.42 (m, 6H), 7.37-7.07 (m, 3H), 5.1-4.9 (m, 2H), 4.38 (m, 1H), 3.5 (m, 2H), 2.22 (m, 1H), 2.06 (s, 3H).

Example 82

(S)-2-[3-(1H-Indol-4-yl)-phenylcarbamoyl]-pyrrolidine-1-carboxylic acid benzyl ester (Compound 6082)

Using General Procedure K from 49 mg of 4-Bromo-1H-indole. Yield 5.2 mg. MS: 440.1 (M+H$^+$); H$^1$-NMR (DMSO-d$_6$): δ (ppm) 11.23 (s, 1H), 10.15 (s, 1H), 7.99 (s, 1H), 7.54-7.04 (m, 12H), 6.59 (m, 1H), 5.1-4.9 (m, 2H), 4.38 (m, 1H), 3.5 (m, 2H), 2.22 (m, 1H), 2.06 (s, 3H).

Example 83

(S)-2-[3-(2-Oxo-2,3-dihydro-1H-indol-5-yl)-phenylcarbamoyl]-pyrrolidine-1-carboxylic acid benzyl ester (Compound 6083)

Using General Procedure K from 53 mg of 5-Bromo-1,3-dihydro-indol-2-one. Yield 5.6 mg. MS: 456.1 (M+H$^+$); H$^1$-NMR (DMSO-d$_6$): δ (ppm) 10.48 (s, 1H), 10.08 (s, 1H), 7.93 (m, 1H), 7.61-7.53 (m, 3H), 7.44-7.20 (m, 6H), 7.03 (m, 1H), 6.88 (m, 1H), 5.1-4.9 (m, 2H), 4.38 (m, 1H), 3.54 (s, 2H), 3.5 (m, 2H), 2.22 (m, 1H), 2.06 (s, 3H).

Example 84

(S)-2-[3-(2,3-Dioxo-2,3-dihydro-1H-indol-5-yl)-phenylcarbamoyl]-pyrrolidine-1-carboxylic acid benzyl ester (Compound 6084)

Using General Procedure K from 56 mg of 5-Bromo-1H-indole-2,3-dione. Yield 15.1 mg. MS: 470.1 (M+H); H$^1$-NMR (DMSO-d$_6$): δ (ppm) 11.13 (s, 1H), 10.11 (s, 1H), 7.91 (m, 1H), 7.95 (m, 1H), 7.65-7.50 (m, 9H), 7.35-6.99 (m, 2H), 5.1-4.9 (m, 2H), 4.38 (m, 1H), 3.5 (m, 2H), 2.22 (m, 1H), 2.06 (s, 3H).

Example 85

(S)-2-[3-(2-Methyl-quinolin-6-yl)-phenylcarbamoyl]-pyrrolidine-1-carboxylic acid benzyl ester (Compound 6085)

Using General Procedure K from 55.5 mg of 6-Bromo-2-methyl-quinoline. Yield 14.7 mg. MS: 466.1 (M+H$^+$); H$^1$-NMR (DMSO-d$_6$): δ (ppm) 10.22 (s, 1H), 8.73 (m, 1H), 8.35 (d, 1H, J=6 Hz), 8.16 (m, 3H), 7.73 (m, 1H), 7.61-7.49 (m, 4H), 7.35 (m, 2H), 7.22 (m, 1H), 7.08 (m, 1H), 5.1-4.9 (m, 2H), 4.38 (m, 1H), 3.5 (m, 2H), 2.82 (s. 3H), 2.22 (m, 1H), 2.06 (s, 3H).

Example 86

(S)-2-(4'-Amino-biphenyl-3-ylcarbamoyl)-pyrrolidine-1-carboxylic acid benzyl ester (Compound 6086)

A solution of (S)-2-(3-Bromo-phenylcarbamoyl)-pyrrolidine-1-carboxylic acid benzyl ester (201 mg, 0.5 mmol), 6-4-(4,4,5,5-Tetramethyl-[1,3,2]dioxaborolan-2-yl)-phenylamine (1 eq., 108 mg), Pd[P(Ph)$_3$]$_4$ (5 mol %, 20 mg), in methanol (6 mL), NaHCO$_3$ (sat. aq., 900 uL) and DMF (1.5 mL) was degassed and heated to 70° C. overnight in a sealed vial. The reaction was cooled, filtered and the solvents removed. The resulting mixture was redissolved in 5 ml of 90% DMF, 10% water with 0.1% TFA and purified by reverse phase HPLC to give the products. Yield 26 mg. MS: 440.3 (M+H). H$^1$-NMR (DMSO-d$_6$): δ (ppm) 10.1 (s, 1H), 7.9 (m, 1H), 7.5-7.0 (m, 12H), 5.0 (m, 2H), 4.4 (m, 1H), 3.5 (m, 1H), 2.2 (m, 1H), 1.9 (m, 3H).

Example 87

(S)-2-(3'-Acetyl-biphenyl-3-ylcarbamoyl)-pyrrolidine-1-carboxylic acid benzyl ester (Compound 6087)

Prepared similar to Compound 6097 with 1-(3-Bromo-phenyl)-ethanone. Yield 42.3 mg. MS: 443.3 (M+H). H$^1$-NMR (DMSO-d$_6$): δ (ppm) 10.1 (s, 1H), 8.1-7.0 (m, 12H), 5.0 (m, 2H), 4.4 (m, 1H), 3.5 (m, 1H), 2.6 (s, 3H), 2.2 (m, 1H), 1.9 (m, 3H).

Example 88

(S)-2-[3-(6-Hydroxy-naphthalen-2-yl)-phenylcarbamoyl]-pyrrolidine-1-carboxylic acid benzyl ester (Compound 6088)

Prepared similar to Compound 6097 with 6-Bromo-naphthalen-2-ol. Yield 8.1 mg.
MS: 467.3 (M+H). H$^1$-NMR (DMSO-d$_6$): δ (ppm) 10.1 (s, 1H), 9.8 (bs, 1H), 8.0-7.0 (m, 15H), 5.0 (m, 2H), 4.4 (m, 1H), 3.5 (m, 1H), 2.2 (m, 1H), 1.9 (m, 3H).

Example 89

(S)-2-(3'-Methylamino-biphenyl-3-ylcarbamoyl)-pyrrolidine-1-carboxylic acid benzyl ester (Compound 6089)

Prepared similar to Compound 6097 with (3-Bromo-phenyl)-methyl-amine. Yield 22.4 mg. MS: 430.3 (M+H). $H^1$-NMR (DMSO-$d_6$): δ (ppm) 10.1 (s, 1H), 7.9 (m, 1H), 7.5-6.9 (m, 11H), 6.7 (m, 1H), 5.0 (m, 2H), 4.4 (m, 1H), 3.5 (m, 1H), 2.7 (s, 3H), 2.2 (m, 1H), 1.9 (m, 3H).

Example 90

(S)-2-(3'-Amino-2'-methyl-biphenyl-3-ylcarbamoyl)-pyrrolidine-1-carboxylic acid benzyl ester (compound 6090)

Prepared similar to Compound 6097 with 3-Bromo-2-methyl-phenylamine. Yield 22.3 mg. MS: 430.3 (M+H). $H^1$-NMR (DMSO-$d_6$): δ (ppm) 10.1 (s, 1H), 9.9 (d, 1H), 7.8 (s, 1H), 7.7-7.0 (m, 11H), 5.8 (bs, 2H), 5.0 (m, 2H), 4.4 (m, 1H), 3.5 (m, 1H), 2.2 (m, 1H), 2.1 (s. 3H), 1.9 (m, 3H).

Example 91

(S)-2-[3-(2-Methyl-benzothiazol-5-yl)-phenylcarbamoyl]-pyrrolidine-1-carboxylic acid benzyl ester (Compound 6091)

Prepared similar to Compound 6097 with 5-Bromo-2-methyl-benzothiazole. Yield 12.4 mg. MS: 471.3 (M+H). $H^1$-NMR (DMSO-$d_6$): δ (ppm) 11.1 (s, 1H), 10.1 (s, 1H), 8.0 (m, 1H), 8.0-6.9 (m, 12H), 5.0 (m, 2H), 4.4 (m, 1H), 3.5 (m, 1H), 2.75 (s. 3H), 2.2 (m, 1H), 1.9 (m, 3H).

Example 92

(S)-2-(3'-Hydroxy-biphenyl-3-ylcarbamoyl)-pyrrolidine-1-carboxylic acid benzyl ester (Compound 6092)

Prepared similar to Compound 6097 with 3-Bromo-phenol. Yield 26.7 mg. MS: 484.3 (M+H). $H^1$-NMR (DMSO-$d_6$): δ (ppm) 10.1 (s, 1H), 7.5-6.9 (m, 11H), 6.7 (d, 1H), 5.0 (m, 2H), 4.4 (m, 1H), 3.5 (m, 1H), 2.2 (m, 1H), 1.9 (m, 3H).

Example 93

(S)-2-(3'-Ureido-biphenyl-3-ylcarbamoyl)-pyrrolidine-1-carboxylic acid benzyl ester (Compound 6093)

Prepared similar to Compound 6097 with (3-Bromo-phenyl)-urea. Yield 22.0 mg.
MS: 459.3 (M+H). $H^1$-NMR (DMSO-$d_6$): δ (ppm) 10.1 (s, 1H), 8.6 (m, 1H), 7.9-7.0 (m, 13H), 5.8 (bs, 2H), 5.0 (m, 2H), 4.4 (m, 1H), 3.5 (m, 1H), 2.2 (m, 1H), 1.9 (m, 3H).

Example 94

(S)-2-[3-(1H-Indol-7-yl)-phenylcarbamoyl]-pyrrolidine-1-carboxylic acid benzyl ester (Compound 6094)

Prepared similar to Compound 6097 with 7-Bromo-1H-indole. Yield 6.7 mg. MS: 440.3 (M+H). $H^1$-NMR (DMSO-$d_6$): δ (ppm) 10.9 (d, 1H), 10.1 (s, 1H), 7.8-7.0 (m, 14H), 6.5 (m, 1H), 5.0 (m, 2H), 4.4 (m, 1H), 3.5 (m, 1H), 2.2 (m, 1H), 1.9 (m, 3H).

Example 95

(S)-2-(3'-Amino-5'-trifluoromethyl-biphenyl-3-ylcarbamoyl)-pyrrolidine-1-carboxylic acid benzyl ester (Compound 6095)

Prepared similar to Compound 6097 with 3-Bromo-5-trifluoromethyl-phenylamine.
Yield 32.2 mg. MS: 484.3 (M+H). $H^1$-NMR (DMSO-$d_6$): δ (ppm) 10.1 (s, 1H), 7.9 (d, 1H), 7.6-6.9 (m, 11H), 5.0 (m, 2H), 4.4 (m, 1H), 3.5 (m, 1H), 2.2 (m, 1H), 1.9 (m, 3H).

Example 96

(S)-2-(3'-Dimethylamino-biphenyl-3-ylcarbamoyl)-pyrrolidine-1-carboxylic acid benzyl ester (Compound 6096)

Prepared similar to Compound 6097 with (3-Bromo-phenyl)-dimethyl-amine. Yield 18.8 mg. MS: 444.3 (M+H). $H^1$-NMR (DMSO-$d_6$): δ (ppm) 10.1 (s, 1H), 7.8-6.9 (m, 13H), 5.0 (m, 2H), 4.4 (m, 1H), 3.5 (m, 1H), 3.0*s, 6H), 2.2 (m, 1H), 1.9 (m, 3H).

Example 97

(S)-2-[3-(1H-Indol-6-yl)-phenylcarbamoyl]-pyrrolidine-1-carboxylic acid benzyl ester (Compound 6097)

A solution of (S)-2-[3-(4,4,5,5-Tetramethyl-[1,3,2]dioxaborolan-2-yl)-phenylcarbamoyl]-pyrrolidine-1-carboxylic acid benzyl ester (90 mg, 0.2 mmol), 6-Bromo-1H-indole (1 eq., 49 mg), Pd[P(Ph)$_3$]$_4$ (5 mol %, 10 mg), in methanol (4 mL), NaHCO$_3$ (sat. aq., 600 uL) and DMF (800 uL) was degassed and heated to 70° C. overnight in a sealed vial. The reaction was cooled, filtered and the solvents removed. The resulting mixture was redissolved in 5 ml of 90% DMF, 10% water with 0.1% TFA and purified by reverse phase HPLC to give the products. Yield 5.7 mg. MS: 440.3 (M+H). $H^1$-NMR (DMSO-$d_6$): δ (ppm) 11.1 (s, 1H), 10.1 (s, 1H), 8.0 (m, 1H), 7.6-7.2 (m, 12H), 7.0 (m, 2H), 6.4 (m, 1H), 5.0 (m, 2H), 4.4 (m, 1H), 3.5 (m, 1H), 2.2 (m, 1H), 1.9 (m, 3H).

Example 301

(S)-2-(4'-Cyclopropylcarbamoyl-biphenyl-3-ylcarbamoyl)-pyrrolidine-1-carboxylic acid benzyl ester (Compound 6301)

4-Bromo-N-cyclopropyl-benzamide

4-Bromo-benzoic acid (2.5116 g, 12.5 mmol) and HATU (5.2213 g, 13.7 mmol) were dissolved in DMF (40 mL). DIEA (4.572 mL, 26.2 mmol) was added, and the mixture was allowed to stir at ambient temperature for 15 minutes. Then cyclopropylamine (0.866 mL, 12.5 mmol) was added, and the reaction was stirred at ambient temperature overnight. The solvent was removed, and the crude was purified via silica gel chromatography to give the desired product.

(S)-2-(4'-Cyclopropylcarbamoyl-biphenyl-3-ylcarbamoyl)-pyrrolidine-1-carboxylic acid benzyl ester (Compound 6301)

A solution of (S)-2-[3-(4,4,5,5-tetramethyl-[1,3,2]dioxaborolan-2-yl)-phenylcarbamoyl]-pyrrolidine-1-carboxylic acid benzyl ester (74 mg, 0.16 mmol), 4-bromo-N-cyclopropyl-benzamide (39.7 mg, 0.17 mmol), and Pd[P(Ph)$_3$]$_4$ (13.7 mg, 7.2 mol %) in methanol (2 mL), NaHCO$_3$ (sat. aq., 300 µL), and DMF (400 µL) was degassed and heated to 70° C. overnight in a sealed vial. The reaction was cooled, filtered, and purified by reverse phase HPLC to give the desired product. Yield 5.3 mg. MS: 484.2 (M+H$^+$); H$^1$ NMR (DMSO-d$_6$): δ (ppm) 0.51-0.70 (m, 4H), 1.76-1.98 (m, 3H), 2.08-2.30 (m, 1H), 2.77-2.86 (m, 1H), 3.38-3.52 (m, 2H), 4.27-4.37 (m, 1H), 4.86-5.08 (m, 2H), 6.96-7.65 (m, 7

Example 302

(S)-2-[3-(4-Cyclopropylcarbamoyl-thiazol-2-yl)-phenylcarbamoyl]-pyrrolidine-1-carboxylic acid benzyl ester (Compound 6302)

(S)-2-[3-(4,4,5,5-Tetramethyl-[1,3,2]dioxaborolan-2-yl)-phenylcarbamoyl]-pyrrolidine-1-carboxylic acid benzyl ester A solution of (S)-2-(3-Bromo-phenylcarbamoyl)-pyrrolidine-1-carboxylic acid benzyl ester (3 g), 4,4,5,5,4',4',5',5'-Octamethyl-[2,2']bi[[1,3,2]dioxaborolanyl], (5.7 g), KOAc (2.6 g), Pd[P(Ph)$_3$]$_2$Cl$_2$ (600 mg) in DMSO was degassed and heated to 90 deg. C. for 15 hours. The solvents were removed and the mixture separated on silica gel (eluting with EtOAc:Hexanes 0-100%). Yield 2.8 g. MS: 451.2 (M+H$^+$).

(S)-2-[3-(4-Cyclopropylcarbamoyl-thiazol-2-yl)-phenylcarbamoyl]-pyrrolidine-1-carboxylic acid benzyl ester (Compound 6302)

A solution of (S)-2-[3-(4,4,5,5-Tetramethyl-[1,3,2]dioxaborolan-2-yl)-phenylcarbamoyl]-pyrrolidine-1-carboxylic acid benzyl ester (90 mg, 0.2 mmol), 2-Bromo-thiazole-4-carboxylic acid cyclopropylamide (1 eq., 49 mg), Pd[P(Ph)$_3$]$_4$ (5 mol %, 10 mg), in methanol (4 mL), NaHCO$_3$ (sat. aq., 600 uL) and DMF (800 uL) was degassed and heated to 70° C. overnight in a sealed vial. The reaction was cooled, filtered and the solvents removed. The resulting mixture was redissolved in 5 ml of 90% DMF, 10% water with 0.1% TFA and purified by reverse phase HPLC to give the products. Yield 11.1 mg. MS: 491.3 (M+H). H$^1$-NMR (DMSO-d$_6$): δ (ppm) 10.2 (s, 1H), 8.4-8.2 (m, 2H), 7.8-7.0 (m, 10H), 6.5 (m, 2H), 5.1-4.9 (m, 2H), 4.4 (m, 1H), 2.8 (m, 1H), 2.3 (m, 1H), 1.9 (m, 3H), 0.7-0.6 (m, 4H).

Example 303

(S)-2-(3'-Methylaminomethyl-biphenyl-3-ylcarbamoyl)-pyrrolidine-1-carboxylic acid benzyl ester (Compound 6303)

A solution of (S)-2-[3-(4,4,5,5-tetramethyl-[1,3,2]dioxaborolan-2-yl)-phenylcarbamoyl]-pyrrolidine-1-carboxylic acid benzyl ester (89.7 mg, 0.20 mmol), (3-bromo-benzyl)-methyl-amine (43.4 mg, 0.22 mmol), and Pd[P(Ph)$_3$]$_4$ (15.4 mg, 6.7 mol %) in methanol (2 mL), NaHCO$_3$ (sat. aq., 300 µL), and DMF (400 µL) was degassed and heated to 70° C. overnight in a sealed vial. The reaction was cooled, filtered, and purified by reverse phase HPLC to give the desired product. The product was then converted to the HCl salt. After dissolving the product in a minimum amount of acetonitrile and cooling the solution in dry ice, 2.0M HCl in diethyl ether was added until precipitate crashed out of solution. The mixture was centrifuged, and the liquid was decanted. Additional cold diethyl ether was added, and the mixture was again centrifuged and the liquid decanted. The resulting solid was dried to give the HCl salt of the desired product. Yield 5.9 mg. MS: 444.2 (M+H$^+$); H$^1$ NMR (DMSO-d$_6$): δ (ppm) 1.80-2.02 (m, 3H), 2.17-2.35 (m, 1H), 2.53-2.64 (t, 3H), 3.39-3.57 (m, 2H), 4.15-4.23 (t, 2H), 4.33-4.44 (m, 1H), 4.60-5.12 (m, 2H), 7.02-7.76 (m, 12H), 8.06-8.12 (m, 1H), 8.78-8.93 (s, 1H), 10.10-10.25 (s, 1H).

Example 304

(S)-2-(3-Benzothiazol-6-yl-phenylcarbamoyl)-pyrrolidine-1-carboxylic acid benzyl ester (Compound 6304)

A solution of (S)-2-[3-(4,4,5,5-tetramethyl-[1,3,2]dioxaborolan-2-yl)-phenylcarbamoyl]-pyrrolidine-1-carboxylic acid benzyl ester (74 mg, 0.16 mmol), 6-bromo-benzothiazole (34.9 mg, 0.16 mmol), and Pd[P(Ph)$_3$]$_4$ (12.1 mg, 6.4 mol %) in methanol (2 mL), NaHCO$_3$ (sat. aq., 300 µL), and DMF (400 µL) was degassed and heated to 70° C. overnight in a sealed vial. The reaction was cooled, filtered, and purified by reverse phase HPLC to give the desired product. Yield 5.6 mg. MS: 458.1 (M+H$^+$); H$^1$ NMR (DMSO-d$_6$): δ (ppm) 1.18-1.25 (m, 2H), 1.76-2.00 (m, 3H), 2.10-2.34 (m, 1H), 4.28-4.40 (m, 1H), 4.87-5.10 (m, 2H), 7.00-7.56 (m, 7H), 7.68-7.66 (m, 1H), 7.97-8.15 (m, 2H), 8.33-8.39 (m, 1H), 9.35-9.39 (s, 1H), 10.09-10.16 (s, 1H).

Example 305

(S)-2-(4-Cyclopropylcarbamoyl-phenylcarbamoyl)-pyrrolidine-1-carboxylic acid benzyl ester (Compound 6305)

Z-protected (S)-proline (50 mg) was dissolved in DMF (5 mL) and treated with HATU (1.1 eq. 100 mg) and DIEA (2.1 eq, 139 µL) and stirred for 15 minutes. Then 4-amino-N-cyclopropyl-benzamide (1 eq, 34 mg) was added and the mixture stirred at ambient temperature overnight. The reaction was cooled, filtered and the solvents removed. The resulting mixture was redissolved in 5 ml of 90% DMF, 10% water with 0.1% TFA and purified by reverse phase HPLC to give the products. Yield 44 mg. MS: 408.5 (M+H$^+$); H$^1$-NMR (DMSO-d$_6$): δ (ppm) 10.2 (m, 1H), 8.3 (m, 1H), 7.7 (m, 2H), 7.6 (m, 2H), 7.3 (m, 2H), 7.2-7.0 (m, 3H), 5.1-4.8 (m, 2H), 4.4 (m, 1H), 3.45 (m, 2H), 2.8 (m, 1H), 1.9 (m, 4H), 0.71 (m, 4H)

Example 306

(S)-2-(4'-Cyclopropylcarbamoyl-biphenyl-3-ylcarbamoyl)-pyrrolidine-1-carboxylic acid benzyl ester (Compound 6306)

2-(4-Bromo-phenyl)-N-cyclopropyl-acetamide (4-Bromo-phenyl)-acetic acid (632.3 mg, 2.9 mmol) and DCC (609.2 mg, 3.0 mmol) were dissolved in dichloromethane (15 mL) and stirred at ambient temperature for 5 minutes. Then cyclopropylamine (204.5 µL, 3.0 mmol) was added, and the reaction was stirred at ambient temperature overnight. The reaction was filtered, and the solvent was removed. The resulting mixture was redissolved in DMF (10 mL) and purified by reverse phase HPLC to give the desired product.

(S)-2-(4'-Cyclopropylcarbamoyl-biphenyl-3-ylcarbamoyl)-pyrrolidine-1-carboxylic acid benzyl ester (Compound 6306)

A solution of (S)-2-[3-(4,4,5,5-tetramethyl-[1,3,2]dioxaborolan-2-yl)-phenylcarbamoyl]-pyrrolidine-1-carboxylic acid benzyl ester (74 mg, 0.16 mmol), 2-(4-bromo-phenyl)-N-cyclopropyl-acetamide (41.6 mg, 0.16 mmol), and Pd[P(Ph)$_3$]$_4$ (12.7 mg, 6.7 mol %) in methanol (2 mL), NaHCO$_3$ (sat. aq., 300 µL), and DMF (400 µL) was degassed and heated to 70° C. overnight in a sealed vial. The reaction was cooled, filtered, and purified by reverse phase HPLC to give the desired product. Yield 7.1 mg. MS: 498.2 (M+H$^+$); H$^1$-NMR (DMSO-d$_6$): δ (ppm) 0.37-0.44 (m, 2H), 0.58-0.66 (m, 2H), 1.80-2.04 (m, 3H), 2.14-2.36 (m, 1H), 2.55-2.68 (m, 1H), 3.36-3.57 (m, 2H), 4.32-4.43 (m, 1H), 4.91-5.14 (m, 2H), 7.00-7.65 (m, 12H), 7.87-7.95 (m, 1H), 8.12-8.18 (m, 1H), 10.08-10.14 (s, 1H).

Example 307

(S)-2-(3'-Cyano-biphenyl-3-ylcarbamoyl)-pyrrolidine-1-carboxylic acid benzyl ester (Compound 6307)

A solution of (S)-2-[3-(4,4,5,5-tetramethyl-[1,3,2]dioxaborolan-2-yl)-phenylcarbamoyl]-pyrrolidine-1-carboxylic acid benzyl ester (90.4 mg, 0.20 mmol), 3-bromo-benzonitrile (37.5 mg, 0.21 mmol), and Pd[P(Ph)$_3$]$_4$ (15.9 mg, 6.9 mol %) in methanol (2 mL), NaHCO$_3$ (sat. aq., 300 µL), and DMF (400 µL) was degassed and heated to 70° C. overnight in a sealed vial. The reaction was cooled, filtered, and purified by reverse phase HPLC to give the desired product. Yield 11.7 mg. MS: 426.1 (M+H$^+$); H$^1$ NMR (DMSO-d$_6$): δ (ppm) 1.80-2.04 (m, 3H), 2.15-2.36 (m, 1H), 3.39-3.58 (m 2H), 4.32-4.43 (m, 1H), 4.89-5.14 (m, 2H), 7.03-8.07 (m, 13H), 10.13-10.20 (s, 1H).

H), 7.45-7.65 (m, 3H), 7.81-7.97 (m, 3H), 8.40-8.47 (d, 1H), 10.07-10.13 (s, 1H).

Example 308

(S)-2-{4'-[(Cyclopropanecarbonyl-amino)-methyl]-biphenyl-3-ylcarbamoyl}-pyrrolidine-1-carboxylic acid benzyl ester (Compound 6308)

Cyclopropanecarboxylic acid 4-bromo-benzylamide

4-Bromo-benzylamine hydrochloride (367.8 mg, 1.7 mmol) was dissolved in dichloromethane (15 mL), and the solution was cooled to 0° C. DIEA (380 µL, 2.2 mmol) was then added, and the reaction was stirred at 0° C. for 5 minutes. Then cyclopropanecarbonyl chloride (180 µL, 2.3 mmol) was added, and the reaction was stirred at 0° C. for 20 minutes. The reaction was quenched with distilled water, and the solvents were removed. The resulting mixture was redissolved in DMF (10 mL) and purified by reverse phase HPLC to give the desired product.

(S)-2-{4'-[(Cyclopropanecarbonyl-amino)-methyl]-biphenyl-3-ylcarbamoyl}-pyrrolidine-1-carboxylic acid benzyl ester (Compound 6308)

A solution of (S)-2-[3-(4,4,5,5-tetramethyl-[1,3,2]dioxaborolan-2-yl)-phenylcarbamoyl]-pyrrolidine-1-carboxylic acid benzyl ester (93.8 mg, 0.21 mmol), cyclopropanecarboxylic acid 4-bromo-benzylamide (50.6 mg, 0.20 mmol), and Pd[P(Ph)$_3$]$_4$ (13.7 mg, 5.7 mol %) in methanol (2 mL), NaHCO$_3$ (sat. aq., 300 µL), and DMF (400 µL) was degassed and heated to 70° C. overnight in a sealed vial. The reaction was cooled, filtered, and purified by reverse phase HPLC to give the desired product. Yield 15.0 mg. MS: 498.2 (M+H$^+$); H$^1$ NMR (DMSO-d$_6$): δ (ppm) 0.61-0.79 (m, 4H), 1.56-1.69 (m, 3H), 2.11-2.35 (m, 1H), 3.38-3.59 (m, 2H), 4.25-4.43 (m, 3H), 4.89-5.15 (m, 2H), 7.00-7.65 (m, 12H), 7.85-7.95 (m, 1H), 8.51-8.63 (m, 1H), 10.07-10.16 (s, 1H).

Example 309

(S)-2-(3'-Nitro-biphenyl-3-ylcarbamoyl)-pyrrolidine-1-carboxylic acid benzyl ester (Compound 6309)

A solution of (S)-2-[3-(4,4,5,5-tetramethyl-[1,3,2]dioxaborolan-2-yl)-phenylcarbamoyl]-pyrrolidine-1-carboxylic acid benzyl ester (89.7 mg, 0.20 mmol), 1-bromo-3-nitrobenzene (41.3 mg, 0.20 mmol), and Pd[P(Ph)$_3$]$_4$ (15.5 mg, 6.7 mol %) in methanol (2 mL), NaHCO$_3$ (sat. aq., 300 µL), and DMF (400 µL) was degassed and heated to 70° C. overnight in a sealed vial. The reaction was cooled, filtered, and purified by reverse phase HPLC to give the desired product. Yield 7.0 mg. MS: 446.1 (M+H$^+$); H$^1$ NMR (DMSO-d$_6$): δ (ppm) 1.77-2.04 (m, 3H), 2.16-2.47 (m, 1H), 3.38-3.60 (m, 2H), 4.32-4.42 (m, 1H), 4.90-5.13 (m, 2H), 7.02-8.38 (m, 13H), 10.15-10.23 (s, 1H).

Example 310

(S)-2-(3'-Cyclopropylcarbamoyl-biphenyl-3-ylcarbamoyl)-pyrrolidine-1-carboxylic acid benzyl ester (Compound 6310)

3-Bromo-N-cyclopropyl-benzamide

3-Bromo-benzoic acid (2.5518 g, 12.7 mmol) and HATU (5.2230 g, 13.7 mmol) were dissolved in DMF (40 mL). DIEA (4.644 mL, 26.7 mmol) was added, and the mixture was allowed to stir at room temperature for 15 minutes. Then cyclopropylamine (0.88 mL, 12.7 mmol) was added, and the reaction was stirred at ambient temperature overnight. The solvent was removed, and the crude was purified via silica gel chromatography to yield the desired product.

(S)-2-(3'-Cyclopropylcarbamoyl-biphenyl-3-ylcarbamoyl)-pyrrolidine-1-carboxylic acid benzyl ester (Compound 6310)

A solution of (S)-2-[3-(4,4,5,5-tetramethyl-[1,3,2]dioxaborolan-2-yl)-phenylcarbamoyl]-pyrrolidine-1-carboxylic acid benzyl ester (93.7 mg, 0.21 mmol), 3-bromo-N-cyclopropyl-benzamide (50.0 mg, 0.21 mmol), and Pd[P(Ph)$_3$]$_4$ (12.8 mg, 5.3 mol %) in methanol (2 mL), NaHCO$_3$ (sat. aq., 300 µL), and DMF (400 µL) was degassed and heated to 70° C. overnight in a sealed vial. The reaction was cooled, filtered, and purified by reverse phase HPLC to give the desired product. Yield 5.1 mg. MS: 484.2 (M+H$^+$); H$^1$ NMR (DMSO-d$_6$): δ (ppm) 0.54-0.78 (m, 4H), 1.77-2.05 (m, 3H), 2.14-2.37 (m, 1H), 2.80-2.94 (m, 1H), 3.40-3.58 (m, 2H), 4.30-4.44 (m, 1H), 4.38-5.14 (m, 2H), 7.00-8.07 (m, 13H), 8.49-8.59 (m, 1H), 10.10-10.09 (s, 1H).

Example 311

(S)-2-{3'-[(Cyclopropanecarbonyl-amino)-methyl]-biphenyl-3-ylcarbamoyl}-pyrrolidine-1-carboxylic acid benzyl ester (Compound 6311)

Cyclopropanecarboxylic acid 3-bromo-benzylamide

3-Bromo-benzylamine hydrochloride (437.3 mg, 2.0 mmol) was dissolved in dichloromethane (15 mL), and the solution was cooled to 0° C. DIEA (688.0 µL, 3.9 mmol) was then added, and the reaction was stirred at 0° C. for 5 minutes. Then cyclopropanecarbonyl chloride (180.0 µL, 2.3 mmol) was added, and the reaction was stirred at 0° C. for 20 minutes. The reaction was quenched with distilled water, and the solvents were removed. The resulting mixture was redissolved in DMF (10 mL) and purified by reverse phase HPLC to give the desired product.

(S)-2-{3'-[(Cyclopropanecarbonyl-amino)-methyl]-biphenyl-3-ylcarbamoyl}-pyrrolidine-1-carboxylic acid benzyl ester (Compound 6311)

A solution of (S)-2-[3-(4,4,5,5-tetramethyl-[1,3,2]dioxaborolan-2-yl)-phenylcarbamoyl]-pyrrolidine-1-carboxylic acid benzyl ester (74 mg, 0.16 mmol), cyclopropanecarboxylic acid 3-bromo-benzylamide (41.7 mg, 0.16 mmol), and Pd[P(Ph)$_3$]$_4$ (15.1 mg, 8.0 mol %) in methanol (2 mL), NaHCO$_3$ (sat. aq., 300 µL), and DMF (400 µL) was degassed and heated to 70° C. overnight in a sealed vial. The reaction was cooled, filtered, and purified by reverse phase HPLC to give the desired product. Yield 5.0 mg. MS: 498.3 (M+H$^+$); H$^1$ NMR (DMSO-d$_6$): δ (ppm) 0.55-0.70 (m, 4H), 1.50-1.60 (m, 1H), 1.73-1.98 (m, 3H), 2.07-2.29 (m, 1H), 3.35-3.56 (m, 2H), 4.24-4.37 (m, 3H), 4.85-5.08 (m, 2H), 6.97-7.54 (m, 12H), 7.63-780 (m, 1H), 8.50-8.59 (m, 1H), 10.06-10.13 (s, 1H).

Example 312

(S)-2-(3'-Cyclopropylcarbamoylmethyl-biphenyl-3-ylcarbamoyl)-pyrrolidine-1-carboxylic acid benzyl ester (Compound 6312)

2-(3-Bromo-phenyl)-N-cyclopropyl-acetamide (3-Bromo-phenyl)-acetic acid (636.0 mg, 3.0 mmol) and DCC (608.2 mg, 2.9 mmol) were dissolved in dichloromethane (15 mL) and stirred at ambient temperature for 5 minutes. Then cyclopropylamine (204.5 µL, 3.0 mmol) was added, and the reaction was stirred at ambient temperature overnight. The reaction was filtered, and the solvent was removed. The resulting mixture was redissolved in DMF (10 mL) and purified by reverse phase HPLC to give the desired product.

(S)-2-(3'-Cyclopropylcarbamoylmethyl-biphenyl-3-ylcarbamoyl)-pyrrolidine-1-carboxylic acid benzyl ester (Compound 6312)

A solution of (S)-2-[3-(4,4,5,5-tetramethyl-[1,3,2]dioxaborolan-2-yl)-phenylcarbamoyl]-pyrrolidine-1-carboxylic acid benzyl ester (74 mg, 0.16 mmol), 2-(3-bromo-phenyl)-N-cyclopropyl-acetamide (42.0 mg, 0.17 mmol), and Pd[P(Ph)$_3$]$_4$ (14.3 mg, 7.5 mol %) in methanol (2 mL), NaHCO$_3$ (sat. aq., 300 µL), and DMF (400 µL) was degassed and heated to 70° C. overnight in a sealed vial. The reaction was cooled, filtered, and purified by reverse phase HPLC to give the desired product. Yield 5.3 mg. MS: 498.2 (M+H$^+$); H$^1$-NMR (DMSO-d$_6$): δ (ppm) 0.31-0.39 (m, 2H), 0.52-0.60 (m, 2H), 1.74-2.00 (m, 3H), 2.10-2.30 (m, 1H), 2.50-2.62 (m, 1H), 3.34-3.54 (m, 2H), 4.28-4.38 (m, 1H), 4.85-5.08 (m, 2H), 6.95-7.55 (m, 12H), 7.80-7.92 (m, 1H), 8.05-8.18 (m, 1H), 10.05-10.12 (s, 1H).

BIOLOGICAL EXAMPLES

Example 1

Anti-Hepatitis C Activity

Compounds can exhibit anti-hepatitis C activity by inhibiting viral and host cell targets required in the replication cycle. A number of assays have been published to assess these activities. A general method that assesses the gross increase of HCV virus in culture is disclosed in U.S. Pat. No. 5,738,985 to Miles et al. In vitro assays have been reported in Ferrari et al. *J. of Vir.*, 73:1649-1654, 1999; Ishii et al., *Hepatology*, 29:1227-1235, 1999; Lohmann et al., *J. of Bio. Chem.*, 274:10807-10815, 1999; and Yamashita et al., *J. of Bio. Chem.*, 273:15479-15486, 1998.

Replicon Assay

A cell line, ET (Huh-lucubineo-ET) was used for screening of compounds of the present invention for HCV RNA dependent RNA polymerase. The ET cell line was stably transfected with RNA transcripts harboring a I$_{389}$luc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells were grown in DMEM, supplemented with 10% fetal calf serum, 2 mM Glutamine, Penicillin (100 IU/mL)/Stretomycin (100 µg/mL), 1× nonessential amino acids, and 250 µg/mL G418 ("Geneticin"). They were all available through Life Technologies (Bethesda, Md.). The cells were plated at 0.5–1.0× 10$^4$ cells/well in the 96 well plates and incubated for 24 hrs before adding nucleoside analogs. Then the compounds were added to the cells to achieve a final concentration of 5 or 50 µM. Luciferase activity were measured 48-72 hours later by adding a lysis buffer and the substrate (Catalog number Glolysis buffer E2661 and Bright-Glo luciferase system E2620 Promega, Madison, Wis.). Cells should not be too confluent during the assay. Percent inhibition of replication was plotted relative to no compound control. Under the same condition, cytotoxicity of the compounds was determined using cell proliferation reagent, WST-1 (Roche, Germany). The compounds showing antiviral activities, but no significant cytotoxicities were chosen to determine IC$_{50}$ and TC$_{50}$. For these determinations, 10 concentration of each compound were used. Concentrations for test compounds typically span a range of 500 fold. IC$_{50}$ and TC$_{50}$ values were calculated by fitting % inhibition at each concentration (I) to the following equation:

$$\% \text{ inhibition}=100\%/[1+10^{(\log IC50-\log(I))*b}]$$

where b is Hill's coefficient.

Preferably, when tested at 10 μM, the compounds of this invention will exhibit a % inhibition values of at least 25% and more preferably a % inhibition values of at least 50%.

Examples of % inhibition values at a test concentration of 10 μM according to the above equation are shown below.

| Compound | % inhib at 10 uM |
|---|---|
| 6001 | 87.85 |
| 6002 | 2.69 |
| 6003 | 1.21 |
| 6004 | 2.08 |
| 6005 | 3.63 |
| 6006 | 70.05 |
| 6007 | 93.41 |
| 6008 | 79.77 |
| 6009 | 83.29 |
| 6010 | 98.61 |
| 6011 | 99.72 |
| 6012 | 44.49 |
| 6013 | 32.48 |
| 6014 | 99.60 |
| 6019 | 10.47 |
| 6020 | 99.86 |
| 6021 | 56.10 |
| 6022 | 87.35 |
| 6023 | 75.41 |
| 6024 | 98.09 |
| 6025 | 5.45 |
| 6026 | 98.72 |
| 6027 | 98.13 |
| 6028 | 75.00 |
| 6029 | 3.08 |
| 6030 | 42.24 |
| 6031 | 28.61 |
| 6032 | 44.53 |
| 6033 | 8.26 |
| 6034 | 26.70 |
| 6035 | 42.55 |
| 6036 | 22.89 |
| 6037 | 8.60 |
| 6038 | 9.34 |
| 6039 | 33.82 |
| 6043 | 93.93 |
| 6044 | 73.19 |
| 6045 | 15.67 |
| 6047 | 1.38 |
| 6048 | 36.85 |
| 6051 | 68.76 |
| 6052 | 48.32 |
| 6053 | 93.27 |
| 6054 | 97.67 |
| 6055 | 40.92 |
| 6056 | 80.82 |
| 6057 | 61.71 |
| 6082 | 97.36 |
| 6083 | 93.79 |
| 6084 | 3.35 |
| 6085 | 39.68 |
| 6086 | 89.94 |
| 6087 | 78.91 |
| 6088 | 99.88 |
| 6089 | 76.43 |
| 6090 | 59.57 |
| 6091 | 97.73 |
| 6092 | 95.31 |
| 6093 | 98.07 |
| 6094 | 98.82 |
| 6095 | 61.61 |
| 6096 | 53.32 |
| 6097 | 99.85 |
| 6301 | 99.06 |
| 6302 | 12.16 |
| 6304 | 70.36 |
| 6305 | 88.24 |
| 6307 | 32.32 |
| 6308 | 56.21 |
| 6309 | 99.76 |
| 6310 | 78.41 |
| 6311 | 94.22 |
| 6312 | 68.63 |

Formulation Examples

The following are representative pharmaceutical formulations containing a compound of the present invention.

Example 1

Tablet Formulation

The following ingredients are mixed intimately and pressed into single scored tablet.

| Ingredient | Quantity per tablet, mg |
|---|---|
| Compound of the invention | 400 |
| Cornstarch | 50 |
| Croscarmellose sodium | 25 |
| Lactose | 120 |
| Magnesium stearate | 5 |

Example 2

Capsule Formulation

The following ingredients are mixed intimately and loaded into a hard-shell gelatin capsule.

| Ingredient | Quantity per tablet, mg |
|---|---|
| Compound of the invention | 200 |
| Lactose, spray-dried | 148 |
| Magnesium stearate | 2 |

Example 3

Suspension Formulation

The following ingredients are mixed to form a suspension for oral administration (q.s.=sufficient amount).

| Ingredient | Amount | |
|---|---|---|
| Compound of the invention | 1.0 | g |
| Fumaric acid | 0.5 | g |
| Sodium chloride | 2.0 | g |
| Methyl paraben | 0.15 | g |
| Propyl paraben | 0.05 | g |
| Granulated sugar | 25.0 | g |
| Sorbitol (70% solution) | 13.0 | g |
| Veegum K (Vanderbilt Co.) | 1.0 | g |
| flavoring | 0.035 | mL |
| colorings | 0.5 | mg |
| distilled water | q.s. to 100 | mL |

Example 4

Injectable Formulation

The following ingredients are mixed to form an injectable formulation.

| Ingredient | Quantity per tablet, mg |
|---|---|
| Compound of the invention | 0.2 mg-20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
|---|---|
| Compound of the invention | 500 mg |
| Witepsol ® H-15 | balance |

What is claimed is:

1. A compound selected from the group consisting of
2-(2',4'-Dimethoxy-biphenyl-4-ylcarbamoyl)-pyrrolidine-1-carboxylic acid benzyl ester;
2-(4-Benzenesulfonylamino-phenylcarbamoyl)-pyrrolidine-1-carboxylic acid benzyl ester;
2-[4-(4-Methyl-piperidine-1-sulfonyl)-phenylcarbamoyl]-pyrrolidine-1-carboxylic acid benzyl ester;
2-[4-(2,6-Dichloro-phenylcarbamoyl)-phenylcarbamoyl]-pyrrolidine-1-carboxylic acid benzyl ester;
2-[4-(3-Methyl-5-oxo-1-phenyl-1,5-dihydro-pyrazol-4-ylidenemethyl)-phenylcarbamoyl]-pyrrolidine-1-carboxylic acid benzyl ester;
2-[4-(6-Bromo-4,5-dimethyl-1H-benzoimidazol-2-ylmethyl)-phenylcarbamoyl]-pyrrolidine-1-carboxylic acid benzyl ester;
2-(2',5'-Dimethoxy-biphenyl-4-ylcarbamoyl)-pyrrolidine-1-carboxylic acid benzyl ester;
2-(3'-Methoxy-biphenyl-3-ylcarbamoyl)-pyrrolidine-1-carboxylic acid benzyl ester;
2-[4-(1H-Indol-5-yl)-phenylcarbamoyl]-pyrrolidine-1-carboxylic acid benzyl ester;
2-[3-(1H-Indol-5-yl)-phenylcarbamoyl]-pyrrolidine-1-carboxylic acid benzyl ester;
2-([1,1';3',1"]Terphenyl-4-ylcarbamoyl)-pyrrolidine-1-carboxylic acid benzyl ester;
2-(3-Pentafluorophenyloxy-phenylcarbamoyl)-pyrrolidine-1-carboxylic acid benzyl ester;
2-(3-Benzenesulfonyl-phenylcarbamoyl)-pyrrolidine-1-carboxylic acid benzyl ester;
2-[4-(5,6-Dimethyl-1H-benzoimidazol-2-ylmethyl)-phenylcarbamoyl]-pyrrolidine-1-carboxylic acid benzyl ester;
2-[4-(5-Methyl-1H-benzoimidazol-2-ylmethyl)-phenylcarbamoyl]-pyrrolidine-1-carboxylic acid benzyl ester;
2-[4-(4,5-Dimethyl-1H-benzoimidazol-2-ylmethyl)-phenylcarbamoyl]-pyrrolidine-1-carboxylic acid benzyl ester;
2-[4-(5-Bromo-1H-benzoimidazol-2-ylmethyl)-phenylcarbamoyl]-pyrrolidine-1-carboxylic acid benzyl ester;
2-[4-(4-Methyl-1H-benzoimidazol-2-ylmethyl)-phenylcarbamoyl]-pyrrolidine-1-carboxylic acid benzyl ester;
2-(4'-Methoxy-biphenyl-4-ylcarbamoyl)-pyrrolidine-1-carboxylic acid benzyl ester;
2-[4-(1H-Naphtho[2,3-d]imidazol-2-ylmethyl)-phenylcarbamoyl]-pyrrolidine-1-carboxylic acid benzyl ester;
2-(3'-Phenoxymethyl-biphenyl-4-ylcarbamoyl)-pyrrolidine-1-carboxylic acid benzyl ester;
2-(3-Thiophen-2-yl-phenylcarbamoyl)-pyrrolidine-1-carboxylic acid benzyl ester;
2-(4-Thiophen-2-yl-phenylcarbamoyl)-pyrrolidine-1-carboxylic acid benzyl ester;
2-[3-Phenoxy-5-(pyridin-3-yloxy)-phenylcarbamoyl]-pyrrolidine-1-carboxylic acid benzyl ester;
2-[4-(5-Furan-2-yl-[1,3,4]oxadiazol-2-yl)-phenylcarbamoyl]-pyrrolidine-1-carboxylic acid benzyl ester;
2-(2',3'-Dimethoxybiphenyl-3-yl-carbamoyl)-pyrrolidine-1-carboxylic acid benzyl ester;
2-{3-[4-(Toluene-4-sulfonyl)-phenoxy]-phenylcarbamoyl}-pyrrolidine-1-carboxylic acid benzyl ester;
2-(2',3'-Dimethoxy-biphenyl-4-ylcarbamoyl)-pyrrolidine-1-carboxylic acid benzyl ester;
2-(3',4'-Dimethoxybiphenyl-3-yl-carbamoyl)-pyrrolidine-1-carboxylic acid benzyl ester;
2-[4-(6-Methoxy-benzothiazol-2-ylcarbamoyl)-phenylcarbamoyl]-pyrrolidine-1-carboxylic acid benzyl ester;
2-(2'-Methoxybiphenyl-3-yl-carbamoyl)-pyrrolidine-1-carboxylic acid benzyl ester;
2-[3-Nitro-5-(6,7,8,9-tetrahydro-dibenzofuran-2-yloxy)-phenylcarbamoyl]-pyrrolidine-1-carboxylic acid benzyl ester;
2-(2',6'-Dimethoxybiphenyl-3-yl-carbamoyl)-pyrrolidine-1-carboxylic acid benzyl ester;
2-(3-Phenoxy-phenylcarbamoyl)-pyrrolidine-1-carboxylic acid benzyl ester;
2-(Biphenyl-4-ylcarbamoyl)-pyrrolidine-1-carboxylic acid benzyl ester;
2-(2',6'-Dimethoxy-biphenyl-4-ylcarbamoyl)-pyrrolidine-1-carboxylic acid benzyl ester;
2-(4'-Methoxybiphenyl-3-yl-carbamoyl)-pyrrolidine-1-carboxylic acid benzyl ester;
2-[4-(1H-Benzoimidazol-2-ylmethyl)-phenylcarbamoyl]-pyrrolidine-1-carboxylic acid benzyl ester;
2-(3-Nitro-5-m-tolyloxy-phenylcarbamoyl)-pyrrolidine-1-carboxylic acid benzyl ester;
2-[4-(3-Ethyl-2,6-dioxo-piperidin-3-yl)-phenylcarbamoyl]-pyrrolidine-1-carboxylic acid benzyl ester;
2-(4'-Aminomethyl-biphenyl-3-ylcarbamoyl)-pyrrolidine-1-carboxylic acid benzyl ester;
2-(3-Benzo[1,3]dioxol-5-yl-phenylcarbamoyl)-pyrrolidine-1-carboxylic acid benzyl ester;
2-(3-Naphthalen-2-yl-phenylcarbamoyl)-pyrrolidine-1-carboxylic acid benzyl ester;
2-(4'-Dimethylamino-biphenyl-3-ylcarbamoyl)-pyrrolidine-1-carboxylic acid benzyl ester;
2-(4'-Methanesulfonyl-biphenyl-3-ylcarbamoyl)-pyrrolidine-1-carboxylic acid benzyl ester;
2-[3-(5-Acetyl-thiophen-2-yl)-phenylcarbamoyl]-pyrrolidine-1-carboxylic acid benzyl ester;
2-{4-[2-(2-Chloro-phenylcarbamoyl)-acetyl]-phenylcarbamoyl}-pyrrolidine-1-carboxylic acid benzyl ester;

2-(4-Piperidin-1-yl-phenylcarbamoyl)-pyrrolidine-1-carboxylic acid benzyl ester;
2-[3-(1-Methyl-1H-indol-5-yl)-phenylcarbamoyl]-pyrrolidine-1-carboxylic acid benzyl ester;
2-(4'-Acetyl-biphenyl-3-ylcarbamoyl)-pyrrolidine-1-carboxylic acid benzyl ester;
2-(4'-Nitro-biphenyl-3-ylcarbamoyl)-pyrrolidine-1-carboxylic acid benzyl ester;
2-(3'-Amino-biphenyl-3-ylcarbamoyl)-pyrrolidine-1-carboxylic acid benzyl ester;
2-[4'-(2-Carboxy-vinyl)-biphenyl-3-ylcarbamoyl]-pyrrolidine-1-carboxylic acid benzyl ester;
2-(4'-Acetylamino-biphenyl-3-ylcarbamoyl)-pyrrolidine-1-carboxylic acid benzyl ester;
2-(3'-Acetylamino-biphenyl-3-ylcarbamoyl)-pyrrolidine-1-carboxylic acid benzyl ester;
2-[4-(4-Ethylamino-6-isopropylamino-[1,3,5]triazin-2-ylsulfamoyl)-phenylcarbamoyl]-pyrrolidine-1-carboxylic acid benzyl ester;
2-([1,1';4',1']Terphenyl-4-ylcarbamoyl)-pyrrolidine-1-carboxylic acid benzyl ester;
2-(4-Morpholin-4-yl-phenylcarbamoyl)-pyrrolidine-1-carboxylic acid benzyl ester;
2-[4-(4-Methyl-pyridin-2-ylsulfamoyl)-phenylcarbamoyl]-pyrrolidine-1-carboxylic acid benzyl ester;
2-[3-(5-Chloro-pyridin-3-yloxy)-5-nitro-phenylcarbamoyl]-pyrrolidine-1-carboxylic acid benzyl ester;
2-[3-(Quinazolin-4-ylamino)-phenylcarbamoyl]-pyrrolidine-1-carboxylic acid benzyl ester;
2-[4-(5-Cyano-1H-benzoimidazol-2-ylmethyl)-phenylcarbamoyl]-pyrrolidine-1-carboxylic acid benzyl ester;
2-[4-(Morpholine-4-carbonyl)-phenylcarbamoyl]-pyrrolidine-1-carboxylic acid benzyl ester;
2-(3-Pyridin-4-yl-phenylcarbamoyl)-pyrrolidine-1-carboxylic acid benzyl ester;
2-(4-Benzothiazol-2-yl-phenylcarbamoyl)-pyrrolidine-1-carboxylic acid benzyl ester;
2-[3-(2-Morpholin-4-yl-2-oxo-ethoxy)-phenylcarbamoyl]-pyrrolidine-1-carboxylic acid benzyl ester;
2-(4-Morpholin-4-ylmethyl-phenylcarbamoyl)-pyrrolidine-1-carboxylic acid benzyl ester;
2-[3-(4-Nitro-phenoxy)-phenylcarbamoyl]-pyrrolidine-1-carboxylic acid benzyl ester;
2-[4-(5-tert-Butyl-1H-benzoimidazol-2-ylmethyl)-phenylcarbamoyl]-pyrrolidine-1-carboxylic acid benzyl ester;
2-(4-Pyrrolidin-1-ylmethyl-phenylcarbamoyl)-pyrrolidine-1-carboxylic acid benzyl ester;
2-(2'-Methoxy-biphenyl-4-ylcarbamoyl)-pyrrolidine-1-carboxylic acid benzyl ester;
2-(4-Pyridin-4-yl-phenylcarbamoyl)-pyrrolidine-1-carboxylic acid benzyl ester;
2-[4-(Piperidine-1-carbonyl)-phenylcarbamoyl]-pyrrolidine-1-carboxylic acid benzyl ester;
2-(3-Quinolin-3-yl-phenylcarbamoyl)-pyrrolidine-1-carboxylic acid benzyl ester;
2-[3-(1H-Indol-4-yl)-phenylcarbamoyl]-pyrrolidine-1-carboxylic acid benzyl ester;
2-[3-(2-Oxo-2,3-dihydro-1H-indol-5-yl)-phenylcarbamoyl]-pyrrolidine-1-carboxylic acid benzyl ester;
2-[3-(2,3-Dioxo-2,3-dihydro-1H-indol-5-yl)-phenylcarbamoyl]-pyrrolidine-1-carboxylic acid benzyl ester;
2-[3-(2-Methyl-quinolin-6-yl)-phenylcarbamoyl]-pyrrolidine-1-carboxylic acid benzyl ester;
2-(4'-Amino-biphenyl-3-ylcarbamoyl)-pyrrolidine-1-carboxylic acid benzyl ester;
2-(3'-Acetyl-biphenyl-3-ylcarbamoyl)-pyrrolidine-1-carboxylic acid benzyl ester;
2-[3-(6-Hydroxy-naphthalen-2-yl)-phenylcarbamoyl]-pyrrolidine-1-carboxylic acid benzyl ester;
2-(3'-Methylamino-biphenyl-3-ylcarbamoyl)-pyrrolidine-1-carboxylic acid benzyl ester;
2-(3'-Amino-2'-methyl-biphenyl-3-ylcarbamoyl)-pyrrolidine-1-carboxylic acid benzyl ester;
2-[3-(2-Methyl-benzothiazol-5-yl)-phenylcarbamoyl]-pyrrolidine-1-carboxylic acid benzyl ester;
2-(3'-Hydroxy-biphenyl-3-ylcarbamoyl)-pyrrolidine-1-carboxylic acid benzyl ester;
2-(3'-Ureido-biphenyl-3-ylcarbamoyl)-pyrrolidine-1-carboxylic acid benzyl ester;
2-[3-(1H-Indol-7-yl)-phenylcarbamoyl]-pyrrolidine-1-carboxylic acid benzyl ester;
2-(3'-Amino-5'-trifluoromethyl-biphenyl-3-ylcarbamoyl)-pyrrolidine-1-carboxylic acid benzyl ester;
2-(3'-Dimethylamino-biphenyl-3-ylcarbamoyl)-pyrrolidine-1-carboxylic acid benzyl ester;
2-[3-(1H-Indol-6-yl)-phenylcarbamoyl]-pyrrolidine-1-carboxylic acid benzyl ester;
2-[3-(2,3-Dihydro-1H-indol-5-yl)-phenylcarbamoyl]-pyrrolidine-1-carboxylic acid benzyl ester;
2-[3-(1H-Benzoimidazol-5-yl)-phenylcarbamoyl]-pyrrolidine-1-carboxylic acid benzyl ester;
2-(Biphenyl-3-ylcarbamoyl)-pyrrolidine-1-carboxylic acid benzyl ester;
2-[3-(2-Methyl-quinolin-6-yl)-phenylcarbamoyl]-pyrrolidine-1-carboxylic acid benzyl ester;
5-{3-[(1-Benzyloxycarbonyl-pyrrolidine-2-carbonyl)-amino]-phenyl}-1H-indole-2-carboxylic acid;
2-[3-(3-Dimethylaminomethyl-1H-indol-5-yl)-phenylcarbamoyl]-pyrrolidine-1-carboxylic acid benzyl ester;
2-{3-[3-(2-Amino-ethyl)-1H-indol-5-yl]-phenylcarbamoyl}-pyrrolidine-1-carboxylic acid benzyl ester;
2-[3-(2-Methyl-1H-indol-5-yl)-phenylcarbamoyl]-pyrrolidine-1-carboxylic acid benzyl ester;
2-[3-(6,7,8,9-Tetrahydro-5H-carbazol-3-yl)-phenylcarbamoyl]-pyrrolidine-1-carboxylic acid benzyl ester;
2-[3-(7-Nitro-1H-indol-5-yl)-phenylcarbamoyl]-pyrrolidine-1-carboxylic acid benzyl ester;
2-[3-(7-Amino-1H-indol-5-yl)-phenylcarbamoyl]-pyrrolidine-1-carboxylic acid benzyl ester;
2-(3-Quinoxalin-2-yl-phenylcarbamoyl)-pyrrolidine-1-carboxylic acid benzyl ester;
2-[3-(2-Oxo-2,3-dihydro-1H-benzoimidazol-5-yl)-phenylcarbamoyl]-pyrrolidine-1-carboxylic acid benzyl ester;
2-[3-(2-Oxo-2H-chromen-6-yl)-phenylcarbamoyl]-pyrrolidine-1-carboxylic acid benzyl ester;
2-[3-(3-Methyl-2-oxo-2H-chromen-6-yl)-phenylcarbamoyl]-pyrrolidine-1-carboxylic acid benzyl ester;
2-[3-(3-Methyl-2-oxo-1,2-dihydro-quinoxalin-6-yl)-phenylcarbamoyl]-pyrrolidine-1-carboxylic acid benzyl ester;
2-[3-(1H-Benzotriazol-5-yl)-phenylcarbamoyl]-pyrrolidine-1-carboxylic acid benzyl ester;
2-[4'-(3,4-Dichloro-2,5-dioxo-2,5-dihydro-pyrrol-1-yl)-biphenyl-3-ylcarbamoyl]-pyrrolidine-1-carboxylic acid benzyl ester;
2-[4'-(3-Methyl-5-oxo-4,5-dihydro-pyrazol-1-yl)-biphenyl-3-ylcarbamoyl]-pyrrolidine-1-carboxylic acid benzyl ester;
2-[4'-(3-Oxo-1,3-dihydro-indazol-2-yl)-biphenyl-3-ylcarbamoyl]-pyrrolidine-1-carboxylic acid benzyl ester;

2-[4'-(1,3-Dioxo-1,3-dihydro-isoindol-2-yl)-biphenyl-3-ylcarbamoyl]-pyrrolidine-1-carboxylic acid benzyl ester;
2-[4'-(2-Oxo-2,5-dihydro-pyrrol-1-yl)-biphenyl-3-ylcarbamoyl]-pyrrolidine-1-carboxylic acid benzyl ester;
2-[4'-(5-Methyl-thiazol-2-yl)-biphenyl-3-ylcarbamoyl]-pyrrolidine-1-carboxylic acid benzyl ester;
2-(4'-Oxazol-5-yl-biphenyl-3-ylcarbamoyl)-pyrrolidine-1-carboxylic acid benzyl ester;
1-Phenylacetyl-pyrrolidine-2-carboxylic acid [3-(1H-indol-5-yl)-phenyl]-amide;
3-Hydroxy-2-[3-(1H-indol-5-yl)-phenylcarbamoyl]-pyrrolidine-1-carboxylic acid benzyl ester;
3-Hydroxy-2-[3-(1H-indol-5-yl)-phenylcarbamoyl]-pyrrolidine-1-carboxylic acid benzyl ester;
4-Hydroxy-2-[3-(1H-indol-5-yl)-phenylcarbamoyl]-pyrrolidine-1-carboxylic acid benzyl ester;
4-[3-(1H-Indol-5-yl)-phenylcarbamoyl]-thiazolidine-3-carboxylic acid benzyl ester;
2-[3-(1H-Indol-5-yl)-phenylcarbamoyl]-4-isopropoxy-pyrrolidine-1-carboxylic acid benzyl ester;
2-[3-(1H-Indol-5-yl)-phenylcarbamoyl]-pyrrolidine-1-carboxylic acid methyl ester;
2-[3-(1H-Indol-5-yl)-5-nitro-phenylcarbamoyl]-pyrrolidine-1-carboxylic acid benzyl ester;
2-[3-Carboxy-5-(1H-indol-5-yl)-phenylcarbamoyl]-pyrrolidine-1-carboxylic acid benzyl ester;
2-[3-(1H-Indol-5-yl)-5-methoxy-phenylcarbamoyl]-pyrrolidine-1-carboxylic acid benzyl ester;
2-[3-Amino-5-(1H-indol-5-yl)-phenylcarbamoyl]-pyrrolidine-1-carboxylic acid benzyl ester;
2-(4'-Cyclopropylcarbamoyl-biphenyl-3-ylcarbamoyl)-pyrrolidine-1-carboxylic acid benzyl ester;
2-[3-(4-Cyclopropylcarbamoyl-thiazol-2-yl)-phenylcarbamoyl]-pyrrolidine-1-carboxylic acid benzyl ester;
2-(3'-Methylaminomethyl-biphenyl-3-ylcarbamoyl)-pyrrolidine-1-carboxylic acid benzyl ester;
2-(3-Benzothiazol-6-yl-phenylcarbamoyl)-pyrrolidine-1-carboxylic acid benzyl ester;
2-(4-Cyclopropylcarbamoyl-phenylcarbamoyl)-pyrrolidine-1-carboxylic acid benzyl ester;
2-(4'-Cyclopropylcarbamoylmethyl-biphenyl-3-ylcarbamoyl)-pyrrolidine-1-carboxylic acid benzyl ester;
2-(3'-Cyano-biphenyl-3-ylcarbamoyl)-pyrrolidine-1-carboxylic acid benzyl ester;
2-{4'-[(Cyclopropanecarbonyl-amino)-methyl]-biphenyl-3-ylcarbamoyl}-pyrrolidine-1-carboxylic acid benzyl ester;
2-(3'-Nitro-biphenyl-3-ylcarbamoyl)-pyrrolidine-1-carboxylic acid benzyl ester;
2-(3'-Cyclopropylcarbamoyl-biphenyl-3-ylcarbamoyl)-pyrrolidine-1-carboxylic acid benzyl ester;
2-{3'-[(Cyclopropanecarbonyl-amino)-methyl]-biphenyl-3-ylcarbamoyl}-pyrrolidine-1-carboxylic acid benzyl ester;
2-(3'-Cyclopropylcarbamoylmethyl-biphenyl-3-ylcarbamoyl)-pyrrolidine-1-carboxylic acid benzyl ester;
or a stereoisomer, tautomer, or a pharmaceutically acceptable salt thereof.

* * * * *